(12) United States Patent
Khvorova et al.

(10) Patent No.: US 12,365,894 B2
(45) Date of Patent: Jul. 22, 2025

(54) BRANCHED LIPID CONJUGATES OF siRNA FOR SPECIFIC TISSUE DELIVERY

(71) Applicant: UNIVERSITY OF MASSACHUSETTS, Boston, MA (US)

(72) Inventors: Anastasia Khvorova, Westborough, MA (US); Annabelle Biscans, Cambridge, MA (US)

(73) Assignee: UNIVERSITY OF MASSACHUSETTS, Westborough, MA (US)

( * ) Notice: Subject to any disclaimer, the term of this patent is extended or adjusted under 35 U.S.C. 154(b) by 685 days.

(21) Appl. No.: 17/022,678

(22) Filed: Sep. 16, 2020

(65) Prior Publication Data

US 2021/0108200 A1    Apr. 15, 2021

Related U.S. Application Data

(60) Provisional application No. 62/900,971, filed on Sep. 16, 2019.

(51) Int. Cl.
    *C12N 15/113*    (2010.01)
    *A61K 31/713*    (2006.01)

(52) U.S. Cl.
    CPC .......... *C12N 15/113* (2013.01); *A61K 31/713* (2013.01); *C12N 2310/315* (2013.01); *C12N 2310/321* (2013.01); *C12N 2310/322* (2013.01); *C12N 2310/3515* (2013.01)

(58) Field of Classification Search
    CPC ............ C12N 15/113; C12N 2310/315; C12N 2310/321; C12N 2310/322; C12N 2310/3515; C12N 2310/14; C12N 2310/312; C12N 2310/343; C12N 2310/346; C12N 2310/3517; C12N 2320/32; A61K 31/713
    See application file for complete search history.

(56) References Cited

U.S. PATENT DOCUMENTS

| | | |
|---|---|---|
| 4,522,811 A | 6/1985 | Eppstein et al. |
| 5,194,596 A | 3/1993 | Tischer et al. |
| 5,219,739 A | 6/1993 | Tischer et al. |
| 5,240,848 A | 8/1993 | Keck et al. |
| 5,328,470 A | 7/1994 | Nabel et al. |
| 5,332,671 A | 7/1994 | Ferrara et al. |
| 5,684,143 A | 11/1997 | Grayaznov et al. |
| 5,814,014 A | 9/1998 | Elsberry et al. |
| 5,858,988 A | 1/1999 | Wang |
| 5,939,402 A | 8/1999 | Weis et al. |
| 6,025,335 A | 2/2000 | Weis et al. |
| 6,093,180 A | 7/2000 | Elsberry et al. |
| 6,107,094 A | 8/2000 | Crooke |
| 6,168,587 B1 | 1/2001 | Bellhouse et al. |
| 6,177,403 B1 | 1/2001 | Stedman |
| 6,194,389 B1 | 2/2001 | Johnston et al. |
| 6,291,438 B1 | 9/2001 | Wang |
| 6,312,900 B1 | 11/2001 | Dean et al. |
| 6,383,814 B1 | 5/2002 | Lee et al. |
| 6,447,768 B1 | 9/2002 | van Zonneveld et al. |
| 6,471,996 B1 | 10/2002 | Sokoll et al. |
| 6,472,375 B1 | 10/2002 | Hoon et al. |
| 6,489,464 B1 | 12/2002 | Agrawal et al. |
| 7,250,496 B2 | 7/2007 | Bentwich |
| 7,459,547 B2 | 12/2008 | Zamore et al. |
| 7,691,997 B2 | 4/2010 | Khvorova et al. |
| 7,723,512 B2 | 5/2010 | Manoharan et al. |
| 7,732,593 B2 | 6/2010 | Zamore et al. |
| 7,750,144 B2 | 7/2010 | Zamore et al. |
| 7,772,203 B2 | 8/2010 | Zamore et al. |
| 7,790,867 B2 | 9/2010 | Bentwich |
| 7,820,809 B2 | 10/2010 | Khvorova et al. |
| 7,834,171 B2 | 11/2010 | Leake et al. |
| 8,013,136 B2 | 9/2011 | Manoharan et al. |
| 8,097,752 B2 | 1/2012 | Calogeropolou et al. |
| 8,304,530 B2 | 11/2012 | Zamore et al. |
| 8,309,704 B2 | 11/2012 | Zamore et al. |
| 8,309,705 B2 | 11/2012 | Zamore et al. |
| 8,329,892 B2 | 12/2012 | Zamore et al. |
| 8,431,544 B1 | 4/2013 | Agrawal et al. |
| 8,501,706 B2 | 8/2013 | Yamada et al. |
| 8,507,661 B2 | 8/2013 | Manoharan et al. |
| 8,664,189 B2 | 3/2014 | Khvorova et al. |
| 8,703,731 B2 | 4/2014 | Jimenez et al. |
| 8,796,443 B2 | 8/2014 | Khvorova et al. |
| 8,815,818 B2 | 8/2014 | Samarsky et al. |
| 8,871,774 B2 | 10/2014 | Charifson et al. |
| 8,877,439 B2 | 11/2014 | Butora et al. |
| 8,906,874 B2 | 12/2014 | Rao et al. |

(Continued)

FOREIGN PATENT DOCUMENTS

| | | |
|---|---|---|
| CN | 101199858 A | 6/2008 |
| CN | 101365801 A | 2/2009 |

(Continued)

OTHER PUBLICATIONS

Khorev et al. 2008. Trivalent, Gal/GalNAc-containing ligands designed for the asialoglycoprotein receptor. Bioorgan. & Medicin. Chem. 16:5216-5231 (Year: 2008).*

(Continued)

*Primary Examiner* — Nancy J Leith
*Assistant Examiner* — Ruth Sophia Arieti
(74) *Attorney, Agent, or Firm* — LATHROP GPM LLP; James H. Velema, Esq.; Michael J. Spellberg

(57) ABSTRACT

This disclosure relates to an siRNA-lipid conjugate of formula Y-L-(H)$_n$. Y is an siRNA molecule, L is a linker covalently bonded to Y and H, each H is independently a hydrophobic chain comprising 5 to 50 carbon atoms, n is 1, 2, or 3, and linker L is bonded to the 3' end of the sense strand of the siRNA.

17 Claims, 12 Drawing Sheets

(9 of 12 Drawing Sheet(s) Filed in Color)

(56) References Cited

U.S. PATENT DOCUMENTS

| | | |
|---|---|---|
| 8,993,738 B2 | 3/2015 | Prakash et al. |
| 9,029,389 B2 | 5/2015 | No et al. |
| 9,074,211 B2 | 7/2015 | Woolf et al. |
| 9,080,171 B2 | 7/2015 | Khvorova et al. |
| 9,095,504 B2 | 8/2015 | Libertine et al. |
| 9,175,289 B2 | 11/2015 | Khvorova et al. |
| 9,198,981 B2 | 12/2015 | Ambati et al. |
| 9,303,259 B2 | 4/2016 | Khvorova et al. |
| 9,340,786 B2 | 5/2016 | Khvorova et al. |
| 9,493,774 B2 | 11/2016 | Kamens et al. |
| 9,745,574 B2 | 8/2017 | Woolf et al. |
| 9,796,756 B2 | 10/2017 | Hadwiger et al. |
| 9,809,817 B2 * | 11/2017 | Khvorova ............ A61K 9/0085 |
| 9,862,350 B2 | 1/2018 | Guerrero et al. |
| 9,862,952 B2 | 1/2018 | Khvorova et al. |
| 9,867,882 B2 | 1/2018 | Manoharan et al. |
| 10,087,210 B2 | 10/2018 | Prakash et al. |
| 10,435,688 B2 | 10/2019 | Khvorova et al. |
| 10,478,503 B2 | 11/2019 | Khvorova et al. |
| 10,479,992 B2 | 11/2019 | Woolf et al. |
| 10,519,451 B2 | 12/2019 | Khvorova et al. |
| 10,633,653 B2 | 4/2020 | Khvorova et al. |
| 10,774,327 B2 | 9/2020 | Khvorova et al. |
| 10,799,591 B2 | 10/2020 | Khvorova et al. |
| 10,844,377 B2 | 11/2020 | Khvorova et al. |
| 11,230,713 B2 | 1/2022 | Khvorova et al. |
| 11,279,930 B2 | 3/2022 | Khvorova et al. |
| 11,345,917 B2 | 5/2022 | Khvorova et al. |
| 11,492,619 B2 | 11/2022 | Khvorova et al. |
| 11,667,915 B2 | 6/2023 | Woolf et al. |
| 11,702,659 B2 | 7/2023 | Khvorova et al. |
| 11,753,638 B2 | 9/2023 | Khvorova et al. |
| 11,827,882 B2 | 11/2023 | Khvorova et al. |
| 11,896,669 B2 | 2/2024 | Khvorova et al. |
| 2001/0027251 A1 | 10/2001 | Cook et al. |
| 2003/0045705 A1 | 3/2003 | Cook |
| 2003/0143732 A1 | 7/2003 | Fosnaugh et al. |
| 2004/0121426 A1 | 6/2004 | Hsieh |
| 2004/0198640 A1 | 10/2004 | Leake et al. |
| 2004/0205839 A1 | 10/2004 | Doutriaux et al. |
| 2005/0096284 A1 | 5/2005 | McSwiggen |
| 2005/0220766 A1 | 10/2005 | Amalfitano et al. |
| 2005/0255487 A1 | 11/2005 | Khvorova et al. |
| 2006/0009409 A1 | 1/2006 | Woolf |
| 2006/0024715 A1 | 2/2006 | Liu et al. |
| 2006/0078542 A1 | 4/2006 | Mah et al. |
| 2006/0094032 A1 | 5/2006 | Fougerolles et al. |
| 2006/0105998 A1 | 5/2006 | Calogeropoulou et al. |
| 2007/0004664 A1 | 1/2007 | McSwiggen et al. |
| 2007/0004665 A1 | 1/2007 | McSwiggen et al. |
| 2007/0099860 A1 | 5/2007 | Sah et al. |
| 2007/0135372 A1 | 6/2007 | MacLachlan et al. |
| 2007/0160534 A1 | 7/2007 | Dennis et al. |
| 2007/0191273 A1 | 8/2007 | Ambat et al. |
| 2007/0259827 A1 | 11/2007 | Aronin et al. |
| 2008/0039415 A1 | 2/2008 | Stewart et al. |
| 2008/0108583 A1 | 5/2008 | Feinstein |
| 2008/0108801 A1 | 5/2008 | Manoharan |
| 2008/0119427 A1 | 5/2008 | Bhat et al. |
| 2008/0188429 A1 | 8/2008 | Iyer |
| 2008/0269149 A1 | 10/2008 | Bowles et al. |
| 2009/0143322 A1 | 6/2009 | Burkoth et al. |
| 2009/0234109 A1 | 9/2009 | Han et al. |
| 2009/0281299 A1 | 11/2009 | Manorahan et al. |
| 2009/0306178 A1 | 12/2009 | Bhat et al. |
| 2009/0318676 A1 | 12/2009 | Manoharan et al. |
| 2010/0015706 A1 | 1/2010 | Quay et al. |
| 2010/0093085 A1 | 4/2010 | Yamada et al. |
| 2010/0184209 A1 | 7/2010 | Vermeulen et al. |
| 2010/0186103 A1 | 7/2010 | Gao et al. |
| 2010/0240730 A1 | 9/2010 | Beigelman et al. |
| 2011/0039914 A1 | 2/2011 | Pavco et al. |
| 2011/0046206 A1 | 2/2011 | Bhat et al. |
| 2011/0086905 A1 | 4/2011 | Glazer |
| 2011/0097716 A1 | 4/2011 | Natt et al. |
| 2011/0201006 A1 | 8/2011 | Roehl et al. |
| 2011/0237522 A1 | 9/2011 | Khvorova et al. |
| 2011/0237648 A1 | 9/2011 | Khvorova et al. |
| 2011/0251258 A1 | 10/2011 | Samarsky et al. |
| 2011/0263680 A1 | 10/2011 | Khvorova et al. |
| 2012/0016005 A1 | 1/2012 | Samarsky et al. |
| 2012/0040459 A1 | 2/2012 | Khvorova et al. |
| 2012/0052487 A9 | 3/2012 | Khvorova et al. |
| 2012/0059046 A1 | 3/2012 | Woolf et al. |
| 2012/0065243 A1 | 3/2012 | Woolf et al. |
| 2012/0136039 A1 | 5/2012 | Aronin et al. |
| 2013/0065298 A1 | 3/2013 | Davidson et al. |
| 2013/0131141 A1 | 5/2013 | Khvorova et al. |
| 2013/0131142 A1 | 5/2013 | Libertine et al. |
| 2013/0178513 A1 | 7/2013 | Dobie et al. |
| 2013/0196434 A1 | 8/2013 | Maier et al. |
| 2013/0197055 A1 | 8/2013 | Kamens et al. |
| 2013/0345218 A1 | 12/2013 | Charifson et al. |
| 2014/0005192 A1 | 1/2014 | Charifson et al. |
| 2014/0005197 A1 | 1/2014 | Charifson et al. |
| 2014/0113950 A1 | 4/2014 | Khvorova et al. |
| 2014/0155387 A1 | 6/2014 | No et al. |
| 2014/0288148 A1 | 9/2014 | Biegelman et al. |
| 2014/0296486 A1 | 10/2014 | Gao et al. |
| 2014/0315974 A1 | 10/2014 | Khvorova et al. |
| 2014/0364482 A1 | 12/2014 | Khvorova et al. |
| 2015/0025122 A1 | 1/2015 | Smith |
| 2015/0190525 A1 | 7/2015 | Tatro |
| 2015/0209441 A1 | 7/2015 | Carell |
| 2015/0232840 A1 | 8/2015 | Aronin et al. |
| 2015/0247142 A1 | 9/2015 | Esau et al. |
| 2015/0267200 A1 | 9/2015 | McSwiggen et al. |
| 2015/0315584 A1 | 11/2015 | Macdonald et al. |
| 2016/0017323 A1 | 1/2016 | Prakash et al. |
| 2016/0115482 A1 | 4/2016 | Libertine et al. |
| 2016/0115484 A1 | 4/2016 | Woolf et al. |
| 2016/0130578 A1 | 5/2016 | Khvorova et al. |
| 2016/0130583 A1 | 5/2016 | Yokota et al. |
| 2016/0244765 A1 | 8/2016 | Khvorova et al. |
| 2016/0281148 A1 | 9/2016 | Greenlee et al. |
| 2016/0319278 A1 | 11/2016 | Khvorova et al. |
| 2016/0355808 A1 | 12/2016 | Khvorova et al. |
| 2016/0355826 A1 | 12/2016 | Khvorova et al. |
| 2016/0376598 A1 | 12/2016 | Lee et al. |
| 2017/0009239 A1 | 1/2017 | Khvorova et al. |
| 2017/0009304 A1 | 1/2017 | Zhou |
| 2017/0037456 A1 | 2/2017 | Kokoris et al. |
| 2017/0043024 A1 | 2/2017 | Khvorova et al. |
| 2017/0043204 A1 | 2/2017 | James |
| 2017/0051283 A1 | 2/2017 | Khvorova |
| 2017/0051286 A1 | 2/2017 | Smith |
| 2017/0067056 A1 | 3/2017 | Khvorova et al. |
| 2017/0183655 A1 | 6/2017 | Grabcysk et al. |
| 2017/0189541 A1 | 7/2017 | Foster |
| 2017/0281795 A1 | 10/2017 | Geall |
| 2017/0312367 A1 | 11/2017 | Khvorova et al. |
| 2017/0327524 A1 | 11/2017 | Nanna et al. |
| 2017/0369882 A1 | 12/2017 | Khvorova et al. |
| 2018/0023082 A1 | 1/2018 | Stanek et al. |
| 2018/0087052 A1 | 3/2018 | Hung et al. |
| 2018/0094263 A1 | 4/2018 | Khvorova et al. |
| 2018/0179546 A1 | 6/2018 | Khvorova et al. |
| 2018/0251764 A1 | 9/2018 | Albaek et al. |
| 2018/0264105 A1 * | 9/2018 | Kugimiya ............ A61K 39/104 |
| 2019/0002880 A1 | 1/2019 | Woolf et al. |
| 2019/0024082 A1 | 1/2019 | Khvorova et al. |
| 2019/0144860 A1 | 5/2019 | Konstantinova et al. |
| 2019/0185855 A1 | 6/2019 | Khvorova et al. |
| 2019/0225965 A1 | 7/2019 | Khvorova et al. |
| 2019/0247507 A1 | 8/2019 | Khvorova et al. |
| 2020/0087663 A1 | 3/2020 | Aronin |
| 2020/0095580 A1 | 3/2020 | Hauptmann et al. |
| 2020/0123543 A1 | 4/2020 | Khvorova et al. |
| 2020/0165618 A1 | 5/2020 | Khvorova et al. |
| 2020/0270605 A1 | 8/2020 | Khvorova et al. |
| 2020/0308578 A1 | 10/2020 | Woolf et al. |
| 2020/0308584 A1 | 10/2020 | Khvorova et al. |
| 2020/0339983 A1 | 10/2020 | Khvorova et al. |
| 2020/0362341 A1 | 11/2020 | Khvorova |

(56) References Cited

U.S. PATENT DOCUMENTS

| | | |
|---|---|---|
| 2020/0385737 A1 | 12/2020 | Khvorova |
| 2021/0024926 A1 | 1/2021 | Khvorova et al. |
| 2021/0071117 A9 | 3/2021 | Khvorova et al. |
| 2021/0071177 A1 | 3/2021 | Khvorova |
| 2021/0085793 A1 | 3/2021 | Khvorova et al. |
| 2021/0115442 A1 | 4/2021 | Khvorova et al. |
| 2021/0139901 A1 | 5/2021 | Khvorova et al. |
| 2021/0317460 A1 | 10/2021 | Khvorova et al. |
| 2021/0340535 A1 | 11/2021 | Khvorova |
| 2021/0355491 A1 | 11/2021 | Khvorova et al. |
| 2021/0363523 A1 | 11/2021 | Khvorova et al. |
| 2022/0010309 A1 | 1/2022 | Khvorova et al. |
| 2022/0042015 A1 | 2/2022 | Khvorova et al. |
| 2022/0090069 A1 | 3/2022 | Khvorova et al. |
| 2022/0228141 A1 | 7/2022 | Khvorova et al. |
| 2022/0251554 A1 | 8/2022 | Khvorova et al. |
| 2022/0251555 A1 | 8/2022 | Khvorova et al. |
| 2022/0364100 A1 | 11/2022 | Khvorova et al. |
| 2023/0021431 A1 | 1/2023 | Khvorova |
| 2023/0061751 A1 | 3/2023 | Khvorova et al. |
| 2023/0078622 A1 | 3/2023 | Khvorova et al. |
| 2023/0193281 A1 | 6/2023 | Khvorova et al. |
| 2023/0313198 A1 | 10/2023 | Khvorova et al. |
| 2023/0340475 A1 | 10/2023 | Khvorova et al. |
| 2023/0348907 A1 | 11/2023 | Khvorova et al. |
| 2023/0392146 A1 | 12/2023 | Khvorova et al. |
| 2023/0416735 A1 | 12/2023 | Khvorova et al. |
| 2024/0067967 A1 | 2/2024 | Khvorova et al. |
| 2024/0084297 A1 | 3/2024 | Khvorova et al. |
| 2024/0132888 A1 | 4/2024 | Khvorova et al. |
| 2024/0132892 A1 | 4/2024 | Khvorova et al. |

FOREIGN PATENT DOCUMENTS

| | | | |
|---|---|---|---|
| CN | 104884618 A | 11/2015 | |
| CN | 105194689 A | 12/2015 | |
| EP | 1752536 A1 | 2/2007 | |
| EP | 2407539 A1 | 1/2012 | |
| EP | 2601204 A2 | 6/2013 | |
| EP | 2853597 A1 | 4/2015 | |
| EP | 3277811 A1 | 2/2018 | |
| EP | 3277814 A1 | 2/2018 | |
| EP | 3277815 A1 | 2/2018 | |
| EP | 3408391 A1 | 12/2018 | |
| EP | 3550021 A1 | 10/2019 | |
| EP | 3642341 A1 | 4/2020 | |
| EP | 3929293 A2 | 12/2021 | |
| EP | 3946369 A2 | 2/2022 | |
| EP | 4126040 A2 | 2/2023 | |
| JP | H06-41183 A | 2/1994 | |
| JP | H6-504680 A | 6/1994 | |
| JP | 2001-501614 A | 2/2001 | |
| JP | 2009-504782 A | 2/2009 | |
| JP | 2010-506598 A | 3/2010 | |
| JP | 2012-502657 A | 2/2012 | |
| JP | 2013-049714 A | 3/2013 | |
| JP | 2015-061534 A | 4/2015 | |
| JP | 2016-171815 A | 9/2016 | |
| JP | 2016-526529 A | 9/2016 | |
| JP | 2018-516091 A | 6/2018 | |
| WO | WO 1992/013869 A1 | 8/1992 | |
| WO | WO 1993/009239 A1 | 5/1993 | |
| WO | WO 1993/024641 A2 | 12/1993 | |
| WO | WO 1994/022890 A1 | 10/1994 | |
| WO | WO 1996/003500 A1 | 2/1996 | |
| WO | WO 1998/013526 A1 | 4/1998 | |
| WO | WO 2003/029459 A2 | 4/2003 | |
| WO | WO 2004/008946 A2 | 1/2004 | |
| WO | WO 2004/013280 A2 | 2/2004 | |
| WO | WO 2004/044136 A2 | 5/2004 | |
| WO | WO 2004/061081 A2 | 7/2004 | |
| WO | WO 2004/108956 A1 | 12/2004 | |
| WO | WO 2005/078095 A1 | 8/2005 | |
| WO | WO 2006/019430 A2 | 2/2006 | |
| WO | WO 2007/022470 A2 | 2/2007 | |
| WO | WO 2007/022506 A2 | 2/2007 | |
| WO | WO 2007/051045 A2 | 5/2007 | |
| WO | WO 2007/056153 A2 | 5/2007 | |
| WO | WO 2007/091269 A2 | 8/2007 | |
| WO | WO 2007/094218 A1 | 8/2007 | |
| WO | WO 2007/112414 A2 | 10/2007 | |
| WO | WO 2008/005562 A2 | 1/2008 | |
| WO | WO 2008/049078 A1 | 4/2008 | |
| WO | WO 2008/070477 A2 | 6/2008 | |
| WO | WO 2008/154482 A2 | 12/2008 | |
| WO | WO 2008/154482 A3 | 12/2008 | |
| WO | WO 2009/002944 A1 | 12/2008 | |
| WO | WO 2009/054551 A2 | 4/2009 | |
| WO | WO 2009/099991 A2 | 8/2009 | |
| WO | WO 2009/102427 A2 | 8/2009 | |
| WO | WO 2010/008582 A2 | 1/2010 | |
| WO | WO 2010/011346 A1 | 1/2010 | |
| WO | WO 2010/033246 A1 | 3/2010 | |
| WO | WO 2010/033247 A2 | 3/2010 | |
| WO | WO 2010/033248 A2 | 3/2010 | |
| WO | WO 2010/048352 A2 | 4/2010 | |
| WO | WO 2010/048585 A2 | 4/2010 | |
| WO | WO 2010/059226 A2 | 5/2010 | |
| WO | WO 2010/078536 A1 | 7/2010 | |
| WO | WO 2010/090762 A1 | 8/2010 | |
| WO | WO 2010/111503 A2 | 9/2010 | |
| WO | WO 2010/118263 A1 | 10/2010 | |
| WO | WO 2011/097643 A1 | 8/2011 | |
| WO | WO 2011/109698 A1 | 9/2011 | |
| WO | WO 2011/119852 A1 | 9/2011 | |
| WO | WO 2011/119871 A1 | 9/2011 | |
| WO | WO 2011/119887 A1 | 9/2011 | |
| WO | WO 2011/125943 A1 | 10/2011 | |
| WO | WO 2011/139702 A2 | 11/2011 | |
| WO | WO 2011/158924 A1 | 12/2011 | |
| WO | WO 2012/005898 A2 | 1/2012 | |
| WO | WO 2012/037254 A1 | 3/2012 | |
| WO | WO 2012/058210 A1 | 5/2012 | |
| WO | WO 2012/078637 A2 | 6/2012 | |
| WO | WO 2012/118911 A1 | 9/2012 | |
| WO | WO 2012/131365 A1 | 10/2012 | |
| WO | WO 2012/177906 A1 | 12/2012 | |
| WO | WO 2013/165816 A2 | 11/2013 | |
| WO | WO 2014/009429 A1 | 1/2014 | |
| WO | WO 2014/043544 A1 | 3/2014 | |
| WO | WO 2014/076195 A1 | 5/2014 | |
| WO | WO 2014/089313 A1 | 6/2014 | |
| WO | WO 2014/201306 A1 | 12/2014 | |
| WO | WO 2014/203518 A1 | 12/2014 | |
| WO | WO 2015/025122 A1 | 2/2015 | |
| WO | WO 2015/057847 A1 | 4/2015 | |
| WO | WO 2015/113004 A2 | 7/2015 | |
| WO | WO 2015/161184 A1 | 10/2015 | |
| WO | WO 2015/200078 A1 | 12/2015 | |
| WO | WO 2016/028649 A1 | 2/2016 | |
| WO | WO 2016/077321 A1 | 5/2016 | |
| WO | WO 2016/077349 A1 | 5/2016 | |
| WO | WO 2016/083623 A1 | 6/2016 | |
| WO | WO 2016/149331 A2 | 9/2016 | |
| WO | WO 2016/161374 A1 | 10/2016 | |
| WO | WO 2016/161378 A1 | 10/2016 | |
| WO | WO 2016/161388 A1 | 10/2016 | |
| WO | WO 2016/164866 A1 | 10/2016 | |
| WO | WO 2016/205410 A2 | 12/2016 | |
| WO | WO 2017/015555 A1 | 1/2017 | |
| WO | WO 2017/024239 A1 | 2/2017 | |
| WO | WO 2017/030973 A1 | 2/2017 | |
| WO | WO 2017/062862 A2 | 4/2017 | |
| WO | WO 2017/132669 A1 | 8/2017 | |
| WO | WO 2017/174572 A1 | 10/2017 | |
| WO | WO 2018/031933 A2 | 2/2018 | |
| WO | WO 2018/041973 A1 | 3/2018 | |
| WO | WO 2018/185241 A1 | 10/2018 | |
| WO | WO 2018/223056 A1 | 12/2018 | |
| WO | WO 2018/237245 A1 | 12/2018 | |
| WO | WO 2019/075418 A1 | 4/2019 | |
| WO | WO 2019/075419 A1 | 4/2019 | |
| WO | WO-2019099949 A1 * | 5/2019 | ........... A61K 31/192 |
| WO | WO 2019/217459 A1 | 11/2019 | |

(56) References Cited

FOREIGN PATENT DOCUMENTS

| | | | | |
|---|---|---|---|---|
| WO | WO-2019232255 A1 * | 12/2019 | ......... | A61K 31/7052 |
| WO | WO 2020/033899 A1 | 2/2020 | | |
| WO | WO 2020/041769 A1 | 2/2020 | | |
| WO | WO 2020/150636 A1 | 7/2020 | | |
| WO | WO 2020/198509 A2 | 10/2020 | | |
| WO | WO 2021/216556 A2 | 10/2021 | | |
| WO | WO 2021/195533 A2 | 11/2021 | | |
| WO | WO 2021/242883 A1 | 12/2021 | | |

OTHER PUBLICATIONS

Miller and Gardiner. 2010. Adaptable Synthesis of C-Glycosidic Multivalent Carbohydrates and Succinamide-Linked Derivatization. Org. Lett 12(22):5262-5265 (Year: 2010).*
Osborn et al. 2018. Hydrophobicity drives the systemic distribution of lipid-conjugated siRNAs via lipid transport pathways. BioRxiv posted Mar. 23, 2018 (Year: 2018).*
U.S. Appl. No. 18/375,206, filed Sep. 2023.*
U.S. Appl. No. 18/446,929, filed Aug. 2023.*
Akinc et al., A Combinatorial Library of Lipid-like Materials for Delivery of RNAi Therapeutics, Nature Biotechnology, vol. 26, No. 5, 20 Pages, May 2008.
Allerson et al., Fully 2'-Modified Oligonucleotide Duplexes with Improved in Vitro Potency and Stability Compared to Unmodified Small Interfering RNA, Journal of Medicinal Chemistry, vol. 48, No. 4, pp. 901-904, Jan. 20, 2005.
Alterman et al., Hydrophobically Modified siRNAs Silence Huntingtin mRNA in Primary Neurons and Mouse Brain, Molecular Therapy-Nucleic Acids, vol. 4, pp. e266, Dec. 1, 2015.
Alvarez-Erviti et al., Delivery of siRNA to the Mouse Brain by Systemic Injection of Targeted Exosomes, Nature Biotechnology, vol. 29, No. 4, pp. 341-345, Apr. 2011.
Atwell et al., Stable Heterodimers From Remodeling the Domain Interface of a Homodimer Using a Phage Display Library, Journal of Molecular Biology, vol. 270, Issue 1, pp. 26-35, Jul. 4, 1997.
Biscans et al., Diverse Lipid Conjugates for Functional Extra-Hepatic siRNA Delivery in Vivo, Nucleic Acids Research, vol. 47, No. 3, pp. 1082-1096, Dec. 14, 2018.
Braasch et al., RNA Interference in Mammalian Cells by Chemically-Modified RNA, Biochemistry, vol. 42, No. 26, pp. 7967-7975, Jun. 11, 2003.
Chen et al., Influence of Particle Size on the in Vivo Potency of Lipid Nanoparticle Formulations of siRNA, Journal of Controlled Release, vol. 235, pp. 236-244, Aug. 10, 2016.
Coles et al., A High-Throughput Method for Direct Detection of Therapeutic Oligonucleotide-Induced Gene Silencing In Vivo, Nucleic Acid Therapeutics, vol. 26, Issue 2, pp. 86-92, Apr. 11, 2016.
Dahlman et al., In Vivo Endothelial siRNA Delivery using Polymeric Nanoparticles with Low Molecular Weight, Nature Nanotechnology, vol. 9, No. 8, 17 Pages, Aug. 2014.
Egusquiaguirre et al., Nanoparticle Delivery Systems for Cancer Therapy: Advances in Clinical and Preclinical Research, Clinical and Translational Oncology, vol. 14, Issue 2, pp. 83-93, Feb. 2012.
El Andaloussi et al., Exosome-Mediated Delivery of siRNA In Vitro and In Vivo, Nature Protocols, vol. 7, No. 12, pp. 2112-2126, Nov. 15, 2012.
El Andaloussi et al., Exosomes for Targeted siRNA Delivery Across Biological Barriers, Advanced Drug Delivery Reviews, vol. 65, Issue 3, pp. 391-397, Mar. 2013.
El Andaloussi et al., Extracellular Vesicles: Biology and Emerging Therapeutic Opportunities, Nature Reviews Drug Discovery, vol. 12, No. 5, pp. 347-357, Apr. 15, 2013.
Elmen et al., Locked Nucleic Acid (LNA) Mediated Improvements in siRNA Stability and Functionality, Nucleic Acids Research, vol. 33, Issue 1, pp. 439-447, Jan. 14, 2005.
Frank et al., Structural Basis for 5'-Nucleotide Base-specific Recognition of Guide RNA by Human AGO2, Nature, vol. 465, pp. 818-822, Jun. 2010.

Geary et al., Pharmacokinetics, Biodistribution and Cell Uptake of Antisense Oligonucleotides, Advanced Drug Delivery Reviews, vol. 87, pp. 46-51, Jun. 29, 2015.
Geary, Antisense Oligonucleotide Pharmacokinetics and Metabolism, Expert Opinion on Drug Metabolism & Toxicology, vol. 5, pp. 381-391, Apr. 1, 2009.
Godinho et al., Pharmacokinetic Profiling of Conjugated Therapeutic Oligonucleotides: A High-Throughput Method based upon Serial Blood Microsampling Coupled to Peptide Nucleic Acid Hybridization Assay, Nucleic Acid Therapeutics, vol. 27, pp. 323-334, Dec. 1, 2017.
Goodson et al., Dental Applications, Medical Applications of Controlled Release, vol. 2, pp. 115-138, 1984.
Hammerling et al., Monoclonal Antibodies and T-Cell Hybridomas, Research Monographs in Immunology, vol. 3, pp. 563-681, 1981.
Haraszti et al., 5'-Vinylphosphonate improves tissue accumulation and efficacy of conjugated siRNAs in vivo, Nucleic Acids Research, vol. 45, No. 13, pp. 7581-7592, Jul. 27, 2017.
Harborth et al., Sequence, Chemical, and Structural Variation of Small Interfering RNAs and Short Hairpin RNAs and the Effect on Mammalian Gene Silencing, Antisense and Nucleic Acid Drug Development, vol. 13, pp. 83-105, Apr. 1, 2003.
Hassler et al., Comparison of Partially and Fully Chemically-Modified siRNA in Conjugate-Mediated Delivery in Vivo, Nucleic Acids Research, vol. 46, No. 5, pp. 2185-2196, Mar. 16, 2018.
Herdewijn, Heterocyclic Modifications of Oligonucleotides and Antisense Technology, Antisense and Nucleic Acid Drug Development, vol. 10, Issue 4, pp. 297-310, Jul. 8, 2004.
Huang, Preclinical and Clinical Advances of GalNAc-Decorated Nucleic Acid Therapeutics, Molecular Therapy—Nucleic Acids, vol. 6,, pp. 116-132, Mar. 17, 2017.
Jackson et al., Position-Specific Chemical Modification of siRNAs Reduces "Off-Target" Transcript Silencing, RNA, vol. 12, No. 7, pp. 1197-1205, May 8, 2006.
Karaki et al., Lipid-Oligonucleotide Conjugates Improve Cellular Uptake and Efficiency of TCTP-Antisense in Castration-Resistant Prostate Cancer, Journal of Controlled Release, vol. 258, pp. 1-9, Jul. 28, 2017.
Karlin et al., Applications and Statistics for Multiple High-Scoring Segments in Molecular Sequences, Proceedings of the National Academy of Sciences of the USA, vol. 90, pp. 5873-5877, Jun. 1993.
Karlin et al., Methods for Assessing the Statistical Significance of Molecular Sequence Features by Using General Scoring Schemes, Proceedings of the National Academy of science of the USA, vol. 87, No. 6, pp. 2264-2268, Mar. 1990.
Khan et al., Silencing Myostatin using Cholesterol-Conjugated siRNAs Induces Muscle Growth, Molecular Therapy, Nucleic Acids, vol. 5, 9 Pages, Jan. 1, 2016.
Khvorova, Oligonucleotide Therapeutics—A New Class of Cholesterol-Lowering Drugs, The New England Journal of Medicine, vol. 376, No. 1, pp. 4-7, Jan. 5, 2017.
Lee et al., Recent Developments in Nanoparticle-Based siRNA Delivery for Cancer Therapy, BioMed Research International, vol. 2013, Article ID 782041, 10 pages, May 30, 2013.
Lima et al., Single-Stranded siRNAs Activate RNAi in Animals, Cell, vol. 150, Issue 5, pp. 883-894, Aug. 31, 2012.
Liu et al., Snapshot PK: A Rapid Rodent in Vivo Preclinical Screening Approach, Drug Discovery Today, vol. 13, No. 7-8, pp. 360-367, Apr. 1, 2008.
Ly et al., Visualization of Self-Delivering Hydrophobically Modified siRNA Cellular Internalization, Nucleic Acids Research, vol. 45, pp. 15-25, Nov. 29, 2016.
Ma et al., Structural Basis for 5'-End-Specific Recognition of Guide RNA by the A. Fulgidus Piwi Protein, Nature, vol. 434, No. 7033, pp. 666-670, Mar. 31, 2005.
Matsuda et al., siRNA Conjugates Carrying Sequentially Assembled Trivalent N-Acetylgalactosamine Linked Through Nucleosides Elicit Robust Gene Silencing In Vivo in Hepatocytes, ACS Chemical Biology, vol. 10, No. 5, pp. 1181-1187, Mar. 2, 2015.
Morrissey et al., Activity of Stabilized Short Interfering RNA in a Mouse Model of Hepatitis B Virus Replication, Hepatology, vol. 41, No. 6, pp. 1349-1356, Jun. 2005.

(56) References Cited

OTHER PUBLICATIONS

Nair et al., Multivalent N-Acetylgalactosamine-Conjugated siRNA Localizes in Hepatocytes and Elicits Robust RNAi-Mediated Gene Silencing, Journal of the American Chemical Society, vol. 136, No. 49, pp. 16958-16961, Dec. 10, 2014.
Nallagatla et al., Nucleoside Modifications Modulate Activation of the Protein Kinase PKR in an RNA Structure-Specific Manner, RNA, vol. 14, pp. 1201-1213, Jun. 1, 2008.
Nikan et al., Docosahexaenoic Acid Conjugation Enhances Distribution and Safety of siRNA upon Local Administration in Mouse Brain, Molecular Therapy—Nucleic Acids, vol. 5, No. 8, pp. 1-11, Aug. 9, 2016.
Nikan et al., Synthesis and Evaluation of Parenchymal Retention and Efficacy of a Metabolically Stable, O-Phosphocholine-N-Docosahexaenoyl-L-serine siRNA Conjugate in Mouse Brain, Bioconjugate Chemistry, vol. 28, No. 6, 21 Pages, Jun. 21, 2017.
Nishina et al., Efficient In Vivo Delivery of siRNA to the Liver by Conjugation of a-Tocopherol, Molecular Therapy, vol. 16, No. 4, pp. 734-740, Apr. 2008.
Oberbauer et al., Renal Uptake of an 18-mer Phosphorothioate Oligonucleotide, Kidney International, vol. 48, pp. 1226-1232, 1995.
Osborn et al., Hydrophobicity Drives the Systemic Distribution of Lipid-Conjugated siRNAs Via Lipid Transport Pathways, Nucleic Acids Research, vol. 47, No. 3, pp. 1070-1081, Dec. 8, 2018.
Osborn et al., Improving siRNA Delivery In Vivo Through Lipid Conjugation, Nucleic Acid Therapeutics, vol. 28, No. 3, pp. 128-136, May 10, 2018.
Petersen et al., LNA: A Versatile Tool for Therapeutics and Genomics, Trends in Biotechnology, vol. 21, Issue 2, pp. 74-81, Feb. 2003.
Pokholenko et al., Lipid Oligonucleotide Conjugates as Responsive Nanomaterials for Drug Delivery, Journal of Materials Chemistry B, vol. 1, 6 Pages, 2013.
Prakash et al., Targeted Delivery of Antisense Oligonucleotides to Hepatocytes Using Triantennary N-Acetyl Galactosamine Improves Potency 10-Fold in Mice, Nucleic Acids Research, vol. 42, Issue 13, pp. 8796-8807, Jul. 29, 2014.
Rajeev et al., Hepatocyte-Specific Delivery of Sirnas Conjugated to Novel Non-Nucleosidic Trivalent N-Acetylgalactosamine Elicits Robust Gene Silencing in Vivo, ChemBioChem, vol. 16, pp. 903-908, Apr. 13, 2015.
Reed et al., Forty Mouse Strain Survey of Body Composition, Physiology & Behavior, vol. 91, No. 5, 15 Pages, Aug. 15, 2007.
Sarett et al., Lipophilic siRNA Targets Albumin in Situ and Promotes Bioavailability, tumor Penetration, and Carrier-Free Gene Silencing, Proceedings of the National Academy of Sciences, vol. 114, pp. E6490-E6497, Jul. 24, 2017.
Scherman et al., Genetic Pharmacology: Progresses in siRNA Delivery and Therapeutic Applications, Gene Therapy, vol. 24, pp. 151-156, Mar. 2017.
Smith et al., Reversed-Phase High Performance Liquid Chromatography of Phosphatidylcholine: A Simple Method for Determining Relative Hydrophobic Interaction of Various Molecular Species, Journal of Lipid Research, vol. 22, pp. 697-704, May 1, 1981.
Solano et al., Toxicological and Pharmacokinetic Properties of QPI-1007, a Chemically Modified Synthetic siRNA Targeting Caspase 2 mRNA, Following Intravitreal Injection, Nucleic Acid Therapeutics, vol. 24, pp. 258-266, Aug. 1, 2014.
Soutschek et al., Therapeutic Silencing of an Endogenous Gene by Systemic Administration of Modified siRNAs, Nature, vol. 432, No. 7014, pp. 173-178, Nov. 11, 2004.
Suhr et al., Efficacy and Safety of Patisiran for Familial Amyloidotic Polyneuropathy: A Phase II Multi-Dose Study, Orphanet Journal of Rare Diseases, vol. 10, pp. 1-9, Dec. 1, 2015.
Taniguchi et al., Plasmodium Berghei ANKA Causes Intestinal Malaria Associated with Dysbiosis, Scientific Reports, vol. 5, pp. 1-12, Oct. 27, 2015.
Tanowitz et al., Asialoglycoprotein Receptor 1 Mediates Productive Uptake of N-Acetylgalactosamine-Conjugated and Unconjugated Phosphorothioate Antisense Oligonucleotides into Liver Hepatocytes, Nucleic Acids Research, vol. 45, No. 21, pp. 12388-12400, Dec. 1, 2017.
Thompson et al., Toxicological and Pharmacokinetic Properties of Chemically Modified siRNAs Targeting p53 RNA Following Intravenous Administration, Nucleic Acid Therapeutics, vol. 22, No. 4, pp. 255-264, Aug. 1, 2012.
Wang et al., Nanoparticle-Based Delivery System for Application of siRNA In Vivo, Current Drug Metabolism, vol. 11, No. 2, pp. 182-196, 2010.
Wanke et al., Overgrowth of Skin in Growth Hormone Transgenic Mice Depends on the Presence of Male Gonads, Journal of Investigative Dermatology, vol. 113, pp. 967-971, Dec. 1, 1999.
Whitehead et al., Degradable Lipid Nanoparticles with Predictable in Vivo siRNA Delivery Activity, Nature Communications, vol. 5, pp. 1-10, Jun. 27, 2014.
Wolfrum et al., Mechanisms and Optimization of in Vivodelivery of Lipophilic siRNAs, Nature Biotechnology, vol. 25, No. 10, pp. 1149-1157, Sep. 16, 2007.
Yuan et al., Recent Advances of siRNA Delivery by Nanoparticles, Expert Opinion on Drug Delivery vol. 8, Issue 4, pp. 521-536, Mar. 18, 2011.
Zhou et al., Nanoparticle-based Delivery of RNAi Therapeutics: Progress and Challenges, Pharmaceuticals, vol. 6, pp. 85-107, Jan. 2013.
Zimmermann et al., Clinical Proof of Concept for a Novel Hepatocyte-Targeting GalNAc-siRNA Conjugate, Molecular Therapy, vol. 25, Issue 1, pp. 71-78, Jan. 4, 2017.
Alexopoulou, et al., Recognition of Double-Stranded RNA and Activation of Nf-κb by Toll-like receptor 3, Nature, vol. 413, No. 6857, pp. 732-738, Oct. 18, 2001.
Alisky, et al., "Gene Therapy for Amyotrophic Lateral Sclerosis and Other Motor Neuron Diseases", Human Gene Therapy, vol. 11, Issue 17, pp. 2315-2329, Nov. 20, 2000.
Alves, et al., Selectivity, Cooperativity, and Reciprocity in the Interactions between the δ-Opioid Receptor, Its Ligands, and G-proteins, Journal of Biological Chemistry, vol. 279 Number 43, pp. 4673-44682, Aug. 17, 2004.
Amarzguioui, et al., "Tolerance for Mutations and Chemical Modifications in a siRNA", Nucleic Acids Research, Jan. 15, 2003, 31(2): 589-595.
Ambardekar et al., "The modification of siRNA with 3' cholesterol to increase nuclease protection and suppression of native mRNA by select siRNA polyplexes", Biomaterials, Elsevier, Amsterdam, NL, vol. 32, No. 5, pp. 1404-1411. (Nov. 2, 2010).
Ambros, et al., MicroRNAs and Other Tiny Endogenous RNAs in C. elegans, Current Biology, vol. 13, Issue 10, pp. 807-818, May 13, 2003.
Ameres, et al., Molecular Basis for Target RNA Recognition and Cleavage by Human RISC, Cell, vol. 130, Issue 1, pp. 101-112, Jul. 13, 2007.
Anderson, et al., Experimental Validation of the Importance of Seed Complement Frequency to siRNA Specificity, RNA, vol. 14, No. 5, pp. 853-861, Mar. 26, 2008.
Anderson, et al., Identifying siRNA-Induced Off-Targets by Microarray Analysis, Methods in Molecular Biology, vol. 442, pp. 45-63, 2008.
Aubuchon, et al., "Preeclampsia: Animal Models for a Human Cure", Proceedings of the National Academy of Sciences, vol. 108, No. 4, pp. 1197-1198, Jan. 25, 2011.
Aureli, et al., GM1 Ganglioside: Past Studies and Future Potential, Molecular Neurobiology, vol. 53, Issue 3, pp. 1824-1842, Apr. 2016.
Avino, et al., Branched RNA: A New Architecture for RNA Interference, Journal of Nucleic Acids, Article IC586935, 7 pages, Mar. 6, 2011.
Bagella, et al., Cloning of Murine CDK9/PITALRE and Its Tissue-Specific Expression in Development, Journal of cellular physiology, vol. 177, No. 2, pp. 206-213, Dec. 7, 1998.
Bartlett, et al., Can Metastatic Colorectal Cancer Be Cured?, Journal Oncology, Cancer Network, vol. 26, No. 3, pp. 266-275, Mar. 15, 2012.

(56) References Cited

OTHER PUBLICATIONS

Bartlett, et al., Insights Into The Kinetics of siRNA-Mediated Gene Silencing From Live-Cell and Live-Animal Bioluminescent Imaging, Nucleic Acids Research, vol. 34, Issue 1, pp. 322-333, Jan. 1, 2006.
Behlke, et al., Chemical Modification of siRNAs for In Vivo Use, Oligonucleotides, vol. 18, No. 4, pp. 305-320, Nov. 29, 2008.
Bell, et al., Liposomal Transfection Efficiency and Toxicity on Glioma Cell Lines: In Vitro and In Vitro Studies, Neuroreport, vol. 9, Issue 5, pp. 793-798, Mar. 30, 1998.
Billy, et al., Specific Interference With Gene Expression Induced by Long, Double-Stranded RNA in Mouse Embryonal Teratocarcinoma Cell Lines, Proceedings of the National Academy of Sciences, vol. 98, No. 25, pp. 14428-14433, Dec. 4, 2001.
Birmingham, et al., 3' UTR Seed Matches, But Not Overall Identity, Are Associated With RNAi Off-Targets, Nature Methods, vol. 3, No. 3, pp. 199-204, Feb. 17, 2006.
Birmingham, et al., A Protocol for Designing siRNAs With High Functionality and Specificity, Nature Protocols, vol. 2, No. 9, pp. 2068-2078, Aug. 23, 2007.
Boutla et al., "Short 5'-phosphorylated double-stranded RNAs induce RNA interference in *Drosophila*", Biology, 2001, 11: 1776-1780.
Brennecke, et al., Towards a Complete Description of the microRNA Complement of Animal Genomes, Genome Biology, vol. 4, No. 9, 3 Pages, Aug. 21, 2003.
Brummelkamp, et al., A System for Stable Expression of Short Interfering RNAs in Mammalian Cells, Science, vol. 296, Issue 5567, pp. 550-553, Apr. 19, 2002.
Burchard, et al., MicroRNA-Like Off-Target Transcript Regulation by siRNAs is Species Specific, RNA, vol. 15, No. 2, pp. 308-315, 2009.
Burke, et al., "Spiral Arterial Remodeling Is Not Essential for Normal Blood Pressure Regulation in Pregnant Mice", Hypertension, vol. 55, No. 3, pp. 729-737, Jan. 25, 2010.
Byrne, et al., Novel Hydrophobically Modified Asymmetric RNAi Compounds (sd-rxRNA) Demonstrate Robust Efficacy in the Eye, Journal of Ocular Pharmacology and Therapeutics, vol. 29, Issue 10, pp. 855-864, Dec. 3, 2013.
Calegari, et al., Tissue-Specific RNA Interference in Postimplantation Mouse Embryos With Endoribonuclease-Prepared Short Interfering RNA, Proceedings of the National Academy of Sciences, vol. 99, No. 22, pp. 14236-14240, Oct. 29, 2002.
Carter, "Handbook of Parvoviruses", ed., p. Tijsser, CRC Press, pp. 155-168, 1990.
Chang, et al., Enhanced intracellular delivery and multi-target gene silencing triggered by tripodal RNA Structure, The journal of gene Medicine, vol. 14, No. 2, pp. 138-146, Feb. 2012.
Chang, et al., Transgenic Animal Models for Study of the Pathogenesis of Huntington's Disease and Therapy, Drug design, development and therapy, vol. 9, pp. 2179-2188, Apr. 2015.
Charnock-Jones, et al., "Identification and Localization of Alternately Spliced mRNAs for Vascular Endothelial Growth Factor in Human Uterus and Estrogen Regulation in Endometrial Carcinoma Cell Lines", Biology of Reproduction, vol. 48, pp. 1120-1128, 1993.
Charrier, et al., Inhibition of SRGAP2 Function by Its Human-Specific Paralogs Induces Neoteny during Spine Maturation, Cell, vol. 149, Issue 4, pp. 923-935, May 11, 2012.
Chen et al., "Lipophilic siRNAs mediate efficient gene silencing in oligodendrocytes with direct CNC delivery", Journal of Controlled Release, Elsevier, vol. 144, pp. 227-232. (Feb. 17, 2010).
Chen et al., "Thermoresponsive polypeptides from pegylated poly-L-glutamates", Biomacromolecules 2011, 12: 2859-2863.
Chen, et al., "Gene Therapy for Brain Tumors: Regression of Experimental Gliomas by Adenovirus-Mediated Gene Transfer In Vivo", Proceedings of the National Academy of Sciences, vol. 91, No. 8, pp. 3054-3057, 1994.
Cheng, et al., Enhanced Hepatic Uptake and Bioactivity of Type α1(I) Collagen Gene Promoter-Specific Triplex-Forming Oligonucleotides after Conjugation with Cholesterol, Journal of Pharmacology and Experimental Therapeutics, vol. 370, Issue 2, pp. 797-805, Aug. 1, 2019.
Cheung, et al., Effects of All-Trans-Retinoic Acid on Human SH-SYSY Neuroblastoma as in Vitro Model in Neurotoxicity Research, Neurotoxicology, vol. 30, No. 1, pp. 127-135, Jan. 1, 2009.
Cho, et al., Vascular Endothelial Growth Factor Receptor 1 Morpholino Decreases Angiogenesis in a Murine Corneal Suture Model, Investigative ophthalmology & visual science, vol. 53, Issue 2, pp. 685-692, Feb. 2012.
Choe, et al., Crystal Structure of Human Toll-Like Receptor 3 (TLR3) Ectodomain, Science, vol. 309, Issue 5734, pp. 581-585, Jun. 16, 2005.
Chung et al., "Reducible siRNA Dimeric Conjugates for Efficient Cellular Uptake and Gene Silencing", Bioconjugate Chem., 2011, 22(2): 299-306.
Coelho, et al., Safety and Efficacy of RNAi Therapy for Transthyretin Amyloidosis, New England Journal of Medicine, vol. 369, No. 9, pp. 819-829, Aug. 29, 2013.
Cui, et al., "Role of Corin in Trophoblast Invasion and Uterine Spiral Artery Remodelling in Pregnancy", Nature, vol. 484, No. 7393, pp. 246-250, Mar. 21, 2012.
Damha et al. (1990) "An improved procedure for derivatization of controlled-pore glass beads for solid-phase oligonucleotide synthesis," Nucleic Acids Research, 18(13):3813-3821.
Dass, Crispin R., Cytotoxicity Issues Pertinent to Lipoplex-Mediated Gene Therapy In-Vivo, Journal of Pharmacy and Pharmacology, vol. 54, Issue 5, pp. 593-601, Feb. 18, 2010.
Davidson, et al., A Model System for In Vivo Gene Transfer Into the Central Nervous System Using an Adenoviral Vector, Nature Genetics, vol. 3, No. 3, pp. 219-223, Mar. 1, 1993.
Davidson, et al., Recombinant Adeno-Associated Virus Type 2, 4, and 5 Vectors: Transduction of Variant Cell Types And Regions in the Mammalian Central Nervous System, Proceedings of the National Academy of Sciences, vol. 97, No. 7, pp. 3428-3432, Mar. 28, 2000.
De Fougerolles, et al., "Interfering With Disease: a Progress Report on siRNA-based Therapeutics", Nature Reviews Drug Discovery, vol. 6, pp. 443-453, Jun. 2007.
De Marre et al., "Synthesis, characterization, and in vitro biodegradation of poly(ethylene glycol) modified poly [5N-(2-hydroxyethyl-L-glutamine]", J Bioact Compat Polym, 1996, 11: 85-99.
De Paula et al., "Hydrophobization and bioconjugation for enhanced siRNA delivery and targeting", RNA, Feb. 28, 2007, vol. 13, No. 4, pp. 431-456.
Deleavey, et al., The 5' Binding MID Domain of Human Argonaute2 Tolerates Chemically Modified Nucleotide Analogues, Nucleic acid therapeutics, vol. 23, No. 1, pp. 81-87, Feb. 7, 2013.
Difiglia, et al., Therapeutic Silencing of Mutant Huntingtin With siRNA Attenuates Striatal and Cortical Neuropathology and Behavioral Deficits, Proceedings of the National Academy of Sciences, vol. 104, No. 43, pp. 17204-17209, Oct. 23, 2007.
Dinusha, Differnce Between Sterol and Steroid, Home / Health / Medicine / Nutrients & Drugs, Aug. 4, 2011.
Doench, et al., siRNAs Can Function as miRNAs, Genes & Development, vol. 17, pp. 438-442, 2003.
Dohmen et al., "Defined Folate-PEG-siRNA Conjugates for Receptor-specific Gene Slicing", Molecular Therapy-Nucleic Acids, 2012, 1(1): e7.
Dufour, et al., Intrajugular Vein Delivery of AAV9-RNAi Prevents Neuropathological Changes and Weight Loss in Huntington's Disease Mice, Molecular Therapy, vol. 22, No. 4, pp. 797-810, Jan. 6, 2014.
Dyall, et al., Long-chain omega-3 fatty acids and the brain: a review of the independent and shared effects of EPA, DPA and DHA, Frontiers in Aging Neuroscience, vol. 7, p. 52, Apr. 21, 2015.
Eckstein, Phosphorothioate Oligodeoxynucleotides: What Is Their Origin and What Is Unique About Them?, Antisense and Nucleic Acid Drug Development, vol. 10, Issue 2, pp. 117-121, Jan. 30, 2009.
EMBL Database, WO 2005116204-A/113070: Double Strand Polynucleotides Generating RNA Interference, EBI Accession No. EM PAT:FW706544, XP055753619, , Apr. 18, 2011.

(56) References Cited

OTHER PUBLICATIONS

Eremina, et al., "Glomerular-Specific Alterations of VEGF-A Expression Lead to Distinct Congenital and Acquired Renal Diseases", Journal of Clinical Investigation, vol. 111, No. 5, pp. 707-716, Mar. 2003.
Eremina, et al., "VEGF Inhibition and Renal Thrombotic Microangiopathy", New England Journal of Medicine, vol. 358, No. 11, pp. 1129-1136, Mar. 13, 2008.
Evers, et al., Antisense Oligonucleotides in Therapy for Neurodegenerative Disorders, Advanced Drug Delivery Reviews, vol. 87, pp. 90-103, Jun. 29, 2015.
Extended European Search Report for European Patent Application No. 16837593.9, dated Mar. 20, 2019.
Extended European Search Report for European Patent Application No. 17745083.0, dated on Jul. 31, 2019.
Extended European Search Report for European Patent Application No. 17840367.1, dated Oct. 14, 2020.
Extended European Search Report for European Patent Application No. 18819571.3, dated May 14, 2021.
Extended European Search Report for European Patent Application No. 20164108.1, dated on Dec. 3, 2020.
Extended European Search Report for European Patent Application No. 20216265.7, dated Feb. 10, 2022.
Extended European Search Report for European Patent Application No. 21197881.2, dated Oct. 31, 2022.
Fan, et al., Endometrial VEGF Induces Placental sFLT1 And Leads to Pregnancy Complications, The Journal of clinical investigation, vol. 124, No. 11, pp. 4941-4952, Oct. 20, 2014.
Fattal, et al., Biodegradable Polyalkylcyanoacrylate Nanoparticles for the Delivery of Oligonucleotides, Journal of Controlled Release, vol. 53, pp. 137-143, May 1998.
Fedorov, et al., Off-Target Effects by siRNA Can Induce Toxic Phenotype, RNA, vol. 12, No. 7, pp. 1188-1196, May 2006.
Felber, et al., The Interactions of Amphiphilic Antisense Oligonucleotides With Serum Proteins and Their Effects on In Vitro Silencing Activity, Biomaterials, vol. 33, Issue 25, pp. 5955-5965, Sep. 2012.
Figueroa, et al., Neurorestorative Targets of Dietary Long-Chain Omega-3 Fatty Acids in Neurological Injury, Molecular Neurobiology, vol. 50, Issue 1, pp. 197-213, Aug. 2014.
Fisher, et al., Transduction With Recombinant Adeno-Associated Virus for Gene Therapy Is Limited by Leading-Strand Synthesis, Journal of virology, vol. 70, No. 1, pp. 520-532, Jan. 1996.
Franich, et al., AAV Vector-Mediated RNAi of Mutant Huntingtin Expression is Neuroprotective in a Novel Genetic Rat Model of Huntington's Disease, Molecular Therapy, vol. 16, Issue 5, pp. 947-956, Mar. 25, 2008.
Frazier, Antisense Oligonucleotide Therapies: The Promise and the Challenges from a Toxicologic Pathologist's Perspective, Toxicologic pathology, vol. 43, Issue 1, pp. 78-89, Nov. 9, 2014.
Frigg et al., Relationships between vitamin A and vitamin E in the chick, Int J Vitam Nutr Res., 1984, 54(2-3): 125-133.
Furuhashi et al., Expression of Low Density Lipoprotein Receptor Gene in Hjuman Placenta during Pregnancy, Molecular Endocrinology, 1989, 3: 1252-1256.
Gaglione, et al., Recent Progress in Chemically Modified siRNAs, Mini Reviews in Medicinal Chemistry, vol. 10, No. 7, pp. pp. 578-595, 2010.
Gavrilov et al. (Jun. 2012) "Therapeutic siRNA: principles, challenges, and strategies", Yale Journal of Biology and Medicine, 85:187-200.
Genbank, Mus Musculus Non-Coding RNA, Oocyte_Clustered_Small_RNA6599, Complete Sequence, GenBank Accession No. AB341398.1, May 24, 2008, 1 page.
Genbank, Rattus Norvegicus piRNApiR-182271, Complete Sequence, GenBank Accession No. DQ766949.1, Jul. 12, 2006, 1 Page.
Genbank, Signal Recognition Particle 54 kDa protein 2 [Perkinsus marinus ATCC 50983], NCBI Reference Sequence: XP_002784438.1, Apr. 30, 2010.
Gilany, et al., The Proteome of the Human Neuroblastoma Cell Line SH-SY5Y: An Enlarged Proteome, Biochimica et Biophysica Acta (BBA)—Proteins and Proteomics, vol. 1784, Issues 7-8, pp. 983-985, Jul.-Aug. 2008.
Gilbert, et al., "Hypertension Produced by Reduced Uterine Perfusion in Pregnant Rats Is Associated With Increased Soluble fms-like Tyrosine Kinase-1 Expression", Hypertension, vol. 50, No. 6, pp. 1142-1147, Oct. 8, 2007.
Gille, et al., "Analysis of Biological Effects and Signaling Properties of Flt-1 (VEGFR-1) and KDR (VEGFR-2)", Mechanisms of Signal Transduction, vol. 276, Issue 5, pp. 3222-3230, Feb. 2001.
Godard, et al., "Antisense Effects of Cholesterol-Oligodeoxynucleotide Conjugates Associated with Poly(alkylcyanoacrylate) Nanoparticles", European Journal of Biochemistry banner, vol. 232, pp. 404-410, 1995.
Grad, et al., Computational and Experimental Identification of C. elegans microRNAs, Molecular Cell, vol. 11, Issue 5, pp. 1253-1263, May 2003.
Gray, et al., Human Mutant Huntingtin with a Stable Polyglutamine Repeat Can Elicit Progressive and Selective Neuropathogenesis in BACHD Mice, Journal of Neuroscience, vol. 28, Issue 24, pp. 6182-6195, Jun. 11, 2008.
Griffiths-Jones, San, The microRNA Registry, Nucleic Acids Research, vol. 32, Issue Supplement 1, pp. D109-D111, Jan. 1, 2004.
Grimm, D, Asymmetry in siRNA Design, Gene Therapy, vol. 16, No. 7, pp. 827-829, Apr. 30, 2009.
Grimm, et al., Fatality In Mice Due to Oversaturation of Cellular MicroRNA/short Hairpin RNA Pathways, Nature, vol. 441, No. 7092, pp. 537-541, May 25, 2006.
Hamajima, et al., Intranasal Administration of HIV-DNA Vaccine Formulated with a Polymer, Carboxymethylcellulose, Augments Mucosal Antibody Production and Cell-Mediated Immune Response, Clinical Immunology and Immunopathology, vol. 88, Issue 2, pp. 205-210, Aug. 1998.
Heydarian, et al., Novel Splice Variants of sFlt1 are Upregulated in Preeclampsia, Placenta, vol. 30, Issue 3, pp. 250-255, Mar. 2009.
Heyer, et al., An Optimized Kit-Free Method for Making Strand-Specific Deep Sequencing Libraries From RNA Fragments, Nucleic Acids Research, vol. 43, Issue 1, pp. 1-14, Jan. 9, 2015.
Hirashima, et al., "Trophoblast Expression of Fms-like Tyrosine Kinase 1 Is Not Required for the Establishment of the Maternal-fetal Interface in the Mouse Placenta", Proceedings of the National Academy of Sciences of the United States of America, vol. 100, No. 26, pp. 15637-15642, Dec. 23, 2003.
Hodgson, et al., A YAC Mouse Model for Huntington's Disease with Full-Length Mutant Huntingtin, Cytoplasmic Toxicity, and Selective Striatal Neurodegeneration, Neuron, vol. 23, Issue 1, pp. 181-192, May 1999.
Hong et al., "Reducible Dimeric Conjugates of Small Internally Segment Interfering RNA for Efficient Gene Silencing", Macromolecular Bioscience, Jun. 2016, vol. 16, No. 10, pp. 1442-1449.
Hult, et al., Mutant Huntingtin Causes Metabolic Imbalance by Disruption of Hypothalamic Neurocircuits, Cell Metabolism, vol. 13, Issue 4, pp. 428-439, Apr. 6, 2011.
Hutvagner, et al., A microRNA in a Multiple-Turnover RNAi Enzyme Complex, Science, vol. 297, Issue 5589, pp. 2056-2060, Sep. 20, 2002.
Intapad, et al., "Reduced Uterine Perfusion Pressure Induces Hypertension in the Pregnant Mouse", American Journal of Physiology-Regulatory, Integrative and Comparative Physiology, vol. 307, Issue 11, pp. R1353-R1357, Dec. 2014.
International Search Report & Written Opinion Received for PCT Application No. PCT/US2019/046013, mailed on Jan. 9, 2020.
International Search Report & Written Opinion Received for PCT Application No. PCT/US2020/014181, mailed on Jun. 2, 2020.
International Search Report and Written Opinion in related PCT Application No. PCT/US2020/014146, mailed May 22, 2020.
International Search Report and Written Opinion received for PCT Patent Application No. PCT/US2016/025722, mailed on Aug. 12, 2016.
International Search Report and Written Opinion received for PCT Patent Application No. PCT/US2016/025731, mailed on Sep. 9, 2016.

(56) References Cited

OTHER PUBLICATIONS

International Search Report and Written Opinion received for PCT Patent Application No. PCT/US2016/025753, mailed on Sep. 14, 2016.
International Search Report and Written Opinion received for PCT Patent Application No. PCT/US2016/046810, mailed on Nov. 29, 2016.
International Search Report and Written Opinion received for PCT Patent Application No. PCT/US2017/015633, mailed on May 11, 2017.
International Search Report and Written Opinion received for PCT Patent Application No. PCT/US2018/038952, mailed on Sep. 24, 2018.
International Search Report and Written Opinion received for PCT Patent Application No. PCT/US2020/045487, mailed on Dec. 31, 2020.
International Search Report and Written Opinion received for PCT Patent Application No. PCT/US2021/013620, mailed on Apr. 26, 2021.
Iriyama et al., Hypoxia-independent up-regulation of placental HIF-1α gene expression contributes to the pathogenesis of preeclampsia, Hypertension, Jun. 2015, 65(6): 1307-1315, Supplemental Data.
Iriyama et al., Hypoxia-independent up-regulation of placental HIF-1α gene expression contributes to the pathogenesis of preeclampsia, Hypertension, Jun. 2015, 65(6): 1307-1315.
Iversen et al., "Optimized siRNA-PEG Conjugates for Extended Blood Circulation and Reduced Urine Excretion in Mice", Feb. 25, 2013, Theranostics 2013, vol. 3, Issue 3, pp. 201-209.
Jackson, et al., Recognizing and Avoiding siRNA Off-Target Effects for Target Identification and Therapeutic Application, Nature Reviews Drug Discovery, vol. 9, No. 1, pp. 57-67, Jan. 1, 2010.
Jacque, et al., Modulation of HIV-1 replication by RNA interference, Nature, vol. 418, No. 6896, pp. 435-438, Jun. 26, 2002.
Janssen, et al., Long-Chain Polyunsaturated Fatty Acids (LCPUFA) From Genesis to Senescence: The Influence of LCPUFA on Neural Development, Aging, and Neurodegeneration, Progress in Lipid Research, vol. 53, pp. 1-17, Jan. 2014.
Jebbink et al., "Expression of Placental FLT1 Transcript Variants Relates to Both Gestational Hypertensive Disease and Fetal Growth", Hypertension, Apr. 25, 2011, 58(1): 70-76.
Jin, et al., DARPP-32 to Quantify Intracerebral Hemorrhage-induced Neuronal Death in Basal Ganglia, Translational Stroke Research, vol. 4, No. 1, pp. 130-134, Feb. 1, 2013.
Jo, et al., Selection and Optimization of Asymmetric siRNA Targeting the Human c-MET Gene, Molecules and cells, vol. 32, No. 6, pp. 543-548, Dec. 31, 2011.
Judge, et al., Design of Noninflammatory Synthetic siRNA Mediating Potent Gene Silencing in Vivo, Molecular Therapy, vol. 13, Issue 3, pp. 494-505, Mar. 2006.
Jung et al., "Gene silencing efficiency of siRNA-PEG conjugates: Effect of PEGylation site and PEG molecular weight", Journal of Controlled Release, Mar. 4, 2010, vol. 144, No. 3, pp. 306-313.
Kamba, et al., "VEGF-dependent Plasticity of Fenestrated Capillaries in the Normal Adult Microvasculature", American Journal of Physiology-Heart and Circulatory Physiology, vol. 29, pp. H560-H576, Feb. 1, 2006.
Karra, et al., Transfection Techniques for Neuronal Cells, Journal of Neuroscience, vol. 30, No. 18, pp. 6171-6177, May 5, 2010.
Kenski et al. (2012) "siRNA-optimized Modifications for Enhanced In Vivo Activity," Mol. Ther. Nucleic Acids. 1:e5. pp. 1-8.
Khankin, et al., "Intravital High-frequency Ultrasonography to Evaluate Cardiovascular and Uteroplacental Blood Flow in Mouse Pregnancy", Pregnancy Hypertension: An International Journal of Women's Cardiovascular Health, vol. 2, pp. 84-92, 2012.
Khvorova, et al., Abstract IA27: Advances in Oligonucleotide Chemistry for the Treatment of Neurodegenerative Disorders and Brain Tumors, Cancer Research, vol. 76, Issue 6, Abstract IA27, Mar. 2016.
Khvorova, et al., Functional siRNAs and miRNAs Exhibit Strand Bias, Cell, vol. 115, Issue 2, pp. 209-216, Oct. 17, 2003.
Kim et al., "LHRH Receptor-Mediated Delivery of siRNA Using Polyelectrolyte Complex Micelles Self-Assembled from siRNA-PEG-LHRH Conjugate and PEI", Bioconjugate Chemistry, Oct. 14, 2008, vol. 19, No. 11, pp. 2156-2162.
Kim et al., "PEG conjugated VEGF siRNA for anti-angiogenic gene therapy", Journal of Controlled Release, Jun. 3, 2006, vol. 116, No. 2, pp. 123-129.
Kordasiewicz, et al., Sustained Therapeutic Reversal of Huntington's Disease by Transient Repression of Huntingtin Synthesis, Neuron, vol. 74, Issue 6, pp. 1031-1044, Jun. 21, 2012.
Kubo et al., "Lipid-Conjugated 27-Nucleotide Double-Stranded RNAs with Dicer-Substrate Potency enhance RNAi-Mediated Gene Silencing", Molecular Pharmaceutics, American Chemical Society, US, vol. 9, No. 5, pp. 1374-1382, DOI: 10.1021/MP2006278. (Apr. 11, 2012).
Kubo et al., "Palmitic Acid-Conjugated 21-Nucleotide siRNA Enhances Gene-Silencing Activity", Molecular Pharmaceutics, vol. 8, No. 6, pp. 2193-2203, DOI: 10.1021/mp200250f. (Oct. 10, 2011).
Kumar, et al., "Shielding of Lipid Nanoparticles for siRNA Delivery: Impact on Physicochemical Properties", Cytokine Induction, and Efficacy, Molecular Therapy-Nucleic Acids, vol. 3, e210, pp. 1-7, Nov. 18, 2014.
Lagos-Quintana, et al., Identification of Novel Genes Coding for Small Expressed RNAs, Science, vol. 294, Issue 5543, pp. 853-858, Oct. 26, 2001.
Lagos-Quintana, et al., Identification of Tissue-Specific MicroRNAs from Mouse, Current Biology, vol. 12, Issue 9, pp. 735-739, Apr. 30, 2002.
Lagos-Quintana, et al., New microRNAs From Mouse and Human, RNA, vol. 9, No. 2, pp. 175-179, 2003.
Lai, et al., Computational Identification of *Drosophila* microRNA Genes, Genome Biology, vol. 4, No. 7, pp. 1-20, Jun. 30, 2003.
Lam, et al., "A New Type of Synthetic Peptide Library for Identifying Ligand-Binding Activity", Nature, vol. 354, pp. 82-84, Nov. 7, 1991.
Lambert, et al., "Nanoparticulate Systems for the Delivery of Antisense Oligonucleotides", Advanced Drug Delivery Reviews, vol. 47, pp. 99-112, 2001.
Lan, et al., Neuroactive Steroid Actions at the GABAA Receptor, Hormones and Behavior, vol. 28, Issue 4, pp. 537-544, Dec. 1994.
Landis, et al., "A Call for Transparent Reporting to Optimize the Predictive Value of Preclinical Research", Nature, vol. 490, pp. 187-191, Oct. 10, 2012.
Lau, et al., An Abundant Class of Tiny RNAs with Probable Regulatory Roles in Caenorhabditis elegans, Science, vol. 294, Issue 5543, pp. 858-862, Oct. 26, 2001.
Lau, et al., Characterization of the piRNA Complex from Rat Testes, Science, vol. 313, Issue 5785, pp. 363-367, Jul. 21, 2006.
Laufer, et al., "Selected Strategies for the Delivery of siRNA In Vitro and In Vivo", RNA Technologies and Their Applications, 2010, pp. 29-58.
Lee et al., "Current preclinical small interfering RNA (siRNA)-based conjugate systems for RNA therapeutics", Advanced Drug Delivery Reviews, Oct. 27, 2015, vol. 104, pp. 78-92.
Lee, et al., An Extensive Class of Small RNAs in Caenorhabditis elegans, Science, vol. 294, Issue 5543, pp. 862-864, Oct. 26, 2001.
Lee, et al., Expression of Small Interfering RNAs Targeted Against HIV-1 rev Transcripts in Human Cells, Nature Biotechnology, vol. 20, No. 5, pp. 500-505, May 1, 2002.
Lee, et al., RNA Interference-Mediated Simultaneous Silencing of Four Genes Using Cross-Shaped RNA, Molecules and Cells, vol. 35, No. 4, pp. 320-326, Apr. 4, 2013.
Lee, et al., Small-interfering RNA (siRNA)-based functional micro- and nanostructures for efficient and selective gene silencing, Accounts of Chemical Research, vol. 45, No. 7, pp. 1014-1025, Jul. 17, 2012.
Levine, et al., "Circulating Angiogenic Factors and the Risk of Preeclampsia", The New England Journal of Medicine, vol. 350, pp. 672-683, 2004.
Li, et al., "Recombinant Vascular Endothelial Growth Factor 121 Attenuates Hypertension and Improves Kidney Damage in a Rat Model of Preeclampsia", Hypertension, vol. 50, pp. 686-692, 2007.

(56) References Cited

OTHER PUBLICATIONS

Li, et al., Distribution of 5-Hydroxymethylcytosine in Different Human Tissues, "SAGE—Hindawi Access to Research, Journal of Nucleic Acids, vol. 2011", pp. 1-7, 2011.

Li, et al., Huntington's Disease Gene (IT15) Is Widely Expressed In Human and Rat Tissues, Neuron, vol. 11, No. 5, pp. 985-993, Nov. 1993.

Lim, et al., The microRNAs of Caenorhabditis elegans, Genes & Development, vol. 17, No. 8, pp. 991-1008, 2003.

Lim, et al., Vertebrate MicroRNA Genes, Science, vol. 299, Issue 5612, p. 1540, Mar. 7, 2003.

Lopes, et al., Comparison Between Proliferative and Neuron-Like SH-SY5Y Cells as an In Vitro Model for Parkinson Disease Studies, Brain Research, vol. 1337, pp. 85-94, Jun. 14, 2010.

Lorenz, et al., Steroid And Lipid Conjugates of siRNAs to Enhance Cellular Uptake and Gene Silencing in Liver Cells, Bioorganic & Medicinal Chemistry Letters, vol. 14, Issue 19, pp. 4975-4977, Oct. 4, 2004.

Lundh, et al., Hypothalamic Expression of Mutant Huntingtin Contributes to the Development of Depressive-Like Behavior in the Bac Transgenic Mouse Model of Huntington's Disease, Human Molecular Genetics, vol. 22, Issue 17, pp. 3485-3497, Sep. 1, 2013.

Luo, et al., Photoreceptor Avascular Privilege Is Shielded by Soluble VEGF Receptor-1, Elife, vol. 2, pp. 1-22, Jun. 18, 2013.

Makris, et al., "Uteroplacental Ischemia Results in Proteinuric Hypertension and Elevated sFLT-1", Kidney International, vol. 71, Issue 1, pp. 977-984, May 2, 2007.

Maltepe, et al., "The Placenta: Transcriptional, Epigenetic, and Physiological Integration During Development", The Journal of Clinical Investigation, vol. 120, No. 4, pp. 1016-1025, Apr. 1, 2010.

Mangiarini, et al., Exon 1 of the HD Gene with an Expanded CAG Repeat Is Sufficient to Cause a Progressive Neurological Phenotype in Transgenic Mice, Cell, vol. 87, Issue 3, pp. 493-506, Nov. 1, 1996.

Mantha, et al., Rnai-Based Therapies For Huntington's Disease: Delivery Challenges and Opportunities, Therapeutic Delivery, vol. 3, No. 9, pp. 1061-1076, Aug. 29, 2012.

Marcus, et al., FedExosomes: Engineering Therapeutic Biological Nanoparticles that Truly Deliver, Pharmaceuticals, vol. 6, No. 5, pp. 659-680, Apr. 29, 2013.

Marques, et al., A Structural Basis for Discriminating Between Self and Nonself Double-Stranded Rnas in Mammalian Cells, Nature biotechnology, vol. 23, No. 11, pp. 1399-1405, 2005.

Masotti, et al., Comparison of Different Commercially Available Cationic Liposome—DNA Lipoplexes: Parameters Influencing Toxicity and Transfection Efficiency, Colloids and Surfaces B: Biointerfaces, vol. 68, Issue 2, pp. 136-144, Feb. 1, 2009.

Maynard, et al., "Excess Placental Soluble fms-like Tyrosine Kinase 1 (sFltl) may Contribute to Endothelial Dysfunction", Hypertension, and Proteinuria in Preeclampsia, The Journal of Clinical Investigation, vol. 111, pp. 649-658, 2003.

McCaffrey, et al., Gene Expression: RNA Interference in Adult Mice, Nature, vol. 418, No. 6893, pp. 38-39, Jul. 4, 2002.

McManus, et al., Gene Silencing Using Micro-RNA Designed Hairpins, RNA, vol. 8, Issue 6, pp. 842-850, Aug. 20, 2002.

Miyagishi, et al., U6 promoter-driven siRNAs With Four Uridine 3' Overhangs Efficiently Suppress Targeted Gene Expression In Mammalian Cells, Nature Biotechnology, vol. 20, No. 5, pp. 497-500, May 1, 2002.

Mok, et al., Multimeric small interfering ribonucleic acid for highly efficient sequence-specific gene silencing~, Nature Materials, vol. 9, pp. 272-278, Jan. 24, 2010.

Molitoris, et al., siRNA Targeted to p53 Attenuates Ischemic and Cisplatin-Induced Acute Kidney Injury, Journal of the American Society of Nephrology, vol. 20, Issue 8, pp. 1754-1764, Aug. 1, 2009.

Mourelatos, et al., miRNPs: A Novel Class of Ribonucleoproteins Containing Numerous microRNAs, Genes & Development, vol. 16, No. 6, pp. 720-728, 2002.

Mullen, et al., NeuN, A Neuronal Specific Nuclear Protein in Vertebrates, Development, vol. 116, No. 1, pp. 201-211, 1992.

Myers, et al., Optimal Alignments in Linear Space, Computer Applications in the Biosciences, vol. 4, No. 1, pp. 11-17, Mar. 1988.

Nagamatsu, et al., "Cytotrophoblasts Up-Regulate Soluble Fms-Like Tyrosine Kinase-1 Expression under Reduced Oxygen: An Implication for the Placental Vascular Development and the Pathophysiology of Preeclampsia", Endocrinology, vol. 145, Issue 11, pp. 4838-484, Nov. 1, 2004.

Neufeld, et al., "Similarities and Differences Between the Vascular Endothelial Growth Factor (VEGF) Splice Variants", Cancer and Metastasis Reviews, vol. 15, pp. 153-158, Jun. 1996.

Nielsen, et al., Sequence-Selective Recognition of DNA by Strand Displacement With a Thymine-Substituted Polyamide, Science, vol. 254, Issue 5037, pp. 1497-1500, Dec. 6, 1991.

Ohnishi, et al., "Enhancement of Allele Discrimination by Introduction of Nucleotide Mismatches into siRNA in Allele-Specific Gene Silencing by RNAi", Plos One, vol. 3, Issue 5, e2248, 9 Pages, May 2008.

Østergaard, et al., "Fluorinated Nucleotide Modifications Modulate Allele Selectivity of SNP-Targeting Antisense Oligonucleotides", Molecular Therapy Nucleic Acids, vol. 7, pp. 20-30, Jun. 2017.

Ouimet, et al., DARPP-32, A Dopamine- and Adenosine 3':5'-Monophosphate-Regulated Phosphoprotein Enriched in Dopamine-Innervated Brain Regions. III. Immunocytochemical Localization, Journal of Neuroscience, vol. 4, No. 1, pp. 111-124, Jan. 1, 1984.

Overhoff, et al., "Quantitative Detection of siRNA and Single-stranded Oligonucleotides: Relationship Between Uptake and Biological Activity of siRNA", Nucleic Acids Research, vol. 32, Issue 21, pp. 1-5, Dec. 2, 2004.

Owen, Morpholino-Mediated Increase in Soluble Flt-1 Expression Results in Decreased Ocular and Tumor Neovascularization, PLoS One, vol. 7, No. 3, pp. e33576, Mar. 15, 2012.

Paddison, et al., Short Hairpin RNAs (shRNAs) Induce Sequence-Specific Silencing in Mammalian Cells, Genes & Development, vol. 16, No. 8, pp. 948-958, 2002.

Partial European Search Report for European Patent Application No. 20216265.7, dated Nov. 10, 2021.

Partial European Search Report for European Patent Application No. 21197881.2, mailed Mar. 14, 2022.

Partial Supplementary European Search Report for European Patent Application No. 20741865.8, mailed Dec. 20, 2022.

Pasquinelli, et al., Conservation of The Sequence and Temporal Expression of let-7 Heterochronic Regulatory RNA, Nature, vol. 408, No. 6808, pp. 86-89., Nov. 2, 2000.

Paul, et al., Effective Expression of Small Interfering RNA in Human Cells, Nature Biotechnology, vol. 20, No. 5, pp. 505-508, May 1, 2002.

Peel, et al., Conjugation and Evaluation of Small Hydrophobic Molecules to Triazole-Linked siRNAs, ACS medicinal chemistry letters, vol. 6, No. 2, pp. 117-122, Dec. 4, 2014.

Pei, et al., Quantitative Evaluation of siRNA Delivery in Vivo, RNA, vol. 16, No. 12, pp. 2553-2563, Oct. 12, 2010.

Pfister, et al., "Five siRNAs Targeting Three SNPs in Huntingtin May Provide Therapy for Three-Quarters of Huntington's Disease Patients", Current Biology, vol. 19, No. 9, pp. 774-778., May 12, 2009.

Podbevsek et al., "Solution-state structure of a fully alternately 2'-F/2'-OMe modified 42-nt dimeric siRNA construct", Nucleic Acids Research, vol. 38, No. 20, pp. 7298-7307, DOI: 10.1093/nar/gkq621. (Jul. 12, 2010).

Posocco, et al., "Impact of siRNA Overhangs for Dendrimer-mediated siRNA Delivery and Gene Silencing", Molecular Pharmaceutics, Aug. 5, 2013, 10(8): 3262-3273.

Powe, et al., "Preeclampsia, a Disease of the Maternal Endothelium: the Role of Antiangiogenic Factors and Implications for Later Cardiovascular Disease", Circulation, vol. 123, No. 24, pp. 2856-2869, Jun. 11, 2011.

PubChem Database, Amino-Teg-Diol, National Institute or Biotechnology Information, PubChem Accession No. 22136768, 2003.

PubChem Database, SCHEMBL867745, National Institute for Biotechnology Information, PubChem Accession No. 12454428, 12 pages, 2005.

(56) References Cited

OTHER PUBLICATIONS

Putnam, David A., Antisense Strategies and Therapeutic Applications, American Journal of Health System Pharmacy, vol. 53, No. 2, pp. 151-160, Jan. 15, 1996.
Raouane et al., "Lipid Conjugated Oligonucleotides: A Useful Strategy for Delivery", Chem., 2012, 23: 1091-1104.
Reinhart, et al., Small RNAs Correspond to Centromere Heterochromatic Repeats, Science, vol. 297, No. 5588, 1 Page, Sep. 13, 2002.
Rigo, et al., Pharmacology of a Central Nervous System Delivered 2'-O-Methoxyethyl-Modified Survival of Motor Neuron Splicing Oligonucleotide in Mice and Nonhuman Primates, Journal of Pharmacology and Experimental Therapeutics, vol. 350, Issue 1, pp. 46-55, Jul. 1, 2014.
Rodriguez-Lebron, et al., Intrastriatal rAAV-Mediated Delivery of Anti-Huntingtin shRNAs Induces Partial Reversal of Disease Progression in R6/1 Huntington's Disease Transgenic Mice, Molecular Therapy, vol. 12, Issue 4, pp. 618-633, Oct. 2005.
Rupprecht, et al., Neuroactive Steroids: Mechanisms of Action and Neuropsychopharmacological Properties, Psychoneuroendocrinology, vol. 28, Issue 2, pp. 139-168, Feb. 2003.
Ruszkowski, et al., Biodistribution and Metabolism of a Mixed Backbone Oligonucleotide (GEM 231) Following Single and Multiple Dose Administration in Mice, Antisense and Nucleic Acid Drug Development, vol. 10, Issue 5, pp. 333-345, Jan. 30, 2009.
Sah, et al., Oligonucleotide Therapeutic Approaches for Huntington disease, The Journal of Clinical Investigation, vol. 121, No. 2, pp. 500-507, Feb. 1, 2011.
Samuelson, Kristin W., Post-Traumatic Stress Disorder and Declarative Memory Functioning: A Review, Dialogues in Clinical Neuroscience, vol. 13, No. 3, pp. 346-351, Sep. 2011.
Schirle, et al., Structural Basis for MicroRNA Targeting, Science, vol. 346, Issue 6209, pp. 608-613, Oct. 31, 2014.
Schwab, et al., An Approach for New Anticancer Drugs:Oncogene-Targeted Antisense DNA, Annals of Oncology, vol. 5, Issue 4, pp. 55-58, 1994.
Schwarz, et al., Asymmetry in the Assembly of the RNAi Enzyme Complex, Cell, vol. 115, Issue 2, pp. 199-208, Oct. 17, 2003.
Seq ID No. 1112 from U.S. Pat. No. 7,790,867. [Accessed Nov. 28, 2018, http://seqdata.uspto.gov/.psipsv?pageRequest=viewSequence&DocID=7790867&seq ID=1112.].
Song, et al., Sustained Small Interfering RNA-Mediated Human Immunodeficiency Virus Type 1 Inhibition in Primary Macrophages, Journal of Virology, vol. 77, No. 13, pp. 7174-7181, 2003.
Stalder, et al., The Rough Endoplasmatic Reticulum Is a Central Nucleation Site of siRNA-Mediated RNA Silencing, The EMBO Journal, vol. 32, Issue 8, pp. 1115-1127, Mar. 19, 2013.
Stein, et al., Inhibition of Vesivirus Infections in Mammalian Tissue Culture with Antisense Morpholino Oligomers, Antisense and Nucleic Acid Drug Development, vol. 11, Issue 5, pp. 317-325, Oct. 2001.
Stein, et al., Systemic and Central Nervous System Correction of Lysosomal Storage in Mucopolysaccharidosis Type VII Mice, Journal of Virology, vol. 73, No. 4, pp. 3424-3429, Apr. 1999.
Stokman, et al., Application of siRNA in Targeting Protein Expression in Kidney Disease, Advanced Drug Delivery Reviews, vol. 62, Issue 14, pp. 1378-1389, Nov. 30, 2010.
Sugo et al., "Development of antibody-siRNA conjugate targeted to cardiac and skeletal muscles", Journal of Controlled Release, Jun. 29, 2016, vol. 237, pp. 1-13.
Sui, et al., A DNA Vector-Based RNAi Technology to Suppress Gene Expression in Mammalian Cells, Proceedings of the National Academy of Sciences, vol. 99, No. 8, pp. 5515-5520, Apr. 16, 2002.
Tabernero, et al., First-in-Humans Trial of an RNA Interference Therapeutic Targeting VEGF and KSP in Cancer Patients with Liver Involvement, vol. 3, Issue 4, pp. 406-417, Apr. 2013.
Tang, et al., "Excess Soluble Vascular Endothelial Growth Factor Receptor-1 in Amniotic Fluid Impairs Lung Growth in Rats: Linking Preeclampsia With Bronchopulmonary Dysplasia", American Journal of Physiology-Lung Cellular and Molecular Physiology, vol. 302, No. 1, pp. L36-L46, Jan. 1, 2012.
Thadani, et al., "Pilot Study of Extracorporeal Removal of Soluble fms-like Tyrosine kinase 1 in Preeclampsia", Circulation, vol. 124, No. 8, pp. 940-950, Aug. 1, 2011.
Thomas et al. (2007) "Intronic polyadenylation signal sequences and alternate splicing generate human soluble Flt1 variants and regulate the abundance of soluble Flt1 in the placenta," The FASEB Journal, 21(14):3885-3895.
Thomas, et al., A Recently Evolved Novel Trophoblast-Enriched Secreted Form of fms-Like Tyrosine Kinase-1 Variant Is Up-Regulated in Hypoxia and Preeclampsia, The Journal of Clinical Endocrinology & Metabolism, vol. 94, Issue 7, pp. 2524-2530, Jul. 1, 2009.
Tischer, et al., "The Human Gene for Vascular Endothelial Growth Factor. Multiple Protein Forms are Encoded Through Alternative Exon Splicing", The Journal of Biological Chemistry, vol. 266, pp. 11947-11954, Jun. 25, 1991.
Turanov et al., "RNAi Modulation of Placental sFLT1 for the Treatment of Preeclampsia", Nature Biotechnology, Nov. 19, 2018, 36: 1164-1173.
Tuschl et al. (May 6, 2004) "The siRNA User Guide," Accessible on the Internet at URL: http://diyhpl.us/~bryan/irc/protocol-online/protocol-cache/sirna.html. [Last Accessed Aug. 11, 2016].
Tuschl, et al., Expanding small RNA interference, Nature Biotechnology, vol. 20, No. 5, pp. 446-448, 2002.
Uchida, et al., "An Integrated Approach for the Systematic Identification and Characterization of Heart-enriched Genes With Unknown Functions", BMC Genomics, vol. 10, No. 100, pp. 1-12, Mar. 2009.
Ueno et al., "Synthesis and silencing properties of siRNAs possessing lipophilic groups at their 3'-termini", Nucleic Acids Symposium Series, vol. 52, Issue 1, pp. 503-504, https://doi.org/10.1093/nass/nrn255. (Sep. 2008).
Vaught, et al., T7 Rna Polymerase Transcription with 5-Position Modified UTP Derivatives, Journal of the American Chemical Society, vol. 126, No. 36, pp. 11231-11237, Aug. 19, 2004.
Videira, et al., "Preclinical Development of siRNA Therapeutics: Towards the Match Between Fundamental Science and Engineered Systems", Nanomedicine: Nanotechnology, Biology and Medicine, vol. 10, No. 4, pp. 689-702, 2014.
Vorlová, et al., "Induction of Antagonistic Soluble Decoy Receptor Tyrosine Kinases by Intronic polyA Activation", Molecular Cell, vol. 43, Issue 6, pp. 927-939, Sep. 16, 2011.
Vorobjev, et al., Nuclease Resistance and RNase H Sensitivity of Oligonucleotides Bridged by Oligomethylenediol and Oligoethylene Glycol Linkers, Antisense and Nucleic Acid Drug Development, vol. 11, No. 2, pp. 77-85, Apr. 2011.
Wada et al., "Evaluation of the effects of chemically different linkers on hepatic accumulations, cell tropism and gene silencing ability of cholesterol-conjugated antisense oligonucleotides", Journal of Controlled Release, Elsevier, vol. 226, pp. 57-65, DOI: 10.1016/J.JCONREL.2016.02.007. (Feb. 5, 2016).
Watanabe, et al., Endogenous siRNAs From Naturally Formed dsRNAs Regulate Transcripts in Mouse Oocytes, Nature, vol. 453, No. 7194, pp. 539-543, Apr. 10, 2008.
Weyer, et al., Developmental and Cell Type-Specific Expression of the Neuronal Marker NeuN in the Murine Cerebellum, Journal of Neuroscience Research, vol. 73, Issue 3, pp. 400-409, May 23, 2003.
Whitehead, et al., "Knocking Down Barriers: Advances in siRNA Delivery", Nature Reviews Drug Discovery, vol. 8, No. 2, pp. 129-138, Feb. 2009.
Wong, et al., Co-Injection of a Targeted, Reversibly Masked Endosomolytic Polymer Dramatically Improves the Efficacy of Cholesterol-Conjugated Small Interfering RNAs In Vivo, Nucleic Acid Therapeutics, vol. 22, No. 6, pp. 380-390, Nov. 26, 2012.
Wooddell, et al., Hepatocyte-targeted RNAi Therapeutics for the Treatment of Chronic Hepatitis B Virus Infection, Molecular Therapy, vol. 21, Issue 5, pp. 973-985, May 2013.
Wright, et al., Identification of Factors That Contribute to Recombinant AAV2 Particle Aggregation and Methods to Prevent Its Occurrence During Vector Purification and Formulation, Molecular Therapy, vol. 12, Issue 1,, pp. 171-178, Jul. 2005.

(56) References Cited

OTHER PUBLICATIONS

Xia, et al., siRNA-Mediated Gene Silencing in Vitro and In Vivo, Nature Biotechnology, vol. 20, No. 10, pp. 1006-1010, Sep. 16, 2002.
Young, et al., Pathogenesis of Preeclampsia, Annual Review of Pathology: Mechanisms of Disease, vol. 5, pp. 173-192, Feb. 2, 2010.
Younis, et al., Overview of the Nonclinical Development Strategies and Class-Effects of Oligonucleotide-Based Therapeutics, A Comprehensive Guide to Toxicology in Preclinical Drug Development, Chapter 26, pp. 647-664, 2013.
Yu, et al., RNA Interference by Expression of Short-Interfering RNAs and Hairpin RNAs in Mammalian Cells, Proceedings of the National Academy of Sciences, vol. 99, No. 9, pp. 6047-6052., Apr. 30, 2002.
Yu, et al., Single-Stranded RNAs Use RNAi to Potently and Allele-Selectively Inhibit Mutant Huntingtin Expression, Cell, vol. 150, Issue 5, pp. 895-908, Aug. 31, 2012.
Zeng, et al., Both Natural and Designed Micro RNAs Can Inhibit the Expression of Cognate mRNAs When Expressed in Human Cells, Molecular Cell, vol. 9, pp. 1327-1333, Jun. 2002.
Zeng, et al., Sequence Requirements for Micro RNA Processing and Function in Human Cells, RNA, vol. 9, pp. 112-123, 2003.
Zhang, et al., "Birth-weight-for-gestational-age Patterns by Race, Sex, and Parity in the United States Population", Obstetrics & Gynecology, vol. 86, No. 2, pp. 200-208, 1995.
Zhang, et al., "Several rAAV Vectors Efficiently Cross the Blood-brain Barrier and Transduce Neurons and Astrocytes in the Neonatal Mouse Central Nervous System", Molecular Therapy, vol. 19, Issue 8, pp. 1440-1448, Aug. 1, 2011.
Zhang, et al., Cyclohexane 1,3-Diones and Their Inhibition of Mutant SOD1-Dependent Protein Aggregation and Toxicity in PC12 Cells, Bioorganic & Medicinal Chemistry, vol. 20, Issue 2, pp. 1029-1045, Jan. 15, 2012.
Zou, et al., Liposome-Mediated NGF Gene Transfection Following Neuronal Injury: Potential Therapeutic Applications, Gene Therapy, vol. 6, No. 6, pp. 994-1005, Jun. 25, 1999.
Zuccato, et al., Molecular Mechanisms and Potential Therapeutical Targets in Huntington's Disease, Physiological Reviews, vol. 90, No. 3, pp. 905-981, Jul. 1, 2010.
U.S. Appl. No. 15/089,319 2016/0355808 U.S. Pat. No. 9,809,817, filed Apr. 1, 2016 Dec. 8, 2016 Nov. 7, 2017, Anastasia Khvorova, Oligonucleotide Compounds for Targeting Huntingtin mRNA.
U.S. Appl. No. 15/697,120 2018/0094263 U.S. Pat. No. 10,435,688, filed Sep. 6, 2017 Apr. 5, 2018 Oct. 8, 2019, Anastasia Khvorova, Oligonucleotide Compounds for Targeting Huntingtin mRNA.
U.S. Appl. No. 16/263,200 2019/0225965 U.S. Pat. No. 10,744,327, filed Jan. 31, 2019 Jul. 25, 2019 Sep. 15, 2020, Anastasia Khvorova, Oligonucleotide Compounds for Targeting Huntingtin mRNA.
U.S. Appl. No. 16/811,580 2020/0308584 U.S. Pat. No. 11,230,713, filed Mar. 6, 2020 Oct. 1, 2020 Jan. 5, 2022, Anastasia Khvorova, Oligonucleotide Compounds for Targeting Huntingtin mRNA.
U.S. Appl. No. 17/536,647 2022/0251554, filed Nov. 29, 2021 Aug. 11, 2022, Anastasia Khvorova, Oligonucleotide Compounds for Targeting Huntingtin mRNA.
U.S. Appl. No. 15/089,437 2016/0355826 U.S. Pat. No. 9,862,952, filed Apr. 1, 2016 Dec. 8, 2016 Jan. 9, 2018, Anastasia Khvorova, Oligonucleotide Compounds for Treatment of Preeclampsia and Other Angiogenic Disorders.
U.S. Appl. No. 15/814,350 2018/0179546 U.S. Pat. No. 10,519,451, filed Nov. 15, 2017 2018 Dec. 31, 2019, Anastasia Khvorova, Oligonucleotide Compounds for Treatment of Preeclampsia and Other Angiogenic Disorders.
U.S. Appl. No. 16/675,369 2020/0165618 U.S. Pat. No. 11,345,917, filed Nov. 6, 2019 May 28, 2020 May 11, 2022, Anastasia Khvorova, Oligonucleotide Compounds for Treatment of Preeclampsia and Other Angiogenic Disorders.
U.S. Appl. No. 17/718,918 2022/0364100, filed Apr. 12, 2022 Nov. 17, 2022, Anastasia Khvorova, Oligonucleotide Compounds for Treatment of Preeclampsia and Other Angiogenic Disorders.
U.S. Appl. No. 15/089,423 2016/0319278, filed Apr. 1, 2016 Nov. 3, 2016, Anastasia Khvorova, Fully Stabilized Asymmetric Sirna.
U.S. Appl. No. 15/691,120 2017/0369882, filed Aug. 30, 2017 Dec. 28, 2017, Anastasia Khvorova, Fully Stabilized Asymmetric Sirna.
U.S. Appl. No. 16/927,543 2021/0024926, filed Jul. 13, 2020 Jan. 28, 2021, Anastasia Khvorova, Fully Stabilized Asymmetric Sirna.
U.S. Appl. No. 15/236,051 2017/0043024 U.S. Pat. No. 10,633,653, filed Aug. 12, 2016 Feb. 16, 2017 Apr. 28, 2020, Anastasia Khvorova, Bioactive Conjugates for Oligonucleotide Delivery.
U.S. Appl. No. 16/812,714 2020/0339983, filed Mar. 9, 2020 Oct. 29, 2020, Anastasia Khvorova, Bioactive Conjugates for Oligonucleotiae Delivery.
U.S. Appl. No. 15/419,593 2017/0312367 U.S. Pat. No. 10,478,503, filed Jan. 30, 2017 Nov. 2, 2017 Nov. 19, 2019, Anastasia Khvorova, Branched Oligonucleotides.
U.S. Appl. No. 16/390,712 2019/0247507 U.S. Pat. No. 10,799,591, filed Apr. 22, 2019 Aug. 15, 2019 Oct. 13, 2020, Anastasia Khvorova, Branched Oligonucleotides.
U.S. Appl. No. 17/012,787 2021/0085793, filed Sep. 4, 2020 Mar. 25, 2021, , Anastasia Khvorova, Branched Oligonucleotides.
U.S. Appl. No. 16/322,212 2019/0185855, filed Jan. 31, 2019 Jun. 20, 2019, Anastasia Khvorova, Conjugated Oligonucleotides.
U.S. Appl. No. 16/015,440 2019/0024082 U.S. Pat. No. 10,844,377, filed Jun. 22, 2018 Jan. 24, 2019 Nov. 24, 2020, Anastasia Khvorova, Two-Tailed Self-Delivering Sirna.
U.S. Appl. No. 17/071,473 2021/0139901, filed Oct. 15, 2020 May 13, 2021, Anastasia Khvorova, Two-Tailed Self-Delivering.
U.S. Appl. No. 16/537,374 2020/0123543, filed Aug. 9, 2019 Apr. 23, 2020, Anastasia Khvorova, Modified Oligonucleotides Targeting SNPs.
U.S. Appl. No. 16/988,391 2021/0071177, filed Aug. 7, 2020 Mar. 11, 2021, Anastasia Khvorova, Modified Oligonucleotides Targeting SNPs.
U.S. Appl. No. 16/831,470 2020/0385740, filed Mar. 26, 2020 Dec. 10, 2020, Anastasia Khvorova, Modified Oligonucleotides with Increased Stability.
U.S. Appl. No. 17/213,852 2022/0010309, filed Mar. 26, 2021 Jan. 13, 2022, Anastasia Khvorova, Synthesis of Modified Oligonucleotides with Increased Stability.
U.S. Appl. No. 16/746,555 2020/0270605, filed Jan. 17, 2020 Aug. 27, 2020 Nov. 8, 2022, Anastasia Khvorova, Dynamic Pharmacokinetic-Modifying Anchors.
U.S. Appl. No. 17/725,102 2022/0372476, filed Apr. 20, 2022 Nov. 24, 2022, , Anastasia Khvorova, Dynamic Pharmacokinetic-Modifying Anchors.
U.S. Appl. No. 17/792,705 2023/0061751, filed Jul. 13, 2022 Mar. 2, 2023, Anastasia Khvorova, Universal Dynamic Pharmacokinetic-Modifying Anchors.
U.S. Appl. No. 16/550,076 2020/0087663 U.S. Pat, No, 11,279,930, filed Aug. 23, 2019 / Mar. 19, 2020 / Mar. 22, 2022, Anastasia Khvorova, O-Methyl Rich Fully Stabilized Oligonucleotides.
U.S. Appl. No. 16/999,759 2021/0115442, filed Aug. 21, 2020 / Apr. 22, 2021, Anastasia Khvorova, O-Methyl Rich Fully Stabilized Oligonucleotides.
U.S. Appl. No. 17/580,269 2022/0251555, filed Jan. 20, 2022 / Aug. 11, 2022, Anastasia Khvorova, O-Methyl Rich Fully Stabilized Oligonucleotides.
U.S. Appl. No. 17/022,678 2021/0108200, filed Sep. 16, 2020 Apr. 15, 2021, Anastasia Khvorova, Branched Lipid Conjugates of siRNA for Specific Tissue Delivery.
U.S. Appl. No. 17/331,146 2021/0395739, filed May 26, 2021 Dec. 23, 2021, Anastasia Khvorova, Synthetic Oligonucleotides Having Regions of Block and Cluster Modifications.
U.S. Appl. No. 17/377,632 2022/0042015, filed Jul. 16, 2021 Feb. 10, 2022, Anastasia Khvorova, Conjugated Oligonucleotides for Tissue Specific Delivery.
U.S. Appl. No. 17/532,636 2022/0228141, filed Nov. 22, 2021 Jul. 21, 2022, Anastasia Khvorova, Oligonucleotides for DGAT2 Modulation.
U.S. Appl. No. 17/846,526 2023/0078622, filed Jun. 22, 2022 Mar. 16, 2023, Anastasia Khvorova, Optimized ANTI-FLT1 Oligonucleotide Compounds for Treatment of Preeclampsia and Other Angiogenic Disorders.

(56) References Cited

OTHER PUBLICATIONS

Alagia, et al., Exploring PAZ/3'-overhang Interaction to Improve siRNA Specificity. A Combined Experimental and Modeling Study, Chemical Science, vol. 9, No. 8, pp. 2074-2086, 2018.
Ämmälä, et al., Targeted Delivery of Antisense Oligonucleotides to Pancreatic β-cells, Science Advances, vol. 4, No. 10, eaat3386, pp. 1-11, Oct. 17, 2018.
Betkekar, et al., A Tandem Enyne/Ring Closing Metathesis Approach to 4-Methylene-2-cyclohexenols: An Efficient Entry to Otteliones and Loloanolides, Organic Letters, Dec. 6, 2011, vol. 14, No. 1, pp. 198-201.
Biscans et al., "Docosanoic acid conjugation to siRNA enables functional and safe delivery to skeletal and cardiac muscles", Molecular Therapy, Apr. 2021, vol. 29, No. 4, pp. 1382-1394.
Biscans et al., "Hydrophobicity of Lipid-Conjugated siRNAs Predicts Productive Loading to Small Extracellular Vesicles", Molecular Therapy, Jun. 2018, vol. 26, No. 6, pp. 1520-1528.
Biscans et al., "The Chemical Structure and Phosphorothioate content of hydrophobically modified siRNAs impact extrahepatic distribution and efficacy", Nucleic Acids Research, 2020, vol. 48, No. 14, pp. 7665-7680.
Biscans, et al., The Valency of Fatty Acid Conjugates Impacts siRNA Pharmacokinetics, Distribution, and Efficacy in Vivo, Journal of Controlled Release, vol. 302, pp. 116-125, Mar. 2019.
Brown, et al., Effect of Phosphorothioate Modification of Oligodeoxynucleotides on Specific Protein Binding, Journal of Biological Chemistry, vol. 269, No. 43, pp. 26801-26805, 1994.
Chang, et al., Asymmetric Shorter-duplex siRNA Structures Trigger Efficient Gene Silencing With Reduced Nonspecific Effects, Molecular Therapy, vol. 17, Issue 4, pp. 725-732, Apr. 2009.
Chappell, et al., Mechanisms of Palmitic Acid-conjugated Antisense Oligonucleotide Distribution in Mice, Nucleic Acids Research, vol. 48, Issue 8, ,, pp. 4382-4395, May 7, 2020.
Choi et al., Suppression of diacylglycerol acyltransferase-2 (DGAT2), but not DGAT1, with antisense oligonucleotides reverses diet-induced hepatic steatosis and insulin resistance, J Biol Chem., Aug. 3, 2007, 282(31): 22678-22688.
Chu, et al., Potent RNAi by Short RNA Triggers, RNA, vol. 14, pp. 1714-1719, 2008.
Collis, "The synthesis of vinylphosphonate-linked RNA", Ph.D. Thesis, University of Nottingham, Feb. 2008.
Crooke, et al., Cellular Uptake and Trafficking of Antisense Oligonucleotides, Nature Biotechnology, vol. 35, No. 3, pp. 230-237, Mar. 2017.
Crooke, et al., Phosphorothioate Modified Oligonucleotide—Protein Interactions, Nucleic Acids Research, May 1, 2020, 48(10): 5235-5253.
Czauderna, et al., Structural Variations and Stabilising Modifications of Synthetic siRNAs in Mammalian Cells, Nucleic Acids Research, vol. 31, Issue 11, pp. 2705-2716, Jun. 2003.
Dowdy, Overcoming Cellular Barriers for RNA Therapeutics, Nature Biotechnology, vol. 35, pp. 222-229, Feb. 27, 2017.
Ducruix, et al., Crystallization of Nucleic Acids and Proteins: A Practical Approach, Second Edition, 1999, pp. 201-216.
Echevarría et al., Evaluating the Impact of Variable Phosphorothioate Content in Tricyclo-DNA Antisense Oligonucleotides in a Duchenne Muscular Dystrophy Mouse Model, Nucleic Acid Therapeutics, vol. 29, No. 3, pp. 148-160, May 30, 2019.
Eckstein, Developments in RNA Chemistry, A Personal View, Biochimie, vol. 84, No. 9, pp. 841-848, Sep. 2002.
Egli, et al., Re-engineering RNA Molecules Into Therapeutic Agents, Accounts of Chemical Research, vol. 52, pp. 1036-1047, 2019.
Elbashir, et al., RNA Interference Is Mediated by 21- and 22-Nucleotide RNAs, Genes & Development, vol. 15, No. 2, pp. 188-200, 2001.
Extended European Search Report for European Patent Application No. 19852320.1, dated May 2, 2022.
Extended European Search Report for European Patent Application No. 20741865.8, dated Apr. 26, 2023.
Extended European Search Report for European Patent Application No. 19847586.5, dated Jun. 21, 2023.
Fitzgerald, et al., A Highly Durable RNAi Therapeutic Inhibitor of PCSK9, New England Journal of Medicine, vol. 376, No. 1, pp. 41-51, Jan. 5, 2017.
Foster et al., "Advanced siRNA Designs Further Improve In Vivo Performance of GalNAc—siRNA Conjugates", Molecular Therapy, vol. 26, No. 3, pp. 709-717, Mar. 2018.
Gaus, et al., Characterization of the Interactions of Chemically-modified Therapeutic Nucleic Acids With Plasma Proteins Using a Fluorescence Polarization Assay, Nucleic Acids Research, vol. 47, No. 3, pp. 1110-1122, 2019.
Ghidini et al., "An RNA modification with remarkable resistance to RNase A", Chemical Communicaitons, Aug. 8, 2013, 49(79): 9036-9038.
Gvozdeva et al., "Noncanonical Synthetic RNAi Inducers InL RNA Interference", InTech, Apr. 6, 2016.
Haly et al., "An extended phosphate linkage: Synthesis, hybridization and modeling studies of modified oligonucleotides", Nucleosides and Nucleotides, 1996, 15(7-8): 1383-1395.
Hanuš et al., "-CH2-lengthening of the internucleotide linkage in the ApA dimer can improve its conformational compatibility with its natural polynucleotide counterpart", Nucleic Acids Research, Dec. 15, 2001, 29(24): 5182-5194.
Hillier et al., yw97a12.r1 Soares_placenta_8to9weeks_2NbHP8to9W Homo sapiens cDNA clone Image:260158 5' similar to GB:X51602_cds1 Vascular Endothelial Growth Factor Receptor 1 (Human); contains element OFR repetitive element, mRNA sequence, NIH, Genbank Accession No. N47911.1, Feb. 14, 1996.
International Search Report and Written Opinion for PCT International Patent Application No. PCT/US2019/048027 mailed Nov. 15, 2019.
International Search Report and Written Opinion for PCT International Patent Application No. PCT/US2020/047492, mailed Feb. 17, 2022.
International Search Report and Written Opinion received for PCT Patent Application No. PCT/US2021/034290, mailed on Nov. 4, 2021.
International Search Report and Written Opinion received for PCT Patent Application No. PCT/US2021/041946, mailed on Oct. 29, 2021.
International Search Report and Written Opinion received for PCT Patent Application No. PCT/US2021/060356, mailed on Apr. 13, 2022.
Kaura, et al., Synthesis, Hybridization Characteristics, and Fluorescence Properties of Oligonucleotides Modified with Nucleobase-Functionalized Locked Nucleic Acid Adenosine and Cytidine Monomers, The Journal of Organic Chemistry, Jun. 16, 2014, 79: 6256-6268.
Kofoed et al., "Oligodeoxynucleotides with Extended 3'- and 5'-Homologous Internucleotide Linkages", Acta Chemica Scandanavia, 1997, 51: 318-324.
Kubo, et al., Modified 27-nt dsRNAs With Dramatically Enhanced Stability in Serum and Long-term RNAi Activity, Oligonucleotides, vol. 17, No. 4, pp. 445-464, 2007.
Lebedeva et al., "Phosphorothioate oligodeoxynucleotides as inhibitors of gene expression: antisense and non-antisense effects", Applications of Antisense therapies to restenosis, 1999, p. 101.
Liang, et al., Identification and Characterization of Intracellular Proteins That Bind Oligonucleotides With Phosphorothioate Linkages, Nucleic Acids Research, vol. 43, Issue 5, pp. 2927-2945, Mar. 11, 2015.
Loy et al., "Allele-Specific Gene Silencing in Two Mouse Models of Autosomal Dominant Skeletal Myopathy", PLoS One, Nov. 2012, 7(11): e49757, 11 pages.
Ma, et al., Structural Basis for Overhang-Specific Small Interfering RNA Recognition by the PAZ Domain, Nature, vol. 429, No. 6989, pp. 318-322, May 20, 2004.
Magner et al., "Influence of mismatched and bulged nucleotides on SNP-preferential RNase H cleavage of RNA-antisense gapmer heteroduplexes", Scientific Reports, Oct. 2017, 7(12532), 16 pages.

(56) References Cited

OTHER PUBLICATIONS

Mazur et al., "Isosteres of natural phosphates. 11. Synthesis of a phosphonic acid analogue of an oligonucleotide", Tetrahedron, 1984, 40(20): 3949-3956.

Monteys et al., "Artificial miRNAs Targeting Mutant Huntingtin Show Preferential Silencing In Vitro and In Vivo", Molecular Therapy, Nucleic Acids, 2015, 4: E234, 11 pages.

Nair, et al., Impact of Enhanced Metabolic Stability on Pharmacokinetics and Pharmacodynamics of GalNAc—siRNA Conjugates, Nucleic Acids Research, vol. 45, Issue 19, pp. 10969-10977, Nov. 2, 2017.

Parmar, et al., 5'-(E)-Vinylphosphonate: A Stable Phosphate Mimic can Improve the RNAi Activity of siRNA-GalNAc Conjugates, ChemBioChem, vol. 17, pp. 985-989, Jun. 2, 2016.

Partial Supplementary European Search Report for European Patent Application No. 20777915.8, mailed Apr. 5, 2023.

Prakash, et al., Identification of Metabolically Stable 5'-Phosphate Analogs That Support Single-Stranded siRNA Activity, Nucleic Acids Research, Mar. 9, 2015, 43(6): 2993-3011.

PubChem Database, CID-16131506, Compund Summary: dGTGGGTGGGT, Jul. 3, 2007, Retrieved from url: https://pubchem.ncbi.nlm.nih.gov/compound/16131506.

Raal, et al., Inclisiran for the Treatment of Heterozygous Familial Hypercholesterolemia, New England Journal of Medicine, vol. 382, No. 16, pp. 1520-1530, Apr. 16, 2020.

Reynolds, A, et al., Rational siRNA Design for RNA Interference, Nature Biotechnology, vol. 22, No. 3, pp. 326-330, Apr. 2004.

Schoch, et al., Antisense Oligonucleotides: Translation From Mouse Models to Human Neurodegenerative Diseases, Neuron, vol. 94, Issue 6, pp. 1056-1070, Jun. 21, 2017.

Setten, et al., The Current State and Future Directions of RNAi-based Therapeutics, Nature Reviews Drug Discovery, vol. 18, pp. 421-446, Mar. 7, 2019.

Shen, et al., 2'-fluoro-modified Phosphorothioate Oligonucleotide Can Cause Rapid Degradation of P54nrb and PSF, Nucleic Acids Research, vol. 43, Issue 9, pp. 4569-4578, May 19, 2015.

Shen, et al., Acute Hepatotoxicity of 2' Fluoro-modified 5-10-5 Gapmer Phosphorothioate Oligonucleotides in Mice Correlates With Intracellular Protein Binding and the Loss of DBHS Proteins, Nucleic Acids Research, vol. 46, Issue 5, pp. 2204-2217, Mar. 16, 2018.

Shen, et al., Chemical Modification of PS-ASO Therapeutics Reduces Cellular Protein-binding and Improves the Therapeutic Index, Nature Biotechnology, vol. 37, pp. 640-650, Apr. 29, 2019.

Stein, et al., Physicochemical Properties of Phosphorothioate Oligodeoxynucleotides, Nucleic Acids Research, vol. 16, No. 8, pp. 3209-3221, Apr. 25, 1988.

Sun, et al., Asymmetric RNA Duplexes Mediate RNA Interference in Mammalian Cells, Nature Biotechnology, vol. 26, pp. 1379-1382, Dec. 2008.

Tan et al., "Allele-Specific Targeting of microRNAs to HLA-G and Risk of Asthma", American Journal of Human Genetics, Oct. 2007, 81(4): 829-834.

Teng et al., "A GDF15 3' UTR variant, rs1054564, results in allele-specific translational repression of GDF15 by hsa-miR-1233-3p", PLoS One, Aug. 2017, 12(8): e0183187, 15 pages.

Vickers, et al., Development of a Quantitative BRET Affinity Assay for Nucleic Acid-protein Interactions, PloS One, vol. 11, No. 8, p. e0161930, pp. 1-17, Aug. 29, 2016.

Wickstrom, Oligodeoxynucleotide Stability in Subcellular Extracts and Culture Media, Journal of Biochemical and Biophysical Methods, vol. 13, Issue 2, pp. 97-102, Sep. 1986.

Yamana, et al., 2'-Pyrene Modified Oligonucleotide Provides a Highly Sensitive Fluorescent Probe of RNA, Nucleic Acids Research, 1999, 27(11): 2387-2392.

Yekta, et al., MicroRNA-Directed Cleavage of HOXB8 mRNA, Science, Apr. 23, 2004, 304(5670): 594-596.

Zamore, et al., Ancient Pathways Programmed by Small RNAs, Science, May 17, 2002, 296(5571): 1265-1269.

Zlatev, et al., Reversal of siRNA-mediated Gene Silencing in Vivo, Nature Biotechnology, vol. 36, No. 6, pp. 509-511, 2018.

Alterman et al., "A divalent siRNA chemical scaffold for potent and sustained modulation of gene expression throughout the central nervous system", Nat Biotechnol., Aug. 2019, 37(8): 884-894.

Bertram et al., "Vinylphosphonate Internucleotide Linkages Inhibit the Activity of PcrA DNA Helicase", Biochemistry, Jun. 18, 2002, 41(24): 7725-7731.

Chatterjee et al., "Mechanisms of DNA damage, repair, and mutagenesis", DNA Repair, Apr. 16, 2016, 42: 26-32.

Doddridge et al., Effects of Vinylphosphonate Internucleotide Linkages on the Cleavage Specificity of Exonuclease III and on the Activity of DNA Polymerase I, Biochemistry, Mar. 25, 2003, 42(11): 3239-3246.

Dua et al., "Modified siRNA Structure With a Single Nucleotide Bulge Overcomes Conventional siRNA-mediated Off-target Silencing", Molecular Therapy, Jun. 2011, 16(9): 1676-1687.

Etzold et al., "The extension of the sugar chain of thymidine: a new route to 5'-deoxyhexose nucleosides", Chemical Communications (London), 1968, Issue 7.

Extended European Search Report for European Patent Application No. 20856904.6, mailed Jan. 2, 2024.

Extended European Search Report for European Patent Application No. 21741867.2, mailed Mar. 12, 2024.

Extended Supplementary European Search Report for European Patent Application No. 20777915.8, mailed Sep. 15, 2023.

Flower et al., MSH3 Modifies Somatic instability and Disease Severity in Huntington's and Myotonic Dystrophy Type 1, Brain, A Journal of Neurology, Jul. 2019, 142(7): 1876-1886.

Ghosh et al., "Comparing 2-nt 3' overhangs against blunt-ended siRNAs: a systems biology based study", BMC Genomics, 2009, 10(Suppl. 1):S17.

Godinho et al., "PK-modifying anchors significantly alter clearance kinetics, tissue distribution, and efficacy of therapeutics siRNAs", Mol Ther Nucleic Acids, Jun. 13, 2022,29: 116-132, ePublished Sep. 13, 2022.

Harlow et al., "Antibodies: A Laboratory Manual", Cold Spring Harbor Laboratory Chapter 14, Second Edition, 2013.

International Search Report & Written Opinion Received for PCT Application No. PCT/US2021/028166, mailed on Nov. 26, 2021.

International Search Report & Written Opinion Received for PCT Application No. PCT/US2021/044158, dated Jan. 31, 2022.

International Search Report & Written Opinion Received for PCT Application No. PCT/US2022/039047, dated Mar. 3, 2023.

International Search Report and Written Opinion for PCT International Patent Application No. PCT/US2020/025017, mailed Sep. 18, 2020.

International Search Report and Written Opinion in related PCT Application No. PCT/US2021/024425, mailed Oct. 15, 2021.

Jo et al., "Small Interfering RNA Nunchucks with a Hydrophobic Linker for Efficient Intracellular Delivery", Macromol Biosci., 2014, 14: 195-201.

Kachare et al., "Phospho-carboxylic anhydride of a homologated nucleoside leads to primer degradation in the presence of a polymerase", Bioorg Med Chem Letters, Jun. 15, 2014, 24(12): 2720-2723.

Lee et al., A Novel Approach to Investigate Tissue-specific Trinucleotide Repeat Instability, BMC Systems Biology, Mar. 19, 2010, 4(29): 1-16.

Lee et al., Adeno-associated virus (AAV) vectors: Rational design strategies for capsid engineering, Current Opinion in Biomed. Eng., 2018, 58-63.

Mikhailov et al., "Use of 5-deoxy-ribo-hexofuranose derivatives for the preparation of 5'-nucleotide phosphonates and homoribonucleosides", Collect Czech Chem Commun., 1989, 54(4): 1055-1066.

Miller, et al., Receptor-mediated Uptake of Phosphorothioate Antisense Oligonucleotides in Different Cell Types of the Liver, Nucleic Acid Therapeutics, vol. 28, No. 3, pp. 119-127, 2018.

Moss et al., Identification of Genetic Variants Associated with Huntington's Disease Progression: A Genome-wide Association Study, The Lancet, Neurology, Sep. 2017, 16(9): 701-711.

Namjou et al., "GWAS and enrichment analyses of non-alcoholic fatty liver disease identify new trait-associated genes and pathways across eMERGE Network", BMC Medicine, Jul. 2019, 17: 135, 19 pages.

(56) References Cited

OTHER PUBLICATIONS

Noguchi et al., "Allele-specific Gene Silencing of Mutant mRNA Restores Cellular Function in Ullrich Congenital Muscular Dystrophy Fibroblasts", Molecular Therapy-Nucleic Acids, Jun. 2014, 3: e171.

Ohtsuka et al., "Joining of synthetic ribotrinucleotides with defined catalyzed by T4 RNA ligase", European Journal of Biochemistry, 1977, 81(2): 285-291.

Oishi et al., "Lactosylated Poly(ethylene glycol)-siRNA Conjugate through Acid-Labile B-Thiopropionate Linkage to Construct pH-Sensitive Polyion Complex Micelles Achieving Enhanced Gene Silencing in Hepatoma Cells", J. Am. Chem. Soc., 2005, 127: 1624-1625.

Old et al., "Cloning in Yeast and Microbial Eukaryotes", Principles of Gene Manipulation: An Introduction to Genetic Engineering, Studies in Microbiology, 1989, 2(11): 199-221.

Østergaard et al., "Conjugation of hydrophobic moieties enhances potency of antisense oligonucleotides in the muscle of rodents and non-human primates", Nucleic Acids Research, 2019, 47(12): 6045-6058.

Padiukova et al., "Synthesis of 5'-derivatives of thymidine", Bioorg Khim., 1990, 16(5): 668-673 [Article in Russian—no abstract available].

Partial European Search Report for European Patent Application No. 21792058.6, dated Apr. 17, 2024.

Partial Supplementary European Search Report for European Patent Application No. 20852443.9, mailed Aug. 25, 2023.

Partial Supplementary European Search Report for European Patent Application No. 20856904.6, mailed Sep. 13, 2023.

Roy et al., "Synthesis of DNA/RNA and Their Analogs via Phosphoramidite and H-Phosphonate Chemistries", Molecules, 2013, 18(11): 14268-14284.

Rozners et al., "Synthesis and Properties of RNA Analogues Having Amides as Interuridine Linkages at Selected Positions", JACS Articles, Sep. 6, 2003, 125: 12125-12136.

Schlegal et al., "Chirality Dependent Potency Enhancement and Structural Impact of Glycol Nucleic Acid Modification on siRNA", JACS, Jun. 1, 2017, pp. 1-28.

Schwarz et al., "Designing siRNA that distinguish between genes that differ by a single nucleotide", PLOS Genetics, Sep. 2006, 2(9): e140.

Shukla et al., "Exploring Chemical Modifications for siRNA Therapeutics: A Structural and Functional Outlook", ChemMedChem, Feb. 19, 2010, 5(3): 328-349.

Sibley et al., "Identification of Allele-Specific RNAi Effectors Targeting Genetic Forms of Parkinson's Disease", PLOS One, Oct. 2011, 6(10): e26194.

Sipova et al., "5'-O-Methylphosphonate nucleic acids—new modified DNAs that increase the *Escherichia coli* RNase H cleavage rate of hybrid duplexes", Nucleic Acids Research, 2014, 42(8): 5378-5389.

Smith et al., "RNA Nanotherapeutics for the Amelioration of Astroglial Reactivity", Mol Ther Nucleic Acids, Mar. 2, 2018, 10: 103-121, ePublished Nov. 24, 2017.

Tai et al., "Current Aspects of siRNA Bioconjugate for In Vitro and In Vivo Delivery", Molecules, Jun. 2019, 24(12): 2211, ePublished Jun. 13, 2019.

Tome et al., MSH3 Polymorphisms and Protein Levels Affect CAG Repeat Instability in Huntington's Disease Mice, PLOS Genetics, Feb. 28, 2013, 9(2): el003280, 1-16.

You et al., "Design of LNA probes that improve mismatch discrimination", Nucleic Acids Research, May 2006, 34(8): e60, 11 pages.

Zeng et al., "RNA Interference in human cells is restricted to the cytoplasm", RNA, Jul. 1, 2002, 8(7): 855-860.

Zhou et al., "Functional In Vivo Delivery of Multiplexed Anti-HIV-1 siRNAs via a Chemically Synthesized Aptamer With a Sticky Bridge", Mol Ther., Jan. 2013, 21(1): 192-200.

* cited by examiner

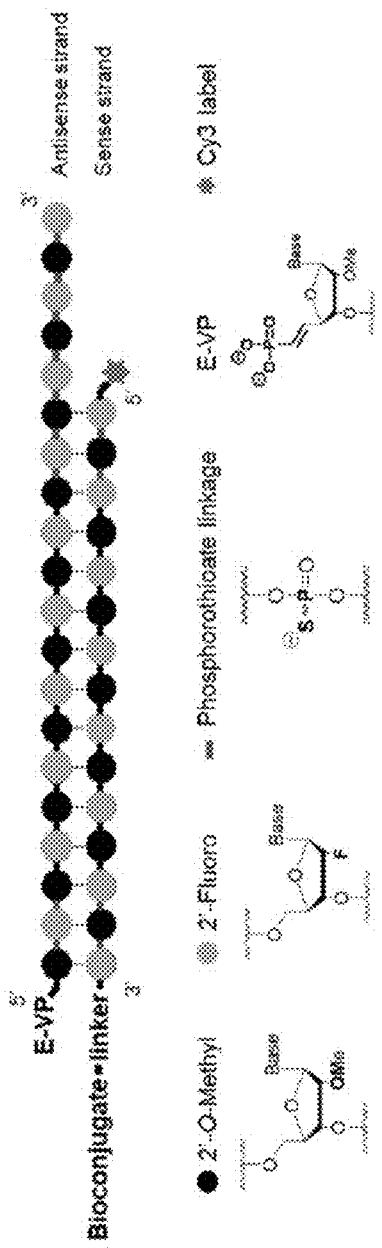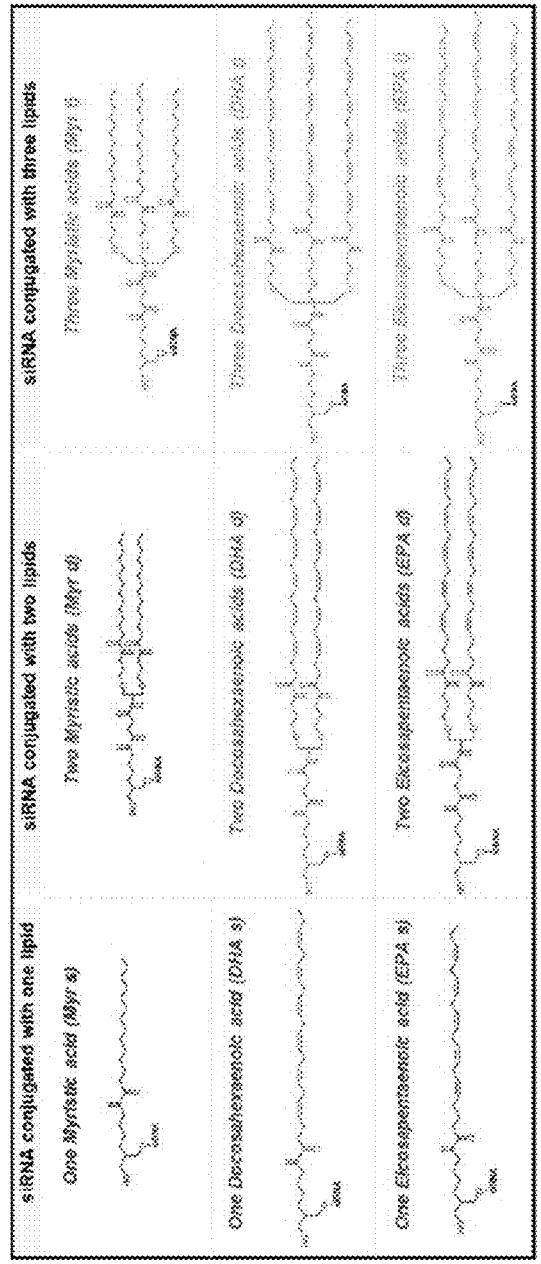
FIG. 1A
FIG. 1B

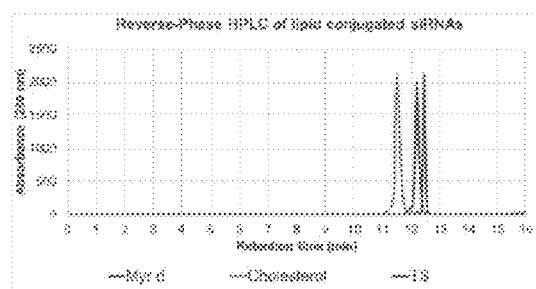
FIG. 7A
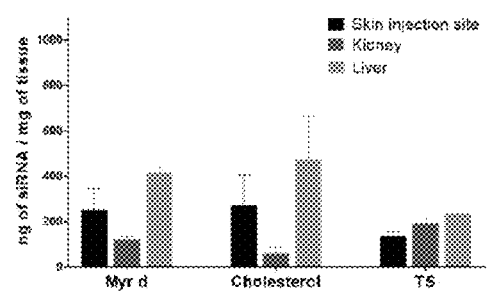
FIG. 7B
FIG. 7C
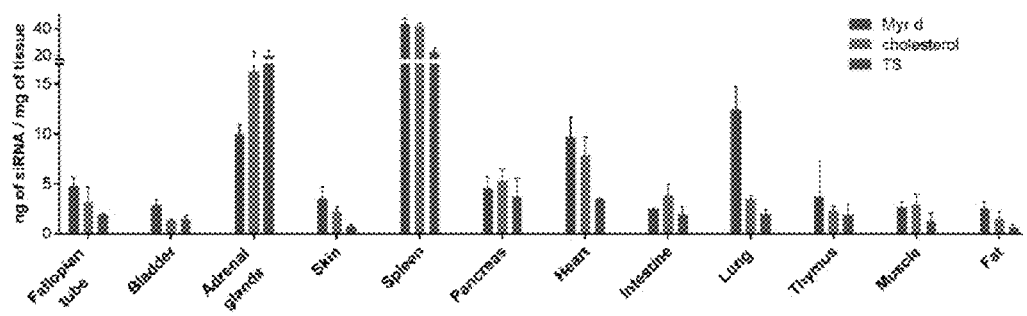
FIG. 7D
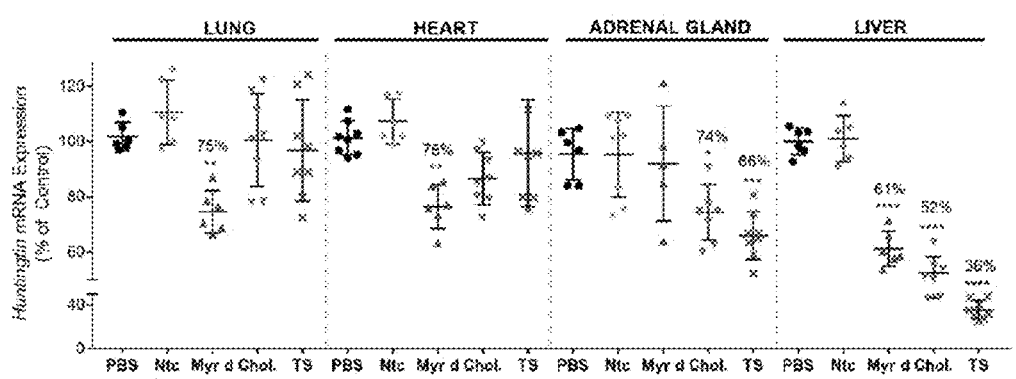

BRANCHED LIPID CONJUGATES OF siRNA FOR SPECIFIC TISSUE DELIVERY

CROSS-REFERENCE TO RELATED APPLICATIONS

This application claims priority to U.S. Provisional Patent Application Ser. No. 62/900,971, filed Sep. 16, 2019, the entire disclosures of which is hereby incorporated herein by reference.

STATEMENT REGARDING FEDERALLY SPONSORED RESEARCH OR DEVELOPMENT

This invention was made with government support under Grant No. HD086111 awarded by the National Institutes of Health. The Federal Government has certain rights in the invention.

FIELD OF THE INVENTION

This disclosure relates to novel conjugates of siRNAs and hydrophobic chains that are useful for RNA interference (RNAi). It has been found that a branched structure formed by either one or a plurality of hydrophobic chains in the conjugate can lead to unexpected results in terms of pharmacokinetic/pharmacodynamic behavior, tissue accumulation, and efficacy of the siRNA.

BACKGROUND

Small interfering RNAs (siRNAs) are an emerging class of drugs [1] that target disease-causing messenger RNA (mRNA) for degradation in a sequence-specific manner [2]. Therapeutic siRNAs are potent, have a long duration of effect, and are able to target previously "undruggable" disease genes [3-5]. However, they exhibit poor in vivo stability and distribution. To overcome these limitations, siRNAs are first chemically modified, then conjugated with diverse chemical moieties [6, 7]. Fully chemically modified siRNAs conjugated to a trivalent N-acetylgalactosamine (GalNAc) show functional delivery to hepatocytes in humans [8-12], and represent a major breakthrough in the therapeutic oligonucleotide field.

Lipid conjugation has also emerged as a delivery platform for siRNAs [6]. Sterols, fatty acids, and vitamins (with or without a phosphocholine moiety) conjugated to siRNAs have been shown to impact both local and systemic siRNA distribution [7, 13-17]. Lipid-conjugated siRNAs primarily accumulate in clearance tissues (liver, kidney, and spleen). Less hydrophobic compounds preferentially bind to high density lipoprotein (HDL) in serum and accumulate in kidneys, whereas more hydrophobic siRNAs primarily bind low density lipoprotein (LDL) and distribute to the liver [17, 18]. Lipophilic siRNAs also distribute to extrahepatic and extrarenal tissues, which may be influenced by conjugate configuration [17, 19, 20].

Lipid engineering may be a useful strategy for further enhancing siRNA delivery to specific tissues. Indeed, lipid branching and multi-valency approaches are used in the development of lipid-based nanocarriers with advanced properties [21-25]. However, we currently have a limited understanding of how lipid chemical structure and configuration impact siRNA pharmacokinetic/pharmacodynamic behavior, tissue accumulation, and efficacy.

SUMMARY

In a first aspect, the disclosure provides an siRNA-lipid conjugate represented by the following formula:

$$Y\text{-}L\text{-}(H)_n$$

wherein:
Y is an siRNA molecule,
L is a linker covalently bonded to Y and H,
each H is independently a hydrophobic chain comprising 5 to 50 carbon atoms,
n is 1, 2, or 3, and
linker L is bonded to the 3' end of the sense strand of the siRNA.

In an embodiment, the hydrophobic chain of at least one H is a linear or branched aliphatic chain comprising 10 to 30 carbon atoms.

In an embodiment, the hydrophobic chain of at least one H is derived from a linear or branched fatty acid and the carbonyl group of the fatty acid is attached to the linker by an amide bond. The fatty acid may be selected from the group consisting of myristic, docosahexaenoic, and eicosapentaenoic.

In an embodiment n is 2 and each H is independently an aliphatic chain comprising 12 to 26 carbon atoms.

In an embodiment, n is 1 and the H is a branched chain comprising 24 to 48 carbon atoms.

In an embodiment, the linker is attached to an H by a bond selected from the group consisting of an ester bond, an amide bond, an ether bond, a thioether bond, a nitrogen-carbon covalent bond, and combinations thereof.

In representative embodiments, the linker L comprises a structure selected from the group consisting of:

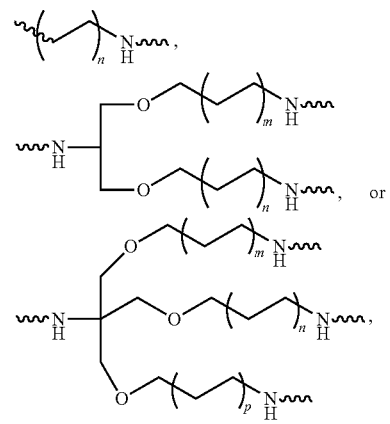

wherein each m, n, and p is a natural number independently selected from the group consisting of 1, 2, 3, 4, and 5.

In an embodiment, said siRNA comprises at least one modified nucleotide. The modified nucleotide may be chosen from the group of: a 2'-O-methyl modified nucleotide, a 2'-deoxy-2'-fluoro modified nucleotide, a nucleotide comprising a 5'-phosphorothioate group, and a terminal nucleotide linked to an E-vinylphosphate group. The modified nucleotide may also be chosen from the group of: a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.

In an embodiment, the siRNA comprises at least one 2'-O-methyl modified nucleotide, at least a 2'-deoxy-2'- fluoro modified nucleotide, and at least one nucleotide comprising a 5'-phosphorothioate group.

In an embodiment, at least 80% of the nucleotides of the siRNA are chemically modified.

In an embodiment, all the nucleotides of the siRNA are chemically modified. In an embodiment, the siRNA-lipid conjugate is such that:
(1) the sense strand of the siRNA molecule comprises alternating 2'-methoxy-ribonucleotides and 2'-fluoro-ribonucleotides;
(2) the antisense strand of the siRNA molecule comprises alternating 2'-methoxy-ribonucleotides and 2'-fluoro-ribonucleotides;
(3) the nucleotides of the sense strand are connected via phosphodiester or phosphorothioate linkages; and
(4) the nucleotides of the antisense strand are connected via phosphodiester or phosphorothioate linkages.

In a second aspect, the disclosure provides a pharmaceutical composition for inhibiting the expression of a gene in an organism, comprising an siRNA-lipid conjugate of the above first aspect of the disclosure and a pharmaceutically acceptable carrier.

In an embodiment, the amount of siRNA-lipid conjugate inhibits the expression of the gene by at least 50%.

In a third aspect, the disclosure provides a method of treating or managing a disease or disorder comprising administering to a patient in need of such treatment or management a therapeutically effective amount of an siRNA-lipid conjugate according to the above first aspect of the disclosure.

In a fourth aspect, the disclosure provides a method for delivering the siRNA-lipid conjugate according to any one of the embodiments of the above first aspect to an organ or tissue in a patient, comprising administering to the patient said compound, wherein the organ or tissue is selected from the group consisting of thymus, bladder, intestine, skin, bone marrow, placenta, adipose tissue, muscle, spleen, pancreas, lung, fallopian tube, adrenal gland, heart, liver and kidney.

BRIEF DESCRIPTION OF THE DRAWINGS

The foregoing and other features and advantages of the present invention will be more fully understood from the following detailed description of illustrative embodiments taken in conjunction with the accompanying drawings. The patent or application file contains at least one drawing executed in color. Copies of this patent or patent application publication with color drawing(s) will be provided by the Office upon request and payment of the necessary fee.

FIGS. 1A-1B illustrate a library of example fatty acid-conjugated siRNAs.

FIG. 1A is a schematic representation of example siRNA conjugates used in the present disclosure. The linker is attached at the 3'-end of the sense strand.

FIG. 1B depicts structures of the conjugates attached to the siRNAs: mono-(s); di- (d), and trivalent (t) with fatty acid chains (Myristic acid, Myr; Docosahexaenoic acid, DHA; Eicosapentaenoic acid, EPA).

FIG. 2A includes High Performance Liquid Chromatography (HPLC) spectra of conjugated Cy3-siRNA$^{Htt}$ sense strands showing variation in retention time (hydrophobicity) due to the nature and number of fatty acids FIG. 2B reports hydrodynamic diameters of lipid-conjugated siRNAs determined by Dynamic Light Scattering. Mean diameter for: unconjugated=2 nm; monovalent with a lipid chain=2.3-2.7 nm; divalent=3.6-4.2 nm; tri-substituted=10.1-11.7 nm.

FIG. 3A Mice were injected subcutaneously with Myr variant conjugated siRNAs (n=6, 20 mg/kg). Serial blood samples were collected through the lateral saphenous vein at different time points after injection over a 7-day period. Antisense strands in blood samples were quantified using PNA hybridization assay.

FIG. 3B Pharmacokinetic parameters for Myr variant conjugated siRNAs. AUC=area under the curve. MRT=mean residence time.

FIG. 4A includes representative fluorescence images of skin (injection site), kidney, and liver sections from mice injected subcutaneously (n=3, 20 mg/kg) with Myr variant Cy3-labeled siRNAs (red). Nuclei stained with DAPI (blue). Tissues were collected 48 h after injection. Images taken at 10× and 40× magnifications and collected at the same laser intensity and acquisition time. Scale, 1 mm (10×) and 50 μm (40×)

FIG. 4B is a bar graph showing siRNA quantification in skin (injection site), kidney (cortex), and liver measured by PNA hybridization assay (mean±SD).

FIGS. 7A-7D demonstrates that hydrophobicity does not fully explain differences in siRNA distribution and efficacy in vivo.

FIG. 7A includes high Performance Liquid Chromatography (HPLC) spectra of conjugated Cy3-siRNA$^{Htt}$ sense strands showing similar hydrophobicities between Myr-d, TS (tocopheryl succinate conjugate), and cholesterol-conjugated siRNA FIG. 7B is a bar graph showing siRNA quantification in skin (injection site), kidney (cortex), and liver for Myr-d, cholesterol and TS siRNAs, measured by PNA hybridization assay (3 mice per conjugate, mean±SD)

FIG. 7C is a bar graph showing the quantities of Myr d, cholesterol (chol.) and TS conjugated siRNAs present in 12 tissues at 48 h after a single subcutaneous injection with 20 mg/kg (n=3±SD). siRNA quantification was measured by PNA hybridization assay.

FIG. 7D reports the measurement of Huntingtin mRNA levels in mice injected subcutaneously with 20 mg/kg of Myr d, cholesterol or TS conjugated siRNA (n=6-8 per group, Ntc=non-targeting controls). The tissues were collected after 1 week and Huntingtin (Htt) mRNA levels were measured using QuantiGene®, normalized to a housekeeping gene, Hprt (Hypoxanthine-guanine phosphoribosyl transferase), and presented as percent of PBS control (mean±SD). Statistical analysis: One-way ANOVA with Bonferroni correction, *=P<0.1, =P<0.01, *=P<0.001.

FIG. 11A is a bar graph showing the percentages of the injected dose retained in tissues. The presence of lipids allows quantitative siRNA retention (mean±SD)

FIG. 11B is a bar graph showing the percentage of retained siRNA in liver, kidney, skin (injection site), and other tissues. The number of lipids defines the siRNA distribution. Subcutaneous injection (FVB/N mice, n=3; dose 20 mg/kg) and tissue collection after 48 h. Organ weights were measured or based on publications.

DETAILED DESCRIPTION OF CERTAIN EXEMPLARY EMBODIMENTS

Figure 2A:
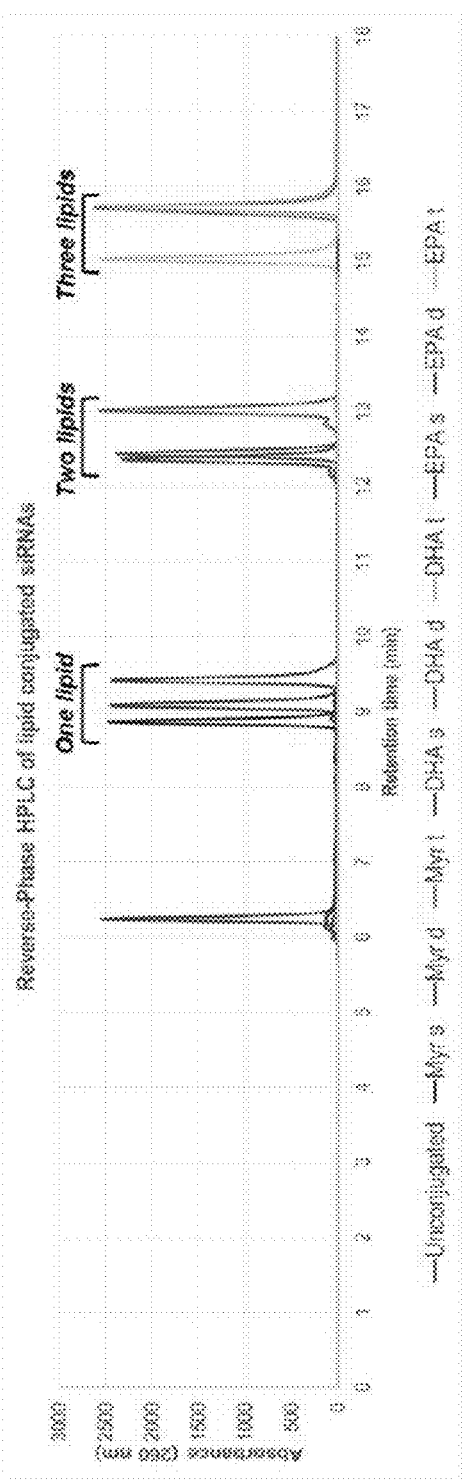
FIGS. 2A-2B demonstrate how the presence of fatty acids significantly impacts siRNA hydrophobicity and micelle formation.

Novel branched lipid conjugates of siRNA are provided herein. Also provided are methods of making the conjugates and their therapeutic formulations. Without being bound to any particular theory, it appears that although the hydrophobicity of a conjugate may affect siRNA clearance and distribution, the chemical nature/structure and self-association properties of siRNA conjugates drive cellular internalization and functional silencing. In representative embodiments, a conjugate of the application is of Formula (I):

Y-L-(H)$_n$          Formula (I)

Y is an siRNA molecule, L is a linker covalently bonded to Y and H, each H is independently a hydrophobic chain comprising 5 to 50 carbon atoms, n is 1, 2, or 3, and linker L is bonded to the 3' end of the sense strand of the siRNA.

Importantly, experimental findings reported herein show that conjugates having similar hydrophobicity but differing in terms of lipid chain branching exhibit unexpected patterns of tissue accumulation and distribution.

To evaluate the impact of lipid structure and valency on siRNA clearance, distribution, and efficacy, a panel of siRNAs conjugated to one, two, or three docosahexaenoic acid, eicosapentaenoic acid, or myristic acid chains were synthesized and tested. Altering fatty acid valency significantly impacted siRNA hydrophobicity, resulting in different clearance profiles: (i) trivalent lipid-conjugated siRNAs were retained at the injection site with minimal systemic exposure; (ii) monovalent lipid-conjugated siRNAs were quickly released to the circulation and predominantly accumulated in kidney tissue; and (iii) divalent lipid-conjugated siRNAs showed intermediate behavior, with preferential liver accumulation but wide distribution to other tissues (lung, heart, fat).

In addition to hydrophobicity, conjugate structure also contributed to the degree of tissue accumulation required for productive silencing. For example, conjugates featuring two myristic acid-derived chains showed lung accumulation levels ~3 times higher than other conjugated siRNAs of similar hydrophobicities, which resulted in productive silencing. The mechanism underlying enhanced lung delivery is unknown, but may be due to the impact of lipid branching on membrane fluidity, receptor interactions, and trafficking/endosomal escape. This study demonstrates that the valency of fatty acid conjugates is a strong determinant of the siRNA pharmacokinetic and distribution profiles in vivo. Thus, chemically engineering lipid-conjugated siRNA is a viable strategy for improving extrahepatic delivery and efficacy of therapeutic siRNAs.

Definitions

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including", as well as other forms, such as "includes" and "included," is not limiting. As used herein, unless otherwise stated, the singular forms "a," "an," and "the" include plural reference. Thus, for example, a reference to "a protein" includes a plurality of protein molecules.

Unless otherwise defined herein, nomenclatures used in connection with cell and tissue culture, molecular biology, immunology, microbiology, genetics, protein and nucleic acid chemistry and hybridization described herein are those well-known and commonly used in the art. The methods and techniques provided herein are unless otherwise specified herein performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

The term "complementary" refers to the relationship between nucleotides exhibiting Watson-Crick base pairing, or to oligonucleotides that hybridize via Watson-Crick base pairing to form a double-stranded nucleic acid. The term "complementarity" refers to the state of an oligonucleotide (e.g., a sense strand or an antisense strand) that is partially or completely complementary to another oligonucleotide. Oligonucleotides described herein as having complementarity to a second oligonucleotide may be 100%, >95%, >90%, >85%, >80%, >75%, >70%, >65%, >60%, >55% or >50% complementary to the second oligonucleotide.

As used herein in the context of oligonucleotide sequences, "A" represents a nucleoside comprising the base adenine (e.g., adenosine or a chemically-modified derivative thereof), "G" represents a nucleoside comprising the base guanine (e.g., guanosine or a chemically-modified derivative thereof), "U" represents a nucleoside comprising the base uracil (e.g., uridine or a chemically-modified derivative thereof), and "C" represents a nucleoside comprising the base cytosine (e.g., cytidine or a chemically-modified derivative thereof).

As used herein, the term "3' end" refers to the end of a nucleic acid that contains an unmodified hydroxyl group at the 3' carbon of its ribose ring.

As used herein, the term "5' end" refers to the end of a nucleic acid that contains a phosphate group attached to the 5' carbon of its ribose ring.

As used herein, the term "nucleoside" refers to a molecule made up of a heterocyclic base and its sugar.

As used herein, the term "nucleotide" refers to a nucleoside having a phosphate group on its 3' or 5' sugar hydroxyl group.

An RNAi agent, e.g., an siRNA, having a strand which is "sequence sufficiently complementary to a target mRNA sequence to direct target-specific RNA interference (RNAi)" means that the strand has a sequence sufficient to trigger the destruction of the target mRNA by RNAi.

As used herein, the term "isolated RNA" (e.g., "isolated siRNA," "isolated siRNA" or "isolated siRNA precursor") refers to an RNA molecule that is substantially free of other cellular material, or culture medium when produced by recombinant techniques, or substantially free of chemical precursors or other chemicals when chemically synthesized.

The term "discriminatory RNA silencing" refers to the ability of an RNA molecule to substantially inhibit the expression of a "first" or "target" polynucleotide sequence while not substantially inhibiting the expression of a "second" or "non-target" polynucleotide sequence, e.g., when both polynucleotide sequences are present in the same cell. In certain embodiments, the target polynucleotide sequence corresponds to a target gene, while the non-target polynucleotide sequence corresponds to a non-target gene. In other embodiments, the target polynucleotide sequence corresponds to a target allele, while the non-target polynucleotide sequence corresponds to a non-target allele. In certain embodiments, the target polynucleotide sequence is the DNA sequence encoding the regulatory region (e.g. promoter or enhancer elements) of a target gene. In other embodiments, the target polynucleotide sequence is a target mRNA encoded by a target gene.

As used herein, the term "siRNA" refers to small interfering RNAs that induce the RNA interference (RNAi) pathway. siRNA molecules can vary in length (usually between 18-30 base pairs) and contain varying degrees of complementarity to their target mRNA. The term "siRNA" includes duplexes of two separate strands, as well as single strands that can form hairpin structures comprising a duplex region.

As used herein, the term "antisense strand" refers to the strand of an siRNA duplex that contains some degree of complementarity to a target gene or mRNA and contains complementarity to the sense strand of the siRNA duplex.

As used herein, the term "sense strand" refers to the strand of an siRNA duplex that contains complementarity to the antisense strand of the siRNA duplex.

As used herein, the term "overhang" or "tail" refers to 3, 4, 5, 6, 7, 8, 9, 10, 11, 12, 13, 14, 15, 16, 17, 18, 19, 20 or more sequential nucleotides at the 3' end of one or both of the sense strand and the antisense strand that are single-stranded, i.e., are not base paired to (i.e., do not form a duplex with) the other strand of the siRNA duplex.

As used herein, the term "antisense oligonucleotide" or "ASO" refers to a nucleic acid (e.g., an RNA), having sufficient sequence complementarity to a target an RNA (e.g., a SNP-containing mRNA or a SNP-containing pre-mRNA) in order to block a region of a target RNA in an effective manner, e.g., in a manner effective to inhibit translation of a target mRNA and/or splicing of a target pre-mRNA. An antisense oligonucleotide having a "sequence sufficiently complementary to a target RNA" means that the antisense agent has a sequence sufficient to mask a binding site for a protein that would otherwise modulate splicing and/or that the antisense agent has a sequence sufficient to mask a binding site for a ribosome and/or that the antisense agent has a sequence sufficient to alter the three-dimensional structure of the targeted RNA to prevent splicing and/or translation.

In certain exemplary embodiments, an siRNA conjugate of the present application is asymmetric. In certain exemplary embodiments, an siRNA conjugate of the present application is symmetric.

In certain exemplary embodiments, an siRNA conjugate of the present application comprises a duplex region of between about 8-20 nucleotides or nucleotide analogs in length, between about 10-18 nucleotides or nucleotide analogs in length, between about 12-16 nucleotides or nucleotide analogs in length, or between about 13-15 nucleotides or nucleotide analogs in length (e.g., a duplex region of about 8, 9, 10, 11, 12, 13, 14, 15, 16, 17, 18, 19 or 20 base pairs).

In certain exemplary embodiments, an siRNA conjugate of the present application comprises one or two overhangs. In certain embodiments, each overhang of the siRNA comprises at least about 3, about 4, about 5, about 6, about 7, about 8, about 9, or about 10 sequential nucleotides. In certain embodiments, each overhang of the siRNA conjugate of the present application is about 4, about 5, about 6 or about 7 nucleotides in length. In certain embodiments, the sense strand overhang is the same number of nucleotides in length as the antisense strand overhang. In other embodiments, the sense strand overhang has fewer nucleotides than the antisense strand overhang. In other embodiments, the antisense strand overhang has fewer nucleotides than the sense strand overhang.

In certain exemplary embodiments, an siRNA conjugate of the present application comprises a sense strand and/or an antisense strand each having a length of about 10, about 15, about 20, about 25 or about 30 nucleotides. In certain embodiments, an siRNA conjugate of the present application comprises a sense strand and/or an antisense strand each having a length of between about 15 and about 25 nucleotides. In some embodiments, an siRNA conjugate of the present application comprises a sense strand and an antisense strand that are each about 20 nucleotides in length. In certain embodiments, the sense strand and the antisense strand of an siRNA are the same length. In other embodiments, the sense strand and the antisense strand of an siRNA are different lengths.

In certain exemplary embodiments, an siRNA conjugate of the present application has a total length (from the 3' end of the antisense strand to the 3' end of the sense strand) of about 20, about 25, about 30, about 35, about 40, about 45, about 50 or about 75 nucleotides. In certain exemplary embodiments, an siRNA conjugate of the present application has a total length of between about 15 and about 35 nucleotides. In other exemplary embodiments, the siRNA conjugate of the present application has a total length of between about 20 and about 30 nucleotides. In other exemplary embodiments, the siRNA conjugate of the present application has a total length of between about 22 and about 28 nucleotides. In particular embodiments, an siRNA conjugate of the present application has a total length of about 20, about 21, about 22, about 23, about 24, about 25, about 26, about 27, about 28, about 29 or about 30 nucleotides.

As used herein, the terms "chemically modified nucleotide" or "nucleotide analog" or "altered nucleotide" or "modified nucleotide" refer to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example, the 2' OH-group may be replaced by a group selected from H, OR, R, F, Cl, Br, I, SH, SR, NH2, NHR, $NR_2$, or COOR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

As used herein, the term "metabolically stabilized" refers to RNA molecules that contain 2'-ribose modifications to replace native 2'-hydroxyl groups with 2'-O-methyl groups or 2'-fluoro groups. In some embodiments, the duplex region of an siRNA comprises one or two 2'-fluoro modifications and/or at least about 86%, at least about 87%, at least about 88%, at least about 89%, at least about 90%, at least about 91%, at least about 92%, at least about 93% or at least about 94% 2'-methoxy modifications. In certain exemplary embodiments, the antisense strand comprises two 2'-fluoro modifications and at least about 90%, at least about 91%, at least about 92%, at least about 93% or at least about 94% 2'-methoxy modifications. In certain exemplary embodiments, the sense strand comprises at least about 91%, at least about 92%, at least about 93%, at least about 94%, at least about 95%, at least about 96%, at least about 97%, at least about 98%, at least about 99% or about 100% 2'-methoxy modifications. In certain exemplary embodiments, a single-stranded RNA is provided that comprises two 2'-fluoro modifications and at least about 90%, at least about 91%, at least about 92%, at least about 93% or at least about 94% 2'-methoxy modifications.

In a particularly exemplary embodiment, an siRNA is provided that comprises a 2'-fluoro modification at the nucleotide at each of positions 2 and 14 from the 5' end, and a 2'-methoxy modification at each other nucleotide position.

As used herein, the term "phosphorothioate" refers to the phosphate group of a nucleotide that is modified by substituting one or more of the oxygens of the phosphate group with sulfur. A phosphorothioate further comprises a cationic counter-ion (e.g., sodium, potassium, calcium, magnesium or the like). The term "phosphorothioated nucleotide" refers to a nucleotide having one or two phosphorothioate linkages to another nucleotide. In certain embodiments, the single-stranded tails of the siRNAs of the conjugate comprise or consist of phosphorothioated nucleotides.

In some embodiments, the compounds, oligonucleotides and nucleic acids described herein may be modified to comprise one or more internucleotide linkages provided in FIG. 3. In particular embodiments, the compounds, oligonucleotides and nucleic acids described herein comprise one or more internucleotide linkages selected from phosphodiester and phosphorothioate.

It is understood that certain internucleotide linkages provided herein, including, e.g., phosphodiester and phosphorothioate, comprise a formal charge of −1 at physiological pH, and that said formal charge will be balanced by a cationic moiety, e.g., an alkali metal such as sodium or potassium, an alkali earth metal such as calcium or magnesium, or an ammonium or guanidinium ion.

The individual components forming the conjugate are described in further detail in the following subsections.

siRNA Design

In some embodiments, an siRNA molecule of the conjugate is a duplex consisting of a sense strand and complementary antisense strand, the antisense strand having sufficient complementary to an mRNA to mediate RNAi. In certain exemplary embodiments, the siRNA molecule has a length from about 10-50 or more nucleotides, i.e., each strand comprises 10-50 nucleotides (or nucleotide analogs or combinations of nucleotides and nucleotide analogs). In other exemplary embodiments, the siRNA molecule has a length from about 16-30, e.g., 16, 17, 18, 19, 20, 21, 22, 23, 24, 25, 26, 27, 28, 29, or 30 nucleotides in each strand, wherein one of the strands is sufficiently complementary to a target region to mediate RNAi. In certain exemplary embodiments, the strands are aligned such that there are at least 4, 5, 6, 7, 8, 9, 10 or more bases at the end of the strands do not align (i.e., for which no complementary bases occur in the opposing strand) such that an overhang of 4, 5, 6, 7, 8, 9, 10 or more residues occurs at each of or both ends of the duplex when strands are annealed. In certain exemplary embodiments, the siRNA molecule has a length from about 10-50 or more nucleotides, i.e., each strand comprises 10-50 nucleotides (or nucleotide analogs or combinations of nucleotides and nucleotide analogs). In some exemplary embodiments, the siRNA molecule has a length from about 16-30, e.g., 16, 17, 18, 19, 20, 21, 22, 23, 24, 25, 26, 27, 28, 29, or 30 nucleotides in each strand, wherein one of the strands is substantially complementary to a target sequence, and the other strand is identical or substantially identical to the first strand.

Generally, siRNAs can be designed by using any method known in the art, for instance, by using the following protocol:

1. The siRNA should be specific for a target sequence. The first strand should be complementary to the target sequence, and the other strand is substantially complementary to the first strand. Exemplary target sequences are selected from the 5' untranslated region (5'-UTR) or an intronic region of a target gene. Cleavage of mRNA at these sites should eliminate translation of corresponding mutant protein. Target sequences from other regions of a target gene are also suitable for targeting. A sense strand is designed based on the target sequence. Further, siRNAs with lower G/C content (35-55%) may be more active than those with G/C content higher than 55%. Thus, in one embodiment, the invention includes nucleic acid molecules having 35-55% G/C content.

2. The sense strand of the siRNA is designed based on the sequence of the selected target site. In certain exemplary embodiments, the sense strand includes about 19 to 25 nucleotides, e.g., 19, 20, 21, 22, 23, 24 or 25 nucleotides. In particularly exemplary embodiments, the sense strand includes 19, 20 or 21 nucleotides. The skilled artisan will appreciate, however, that siRNAs having a length of less than 19 nucleotides, e.g., a length of 13, 14, 15, 16, 17 or 18 nucleotides, or greater than 25 nucleotides, can also function to mediate RNAi. Accordingly, siRNAs of such length are also within the scope of the instant invention provided that they retain the ability to mediate RNAi. Longer RNA silencing agents have been demonstrated to elicit an interferon or Protein Kinase R (PKR) response in certain mammalian cells, which may be undesirable. In certain exemplary embodiments, the siRNA conjugates of the invention do not elicit a PKR response (i.e., are of a sufficiently short length). However, longer RNA silencing agents may be useful, for example, in cell types incapable of generating a PRK response or in situations where the PKR response has been down-regulated or dampened by alternative means.

The siRNA molecules of the conjugate have sufficient complementarity with the target sequence such that the siRNA can mediate RNAi. In general, siRNA containing nucleotide sequences sufficiently identical to a target sequence portion of the target gene to effect RISC-mediated cleavage of the target gene are particularly suitable. Accordingly, in an exemplary embodiment, the sense strand of the siRNA is designed to have a sequence sufficiently identical to a portion of the target. For example, the sense strand may have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is particularly suitable. The invention has the advantage of being able to tolerate certain sequence variations to enhance efficiency and specificity of RNAi. In one embodiment, the sense strand has 4, 3, 2, 1, or 0 mismatched nucleotide(s) with a target region, such as a target region that differs by at least one base pair between a wild-type and mutant allele, e.g., a target region comprising the gain-of-function mutation, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., percent (%) homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). An exemplary, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). An exemplary non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA is routinely the same length as the sense strand and includes complementary nucleotides. In one embodiment, the strands of the siRNA are paired in such a way as to have a 3' overhang of 4 to 15, e.g., 4, 5, 6 or 7 nucleotides. In certain embodiments, the antisense or guide strand of the siRNA is longer than the sense strand.

4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

5. Select one or more sequences that meet your criteria for evaluation.

Further general information about the design and use of siRNA may be found in "The siRNA User Guide," available at The Max-Plank-Institut fur Biophysikalishe Chemie website.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional exemplary hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m(° C.)=2(\# \text{ of A+T bases})+4(\# \text{ of G+C bases})$. For hybrids between 18 and 49 base pairs in length, $T_m(° C.)=81.5+16.6(\log 10[Na+])+0.41(\% G+C)-(600/N)$, where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Negative control siRNA should have the same nucleotide composition as the selected siRNA, but without significant sequence complementarity to the appropriate genome. Such negative controls may be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

6. To validate the effectiveness by which siRNAs destroy target mRNAs (e.g., wild-type or mutant target mRNA), the siRNA may be incubated with target cDNA in a *Drosophila*-based in vitro mRNA expression system. Radiolabeled with $^{32}$P, newly synthesized target mRNAs are detected autoradiographically on an agarose gel. The presence of cleaved target mRNA indicates mRNA nuclease activity. Suitable controls include omission of siRNA and use of non-target cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

Modified siRNAs

In certain aspects of the invention, the siRNA component of the conjugate (or any portion thereof) may be modified such that its activity is further improved. For example, the siRNA may be modified with any of the modifications described herein. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

In representative embodiments, at least 10%, 20%, 30%, 40%, 50%, 60%, 70%, 80%, 90%, or all the nucleotides of the siRNA component are chemically modified.

1) Modifications to Enhance Target Discrimination

In certain embodiments, the siRNAs of the conjugate may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the siRNA for a non-target mRNA (e.g. wild-type mRNA), without appreciably affecting the specificity of the siRNA for a target mRNA (e.g. gain-of-function mutant mRNA).

In certain exemplary embodiments, the siRNAs of the conjugate are modified by the introduction of at least one universal nucleotide in the antisense strand thereof Universal nucleotides comprise base portions that are capable of base pairing indiscriminately with any of the four conventional nucleotide bases (e.g. A, G, C, U). A universal nucleotide is particularly suitable because it has relatively minor effect on the stability of the RNA duplex or the duplex formed by the guide strand of the siRNA conjugate and the target mRNA. Exemplary universal nucleotides include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholino-inosine, LNA-inosine, phosphoramidate-inosine, 2'-O-methoxyethyl-inosine, and 2'-OMe-inosine. In particularly exemplary embodiments, the universal nucleotide is an inosine residue or a naturally occurring analog thereof.

In certain embodiments, the siRNAs of the conjugate are modified by the introduction of at least one destabilizing nucleotide within 5 nucleotides from a specificity-determining nucleotide (i.e., the nucleotide which recognizes the disease-related polymorphism). For example, the destabilizing nucleotide may be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destablilizing nucleotide and the specificity-determining nucleotide). The destabilizing nucleotide may be introduced in the strand or strand portion that does not contain the specificity-determining nucleotide. In certain exemplary embodiments, the destabilizing nucleotide is introduced in the same strand or strand portion that contains the specificity-determining nucleotide.

2) Modifications to Enhance Efficacy and Specificity

In certain embodiments, the siRNAs of the conjugate may be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., an siRNA designed using the methods of the invention or an siRNA produced from a shRNA) into RISC in favor of the sense strand, such that the antisense strand preferentially guides cleavage or translational repression of a target mRNA, and thus increasing or improving the efficiency of target cleavage and silencing. In some embodiments, the asymmetry of an siRNA conjugate is enhanced by lessening the base pair strength between the antisense strand 5' end (AS 5') and the sense strand 3' end (S 3') of the siRNA conjugate relative to the bond strength or base pair strength between the antisense strand 3' end (AS 3') and the sense strand 5' end (S '5) of said siRNA conjugate.

In one embodiment, the asymmetry of the siRNA of the conjugate may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an siRNA may be enhanced such that there is at least one mismatched base pair between the 5' end of the first or antisense strand and the 3' end of the sense strand portion. In certain exemplary embodiments, the mismatched base pair is selected from the group consisting of G:A, C:A, C:U, G:G, A:A, C:C and U:U. In other embodiments, the asymmetry of an siRNA of the conjugate may be enhanced such that there is at least one wobble base pair, e.g., G:U, between the 5' end of the first or antisense strand and the 3' end of the sense strand portion. In other embodiments, the asymmetry of an siRNA may be enhanced such that there is at least one base pair comprising a rare nucleotide, e.g., inosine (I). In certain exemplary embodiments, the base pair is selected from the group consisting of an I:A, I:U and I:C. In yet another embodiment, the asymmetry of an siRNA of the conjugate may be enhanced such that there is at least one base pair comprising a modified nucleotide. In certain exemplary embodiments, the modified nucleotide is selected from the group consisting of 2-amino-G, 2-amino-A, 2,6-di-amino-G, and 2,6-diamino-A.

3) siRNA Conjugates with Enhanced Stability

The siRNAs described herein (and other RNA silencing agents) can be further modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In an exemplary aspect, the invention features siRNAs that include first and second strands wherein the second strand and/or first strand is modified by the substitution of internal nucleotides with modified nucleotides, such that in vivo stability is enhanced as compared to a corresponding unmodified siRNA. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In an exemplary embodiment of the present invention, the siRNAs may contain at least one modified nucleotide analogue. The nucleotide analogues may be located at positions where the target-specific silencing activity, e.g., the RNAi mediating activity or translational repression activity is not substantially affected, e.g., in a region at the 5'-end and/or the 3'-end of the siRNA. Particularly, the ends may be stabilized by incorporating modified nucleotide analogues.

Exemplary nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides, the phosphoester group connecting to adjacent ribonucleotides is replaced by a modified group, e.g., of phosphothioate group. In exemplary sugar-modified ribonucleotides, the 2' OH-group is replaced by a group selected from H, OR, R, halo, SH, SR, NH2, NHR, $NR_2$ or ON, wherein R is $C_1$-$C_6$ alkyl, alkenyl or alkynyl and halo is F, Cl, Br or I. Examples of suitable sugar modifications according to certain exemplary embodiments are shown at FIG. 2.

In particular embodiments, the modifications are 2'-fluoro, 2'-amino and/or 2'-thio modifications. Particular exemplary modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, and/or 5-amino-allyl-uridine. In a particular embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-OMe nucleotides can also be used within modified RNA-silencing agents moieties of the instant invention. Additional modified residues include, deoxy-abasic, inosine, N3-methyl-uridine, N6, N6-dimethyl-adenosine, pseudouridine, purine ribonucleoside and ribavirin. In certain exemplary embodiments, the 2' moiety is a methyl group such that the linking moiety is a 2'-O-methyl oligonucleotide.

In an exemplary embodiment, an siRNA comprises Locked Nucleic Acids (LNAs). LNAs comprise sugar-modified nucleotides that resist nuclease activities (are highly stable) and possess single nucleotide discrimination for mRNA (Elmen et al., Nucleic Acids Res., (2005), 33(1): 439-447; Braasch et al. (2003) Biochemistry 42:7967-7975, Petersen et al. (2003) Trends Biotechnol. 21:74-81). These molecules have 2'-0,4'-C-ethylene-bridged nucleic acids, with possible modifications such as 2'-deoxy-2"-fluorouridine. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base.

Also exemplified are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

Other exemplary modifications include: (a) 2' modification, e.g., provision of a 2'-OMe moiety on a U in a sense or antisense strand, but especially on a sense strand, or provision of a 2'-OMe moiety in a 3' overhang, e.g., at the 3' terminus (3' terminus means at the 3' atom of the molecule or at the most 3' moiety, e.g., the most 3' P or 2' position, as indicated by the context); (b) modification of the backbone, e.g., with the replacement of an O with an S, in the phosphate backbone, e.g., the provision of a phosphorothioate modification that forms a phosphorothioate linkage, on the U or the A or both, especially on an antisense strand; e.g., with the replacement of a P with an S; (c) replacement of the U with a C5 amino linker; (d) replacement of an A with a G (in particular embodiments sequence changes are located on the sense strand and not the antisense strand); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2'-OMe moiety and modification of the backbone, e.g., with the replacement of a P with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus.

Hydrophobic Chains

As set out above, the siRNA is conjugated through the linker to one or more hydrophobic chain moieties. In one embodiment, the siRNA is conjugated to one hydrophobic chain, and is herein defined as being "monovalent". In another embodiment, the siRNA is conjugated to two hydrophobic chains, and is herein defined as being "divalent". In a further embodiment, the siRNA is conjugated to three hydrophobic chains, and is herein defined as being "trivalent". Hence, an siRNA-lipid conjugate may be defined in terms of its "valency", which in the context of the present application is intended to mean the number of hydrophobic chain moieties attached to the linker, for example to suit a desired siRNA tissue distribution profile for treating a given condition or disease. In instances where the valency is equal to two or more than two, the chains may be the same or different from each other.

In a representative embodiment, each hydrophobic chain may independently contain 5 to 50 carbon atoms. In another embodiment, each hydrophobic chain may independently contain 10 to 30 carbon atoms. In a further embodiment, each hydrophobic chain may independently contain 12 to 26 carbon atoms. In an embodiment, the hydrophobic chains are aliphatic. An aliphatic chain contains carbon atoms substituted with hydrogen and joined together in straight chains or branched chains. Aliphatic chains may contain single or double carbon-carbon bonds. In other words, they may be saturated or unsaturated. Representative, non-limiting example aliphatic chains containing 10 to 30 carbon atoms and, if unsaturated, may contain 1 to 10 unsaturations.

The aliphatic chain(s) of the conjugate may be straight or branched, emphasis being placed on conjugate valency and chain chemical structures that yield conjugates having improved properties as measured by metrics such as the desired hydrodynamic diameter, pharmacokinetic behavior, and/or tissue accumulation and distribution. In one example embodiment, the conjugate includes two linear chains each independently including 12 to 26 carbon atoms, giving rise to a branched structure. In another embodiment, the conjugate features a single, branched chain including 24 to 48 carbon atoms that may achieve a branched structure analogous to that obtained with two separate straight chains. In a further embodiment, one or more of the hydrogen atoms of the aliphatic chain(s) may be replaced with one or more independently selected substituent moieties, for example —F, —Cl, —Br, I —OH, —NH2, —SH, —COOH, —OR, —NHR, —NR$_2$, —SR, or —COOR, wherein R is $C_1$-$C_6$ alkyl, alkenyl, or alkynyl, provided that the number and nature of the selected substituent(s) do not negatively affect the properties of the conjugate.

In a non-limiting embodiment, an aliphatic chain may be derived from a fatty acid, for example a linear saturated fatty acid of formula $CH_3$—$(CH_2)_n$—$CO_2H$ with n=10 to 30, or a linear alkyl halide of formula $CH_3$-$(CH_2)_n$—X with n=10 to 30, although chains bearing one or more unsaturations are also contemplated. When the hydrophobic chain is derived from a fatty acid the —COOH moiety of the fatty acid may form a covalent bond with an —NH$_2$ or an —OH moiety of the linker, forming an amide bond or ester bond. When the lipid chain is derived from an alkyl halide as defined above, its connection with the linker may also be achieved by reacting with an —OH or —NH$_2$ moiety of the linker, forming an ether or carbon-nitrogen bond. The alkyl halide may also be reacted with a —SH moiety of the linker, preferably forming a thioether bond.

Linker

In representative embodiments, the linker is covalently bound to both the siRNA molecule and hydrophobic chain(s), thereby forming a conjugate. In one embodiment, the structure and size of the linker is such that the siRNA molecule is prevented from degrading a desired property or activity of the hydrophobic chains, and vice versa. In one example embodiment, the linker is attached to one or both strands of an siRNA. In another exemplary embodiment, the lipophilic moiety is attached to the 3' end of the sense strand. Similarly, the linker may be bound to each hydrophobic chain by one or more covalent bonds. In one embodiment, the linker is a diol, triol, or tetrol derivative. In another embodiment, the linker is a di-, tri- or tetra-carboxylic acid derivative. In another embodiment, the linker is a di-amine derivative. In a further embodiment, the linker is a tri- or tetra-amine derivative. In an additional embodiment, the linker is a di-thiol, tri-thiol, or tetra-thiol derivative. Also contemplated are linkers derived from species comprising a combination of hydroxyl, thiol, amino, and/or carboxyl moieties.

In an example embodiment, the linker of a monovalent conjugate includes a structure of Formula (II):

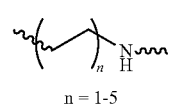

Formula (I)

n = 1-5

In another exemplary embodiment, the linker of a divalent conjugate includes a structure of Formula (III):

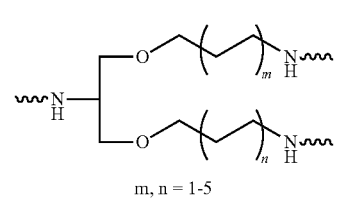

Formula (II)

m, n = 1-5

In a further example embodiment, the linker of a trivalent conjugate includes a structure of Formula (III):

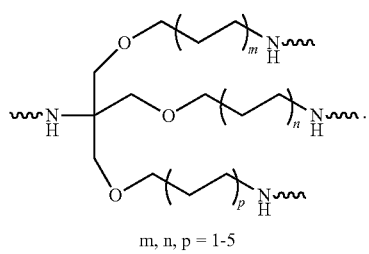

Formula (III)

m, n, p = 1-5

Pharmaceutical Compositions and Methods of Administration

In a further aspect, provided herein is a pharmaceutical composition comprising a therapeutically effective amount of one or more siRNA conjugates as described herein, and a pharmaceutically acceptable carrier. This aspect of the invention pertains to uses of the above-described conjugates for prophylactic and/or therapeutic treatments as described herein. Accordingly, the conjugates of the present invention can be incorporated into pharmaceutical compositions suitable for administration. Such compositions typically include a conjugate and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous (IV), intradermal, subcutaneous (SC or SQ), intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents are included, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, exemplary methods of preparation are vacuum drying and freeze-drying, which yields a powder of the active ingredient plus any additional desired ingredient from a previously sterile-filtered solution thereof.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index, which is expressed as the ratio LD50/ED50. Compounds that exhibit large therapeutic indices are particularly suitable. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies typically within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

Methods of Treatment

In one aspect, the present invention provides for both prophylactic and therapeutic methods of treating a subject at risk of (or susceptible to) a disease or disorder.

"Treatment," or "treating," as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one embodiment, the invention provides a method for preventing in a subject, a disease or disorder as described above, by administering to the subject a therapeutic siRNA conjugate. Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the invention pertains to methods treating subjects therapeutically, i.e., alter onset of symptoms of the disease or disorder. In an exemplary embodiment, the modulatory method of the invention involves contacting a cell expressing a gain-of-function mutant with a therapeutic agent (e.g., an siRNA conjugate) that is specific for one or more target sequences within the gene, such that sequence specific interference with the gene is achieved. These methods can be performed in vitro (e.g., by culturing the cell with the agent) or, alternatively, in vivo (e.g., by administering the agent to a subject).

For example, an siRNA conjugated for enhanced uptake into neural cells can be administered at a unit dose less than about 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmol of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of siRNA conjugate per kg of bodyweight. The unit dose, for example, can be administered by injection (e.g., intravenous or intramuscular, intrathecally, or directly into the brain), an inhaled dose, or a topical application. Suitable dosages are less than 2, 1, or 0.1 mg/kg of body weight.

Delivery of an siRNA conjugate directly to an organ can be at a dosage on the order of about 0.00001 mg to about 3 mg per organ, or about 0.0001-0.001 mg per organ, about 0.03-3.0 mg per organ, about 0.1-3.0 mg per eye or about 0.3-3.0 mg per organ. The dosage can be an amount effective to inhibit the expression of one or more genes by at least 30%, 50%, 70%, 80%, 90%, or even 100%, for example prevent, treat, or manage a neurodegenerative disease or disorder. In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. In one embodiment, the effective dose is administered with other traditional therapeutic modalities.

In one embodiment, a subject is administered an initial dose, and one or more maintenance doses of an siRNA conjugate. The maintenance dose or doses are generally lower than the initial dose, e.g., one-half less of the initial dose. A maintenance regimen can include treating the subject with a dose or doses ranging from 0.01 µg to 1.4 mg/kg of body weight per day, e.g., 10, 1, 0.1, 0.01, 0.001, or 0.00001 mg per kg of bodyweight per day. The maintenance doses are typically administered no more than once every 5, 10, or 30 days. Further, the treatment regimen may last for a period of time which will vary depending upon the nature of the particular disease, its severity and the overall condition of the patient. In certain exemplary embodiments, the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable. In one embodiment, a pharmaceutical composition includes a plurality of siRNA conjugate species. In another embodiment, the siRNA conjugate species has sequences that are non-overlapping and non-adjacent to another species with respect to a naturally occurring target sequence. In another embodiment, the plurality of siRNA conjugate species is specific for different naturally occurring target genes. In another embodiment, the siRNA is allele specific. In another embodiment, the plurality of siRNA conjugate species target two or more target sequences (e.g., two, three, four, five, six, or more target sequences). Genomic sequence for each target sequence can be found in, for example, the publicly available database maintained by the NCBI.

Following successful treatment, it may be desirable to have the patient undergo maintenance therapy to prevent the recurrence of the disease state, wherein the compound of the invention is administered in maintenance doses, ranging from 0.01 µg to 100 g per kg of body weight (see U.S. Pat. No. 6,107,094).

In another aspect, provided herein is a method of treating or managing a disease or disorder comprising administering to a patient in need of such treatment or management a therapeutically effective amount of an siRNA conjugate, or a pharmaceutical composition comprising said conjugate.

In certain exemplary embodiments, a composition that includes an siRNA conjugate of the invention can be delivered to the nervous system of a subject by a variety of routes. Exemplary routes include intrathecal, parenchymal (e.g., in the brain), nasal, and ocular delivery. The composition can also be delivered systemically, e.g., by intravenous, subcutaneous or intramuscular injection, which is particularly useful for delivery of siRNA conjugates to peripheral neurons. An exemplary route of delivery is directly to the brain, e.g., into the ventricles or the hypothalamus of the brain, or into the lateral or dorsal areas of the brain. The siRNA conjugate(s) for neural cell delivery can be incorporated into pharmaceutical compositions suitable for administration.

For example, compositions can include one or more species of an siRNA conjugate and a pharmaceutically acceptable carrier. The pharmaceutical compositions of the present invention may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, intrathecal, or intraventricular (e.g., intracerebroventricular) administration. In certain exemplary embodiments, an siRNA of the invention is delivered across the Blood-Brain-Barrier (BBB) in a variety of suitable compositions and methods described herein.

The route of delivery can be dependent on the disorder of the patient. In addition to an siRNA conjugate of the present application, a patient can be administered a second therapy, e.g., a palliative therapy and/or disease-specific therapy. The secondary therapy can be, for example, symptomatic (e.g., for alleviating symptoms), protective (e.g., for slowing or halting disease progression), or restorative (e.g., for reversing the disease process).

An siRNA conjugate can be delivered to neural cells of the brain. Delivery methods that do not require passage of the composition across the blood-brain barrier can be utilized. For example, a pharmaceutical composition containing an siRNA conjugate can be delivered to the patient by injection directly into the area containing the disease-affected cells. For example, the pharmaceutical composition can be delivered by injection directly into the brain. The injection can be by stereotactic injection into a particular region of the brain (e.g., the substantia nigra, cortex, hippocampus, striatum, or globus pallidus). The siRNA conjugate can be delivered into multiple regions of the central nervous system (e.g., into multiple regions of the brain, and/or into the spinal cord). The siRNA conjugate can be delivered into diffuse regions of the brain (e.g., diffuse delivery to the cortex of the brain).

In one embodiment, the siRNA conjugate can be delivered by way of a cannula or other delivery device having one end implanted in a tissue, e.g., the brain, e.g., the substantia nigra, cortex, hippocampus, striatum or globus pallidus of the brain. The cannula can be connected to a reservoir of siRNA conjugate. The flow or delivery can be mediated by a pump, e.g., an osmotic pump or minipump, such as an Alzet pump (Durect, Cupertino, Calif.). In one embodiment, a pump and reservoir are implanted in an area distant from the tissue, e.g., in the abdomen, and delivery is effected by a conduit leading from the pump or reservoir to the site of release. Devices for delivery to the brain are described, for example, in U.S. Pat. Nos. 6,093,180, and 5,814,014.

In certain embodiments, exosomes are used to deliver an siRNA conjugate. Exosomes can cross the BBB and deliver siRNAs, antisense oligonucleotides, chemotherapeutic agents and proteins specifically to neurons after systemic injection (See, Alvarez-Erviti L, Seow Y, Yin H, Betts C, Lakhal S, Wood M J. (2011). Delivery of siRNA to the mouse brain by systemic injection of targeted exosomes. Nat Biotechnol. 2011 April; 29(4):341-5. doi: 10.1038/nbt.1807; El-Andaloussi S, Lee Y, Lakhal-Littleton S, Li J, Seow Y, Gardiner C, Alvarez-Erviti L, Sargent I L, Wood M J. (2011). Exosome-mediated delivery of siRNA in vitro and in vivo. Nat Protoc. 2012 December; 7(12):2112-26. doi: 10.1038/nprot.2012.131; E L Andaloussi S, Mager I, Breakefield X O, Wood M J. (2013). Extracellular vesicles: biology and emerging therapeutic opportunities. Nat Rev Drug Discov. 2013 May; 12(5):347-57. doi: 10.1038/nrd3978; El Andaloussi S, Lakhal S, Mager I, Wood M J. (2013). Exosomes for targeted siRNA delivery across biological barriers. Adv. Drug Deliv Rev. 2013 March; 65(3):391-7. doi: 10.1016/j.addr.2012.08.008).

In certain embodiments, one or more receptor-mediated permeabilizing compounds can be used to increase the permeability of the BBB to allow delivery of an siRNA conjugate of the invention. These drugs increase the permeability of the BBB temporarily by increasing the osmotic pressure in the blood which loosens the tight junctions between the endothelial cells ((El-Andaloussi (2012)). By loosening the tight junctions normal intravenous injection of an siRNA conjugate can be performed.

In certain embodiments, nanoparticle-based delivery systems are used to deliver an siRNA conjugate across the BBB. As used herein, "nanoparticles" refer to polymeric nanoparticles that are typically solid, biodegradable, colloidal systems that have been widely investigated as drug or gene carriers (S. P. Egusquiaguirre, M. Igartua, R. M. Hernandez, and J. L. Pedraz, "Nanoparticle delivery systems for cancer therapy: advances in clinical and preclinical research," Clinical and Translational Oncology, vol. 14, no. 2, pp. 83-93, 2012). Polymeric nanoparticles are classified into two major categories, natural polymers and synthetic polymers. Natural polymers for siRNA delivery include, but are not limited to, cyclodextrin, chitosan, and atelocollagen (Y. Wang, Z. Li, Y. Han, L. H. Liang, and A. Ji, "Nanoparticle-based delivery system for application of siRNA in vivo," Current Drug Metabolism, vol. 11, no. 2, pp. 182-196, 2010). Synthetic polymers include, but are not limited to, polyethyleneimine (PEI), poly(dl-lactide-co-glycolide) (PLGA), and dendrimers, which have been intensively investigated (X. Yuan, S. Naguib, and Z. Wu, "Recent advances of siRNA delivery by nanoparticles," Expert Opinion on Drug Delivery, vol. 8, no. 4, pp. 521-536, 2011). For a review of nanoparticles and other suitable delivery systems, See Jong-Min Lee, Tae-Jong Yoon, and Young-Seok Cho, "Recent Developments in Nanoparticle-Based siRNA Delivery for Cancer Therapy," BioMed Research International, vol. 2013, Article ID 782041, 10 pages, 2013. doi: 10.1155/2013/782041 (incorporated by reference in its entirety.)

An siRNA conjugate can be administered ocularly, such as to treat retinal disorder, e.g., a retinopathy. For example, the pharmaceutical compositions can be applied to the surface of the eye or nearby tissue, e.g., the inside of the eyelid. They can be applied topically, e.g., by spraying, in drops, as an eyewash, or an ointment. Ointments or droppable liquids may be delivered by ocular delivery systems known in the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The pharmaceutical composition can also be administered to the interior of the eye, and can be introduced by a needle or other delivery device which can introduce it to a selected area or structure. The composition containing the siRNA conjugate can also be applied via an ocular patch.

In general, an siRNA conjugate of the invention can be administered by any suitable method. As used herein, topical delivery can refer to the direct application of an siRNA conjugate to any surface of the body, including the eye, a mucous membrane, surfaces of a body cavity, or to any internal surface. Formulations for topical administration may include transdermal patches, ointments, lotions, creams, gels, drops, sprays, and liquids. Conventional pharmaceutical carriers, aqueous, powder or oily bases, thickeners and the like may be necessary or desirable. Topical administration can also be used as a means to selectively deliver the siRNA conjugate to the epidermis or dermis of a subject, or to specific strata thereof, or to an underlying tissue.

Compositions for intrathecal or intraventricular (e.g., intracerebroventricular) administration may include sterile aqueous solutions which may also contain buffers, diluents and other suitable additives. Compositions for intrathecal or intraventricular administration typically do not include a transfection reagent or an additional lipophilic moiety besides, for example, the lipophilic moiety included in the siRNA conjugate.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

An siRNA conjugate of the present application can be administered to a subject by pulmonary delivery. Pulmonary delivery compositions can be delivered by inhalation of a dispersion so that the composition within the dispersion can reach the lung where it can be readily absorbed through the alveolar region directly into blood circulation. Pulmonary delivery can be effective both for systemic delivery and for localized delivery to treat diseases of the lungs. In one embodiment, an siRNA conjugate administered by pulmonary delivery has been modified such that it is capable of traversing the blood brain barrier.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are particularly suitable. One of the benefits of using an atomizer or inhaler is that the potential for contamination is minimized because the devices are self-contained. Dry powder dispersion devices, for example, deliver drugs that may be readily formulated as dry powders. An siRNA conjugate composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The types of pharmaceutical excipients that are useful as carriers include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A particularly suitable group of carbohydrates includes lactose, trehalose, raffinose maltodextrins, and mannitol. Suitable polypeptides include aspartame. Amino acids include alanine and glycine, with glycine being preferred.

pH adjusters or buffers include organic salts prepared from organic acids and bases, such as sodium citrate, sodium ascorbate, and the like; sodium citrate is preferred.

An siRNA conjugate of the invention can be administered by oral and nasal delivery. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily. In one embodiment, an siRNA conjugate administered by oral or nasal delivery has been modified to be capable of traversing the blood-brain barrier. It is to be understood that the methods described in this disclosure are not limited to particular methods and experimental conditions disclosed herein; as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by MR Green and J. Sambrook and Harlow et al., Antibodies: A Laboratory Manual, Chapter 14, Cold Spring Harbor Laboratory, Cold Spring Harbor (2013, 2nd edition).

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Materials and Methods

Oligonucleotide Synthesis, Deprotection, and Purification

Oligonucleotides were synthesized following standard protocols on an Expedite ABI DNA/RNA synthesizer or a MerMade 12 (BioAutomation, Irving, Tex., USA). Sense strands were synthesized at 1-µmole scales on synthesized fatty acid-functionalized CPG supports (Synthetic Schemes 1, 2 and 3). Antisense strands were synthesized at 10-µmole scales on CPG functionalized with Unylinker® (Chem-Genes, Wilmington, Mass.). 2'-O-methylphosphoramidites (ChemGenes, Wilmington, Mass.), 2'-fluoro phosphoramidites (BioAutomation, Irving, Tex.), Cy3-labeled phosphoramidites (Gene Pharma, Shanghai, China), and custom synthesized (E)-vinylphosphonate phosphoramidites [26] were used for preparing oligonucleotides. Oligonucleotides were removed from CPG and deprotected using 40% aqueous methylamine, and purified by HPLC as described previously [15, 26]. Purified oligonucleotides were desalted by size-exclusion chromatography, and purity and identity were determined by Liquid Chromatography-Mass Spectrometry (LC-MS) on an Agilent 6530 accurate-mass Q-TOF LC/MS (Agilent technologies, Santa Clara, Calif.).

Physicochemical Characterization of Conjugated Oligonucleotides

The relative hydrophobicities of conjugated siRNAs were determined by the retention time of each compound on an Agilent Prostar System equipped with a Water HxSil C18 column (75×4.6) in a gradient of 100% buffer A (0.1 M trimethylamine acetate in water) to 100% buffer B (0.1 M trimethylamine acetate in acetonitrile) at a flow rate of 1 ml/min for 16 min at 60° C.

Hydrodynamic diameters of siRNA were determined by dynamic light scattering (DLS) using a Zetasizer ZEN3600 (Malvern Instruments, UK). siRNAs solutions (10 nmol in 1 mL PBS) were analyzed at 25° C. in triplicate. All the scattered photons were collected at a 173°-scattering angle. The scattering intensity data was processed using instrumental software to obtain the hydrodynamic diameter and the size distribution of each sample.

Injection of Conjugated siRNAs into Mice

Animal experiments were performed in accordance with animal care ethics approval and guidelines of University of Massachusetts Medical School Institutional Animal Care and Use Committee (IACUC, protocol number A-2411). Female FB/NJ mice (The Jackson Laboratory) 7- to 8-weeks old were injected subcutaneously with phosphate buffered saline (PBS controls) or with 20 mg/kg conjugated siRNA (or unconjugated control) suspended in PBS (160 µL). For pharmacokinetic studies, 6 mice per group were injected (n=18). For distribution studies, 3 mice per conjugate were studied (n=9+1 for PBS controls). For the efficacy studies, 6 mice per group were injected (n=30, including non-targeting controls and PBS controls).

Pharmacokinetic Studies

After injection, serial blood sampling was carried out using a previously described protocol [27]. Briefly, microsamples of blood were collected from the lateral saphenous vein at different time points. Sterile needles were used to puncture the vein, slight pressure was applied above the knee joint, and blood droplets were collected using Microvette CB300 K2R tubes (Sarstedt). Blood samples were stored at −80° C. until analysis.

Peptide Nucleic Acid (PNA) Hybridization Assay

Blood and tissue concentrations of antisense strands were determined using a PNA hybridization assay [27, 28]. Blood samples (10 µL) were diluted in tissue lysis solution (MasterPure, EpiCentre) to a total of 200 µL containing 1 µL proteinase K (20 mg/mL) (Invitrogen). Tissues (15 mg) were placed in QIAGEN Collection Microtubes holding 3-mm tungsten beads and lysed in 300 µl tissue lysis solution containing 3 µl proteinase K using a QIAGEN TissueLyser II. For all samples, sodium dodecyl sulphate (SDS) was precipitated from lysates by adding 20-30 µL, 3 M potassium chloride and centrifuging at 5000×g for 15 minutes. Supernatants were then diluted in 150 µL of hybridization buffer (50 mM Tris 10% acetonitrile pH 8.8) containing 5 pmol of a Cy3-labeled PNA probe complementary to the antisense strand (PNABio, Thousand Oaks, Calif., USA). Annealing was carried out by heating the samples at 90° C. for 15 min and 50° C. for 15 min. Samples were analyzed by HPLC (Agilent, Santa Clara, Calif.) over a DNAPac PA100 anion-exchange column (Thermo Fisher Scientific). Cy3 fluorescence was monitored and peaks integrated. Final concentrations were ascertained using calibration curves generated by spiking known quantities of conjugated siRNA into blood or tissue lysates from an untreated animal.

Fluorescence Microscopy

At 48 hours post-injection, mice were euthanized and perfused with PBS. Tissues were collected and immersed in 10% formalin solution overnight at 4° C. Tissues were embedded in paraffin and sliced into 4-µm sections that were mounted on glass slides. Tissue sections on glass slides were deparaffinized by incubating twice in xylene for 8 min. Sections were rehydrated in an ethanol series from 100% to 95% to 80%, for 4 min each. Slides were then washed twice with PBS, 2 min each, incubated with DAPI (250 ng/mL, Molecular Probes) in PBS for 1 minute, and washed again in PBS for 2 minutes. Slides were mounted with PermaFluor mounting medium (Molecular Probes) coverslips, and dried overnight at 4° C. Sections were imaged at 5× and 40× using a Leica DM5500B microscope fitted with a DFC365 FX fluorescence camera.

mRNA Silencing Experiments

At 1-week post-injection, mice were euthanized. Tissues were collected and stored in RNAlater (Sigma) at 4° C. overnight. mRNA was quantified using the QuantiGene 2.0 Assay (Affymetrix). Briefly, 1.5-mm punches (3 punches per tissue) were placed in QIAGEN Collection Microtubes holding 3-mm tungsten beads and lysed in 300 µl Homogenizing Buffer (Affymetrix) containing 0.2 mg/ml proteinase K (Invitrogen) using a QIAGEN TissueLyser II. Samples were then centrifuged at 1,000×g for 10 min and incubated for 1 h at 55° to 60° C. Lysates and diluted probe sets (mouse Htt, or mouse Hprt) were added to the bDNA capture plate and signal was amplified and detected as described by Coles et al. [29]. Luminescence was detected on a Tecan M1000 (Tecan, Morrisville, N.C., USA).

Statistical Analysis

Data were analyzed using GraphPad Prism 7.01 software (GraphPad Software, Inc., San Diego, Calif.). For each independent efficacy experiment in mice, the level of silencing was normalized to the mean of the control (PBS) group. Data were analyzed using non-parametric one-way ANOVA with Dunnett's test for multiple comparisons, with significance calculated relative to PBS controls.

Synthetic Scheme 1

Figure 8:
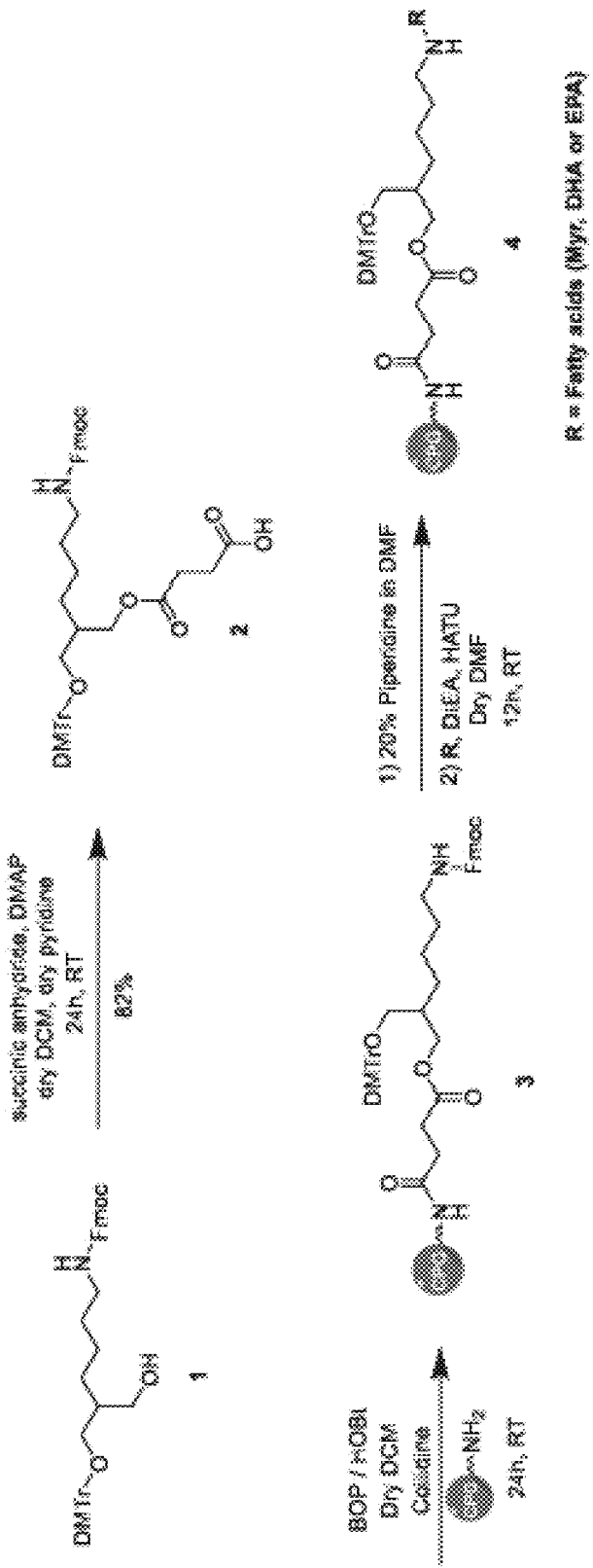
FIG. 8 is a synthetic scheme for the preparation of solid supports functionalized by one fatty acid (R=Myristic acid (Myr), Docohexaenoic acid (DHA) or Eicopentaenoic acid (EPA)).

Depicted in FIG. 8 is a synthetic scheme for the preparation of solid supports functionalized by one fatty acid (R=Myristic acid (Myr), Docohexaenoic acid (DHA) or Eicopentaenoic acid (EPA)).

C7 linker (90% purity) 1 (1.0 equiv.), 4-dimethylaminopyridine (DMAP) (cat.) and succinic anhydride (1.4 equiv.) were dissolved in dry dichloromethane (DCM) and dry pyridine. The mixture was stirred 24 h at room temperature, then washed with 10% citric acid. The organic layer was washed with water and brine, and dried over magnesium sulfate. The solvent was evaporated under pressure. Column chromatography on silica gel was performed using a gradient of methanol in a mixture of DCM:pyridine (99:1) from 0 to 10% to obtain Compound 2 (82%).

Compound 2 (2.2 equiv.), (Benzotriazol-1-yloxy) tris (dimethylamino) phosphonium hexafluorophosphate (BOP) (3.0 equiv.) and 1-Hydroxybenzotriazole (HOBt) (3.0 equiv.) were dissolved in dry DCM. The mixture was stirred 5 minutes and 2,4,6-collidine (6.0 equiv.) was added. The amino-controlled pore glass (CPG) (1.0 equiv.) was added after treatment with 3% TFA in DCM at room temperature for 4 h, and then filtrated and washed with TEA:diisopropylethylamine (9:1), then with DCM and ether. The mixture was stirred mechanically for 24 h at room temperature. The CPG was washed with DCM, acetonitrile (ACN), and ether then dried under pressure. The CPG was then capped with 16% N-methylimidazole in tetrahydrofuran (THF) (CAP A) and acetic anhydride:pyridine:THF (1:2:2, v/v/v) (CAP B)

(1:1, v/v) for 1 h, washed with DCM, ACN and ether, and dried under vacuum. The CPG 3 is obtained with a loading of 75 µmol/g.

The CPG 3 (1.0 equiv.) was treated with a solution of 20% piperidine in dry dimethylformamide (DMF) two times for 15 minutes each, washed with DCM, ACN and ether, and dried under pressure.

The selected fatty acid R (6.0 equiv.) was dissolved in dry DMF. 1-[Bis(dimethylamino)methylene]-1H-1,2,3-triazolo[4,5-b]pyridinium 3-oxid hexafluorophosphate (HATU) (6.0 equiv.) and diisopropylethylamine (DIEA) (8.0 equiv.) were added and the solution was added to the deprotected CPG. The mixture was stirred mechanically overnight at room temperature. The CPG was washed with DCM, ACN and ether, then dried under pressure. The CPG was then capped with 16% N-methylimidazole in THF (CAP A) and acetic anhydride:pyridine:THF (1:2:2, v/v/v) (CAP B) (1:1, v/v) for 1 h, washed with DCM, ACN and ether, and dried under vacuum. The lipid functionalized solid supports CPG 4 were obtained with a loading of 55 µmol/g.

Synthetic Scheme 2

Figure 9:
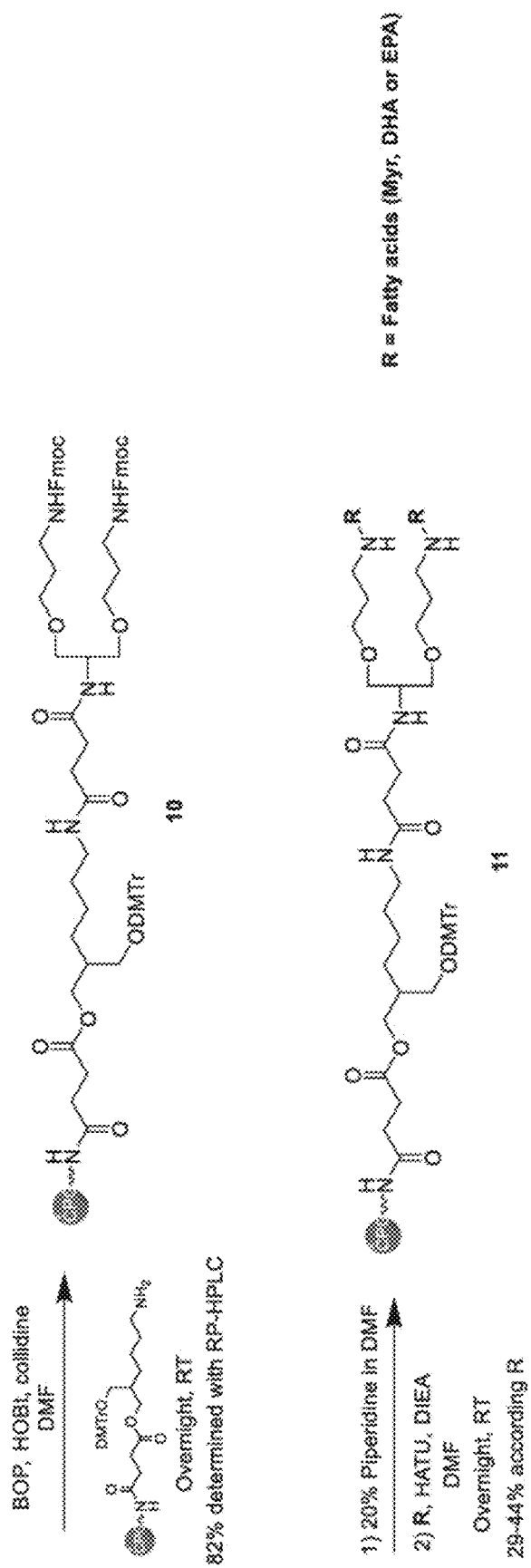
FIG. 9 is a synthetic scheme for the preparation of solid supports functionalized by two fatty acids (R=Myristic acid (Myr), Docohexaenoic acid (DHA) or Eicopentaenoic acid (EPA)).

Depicted in FIG. 9 is a synthetic scheme for the preparation of solid supports functionalized by two fatty acids (R=Myristic acid (Myr), Docohexaenoic acid (DHA) or Eicopentaenoic acid (EPA)).

2-amino-1,3-propanediol (1.0 equiv.) was dissolved in dioxane and 40% aqueous potassium hydroxide (0.1 equiv.) was added. The mixture was stirred for 10 min, then cooled at 0° C. before adding acrylonitrile (2.2 equiv.) slowly. The mixture was warmed to room temperature and stirred overnight. The solvent was evaporated and column chromatography on silica gel was performed using a gradient of methanol in DCM from 0 to 10% to obtain Compound 5 (19%).

Compound 5 (1 equiv.) was dissolved in dioxane and sodium bicarbonate (2 equiv.) was added. The mixture was cooled at 0° C. and Boc anhydride (1.5 equiv.) was added as a solution in dioxane. The mixture was stirred for 1 h at 0° C., then overnight at room temperature. Water was added and the aqueous phase was extracted with ethyl acetate (EtOAc). The organic layer was washed with saturated sodium bicarbonate. The aqueous phase was acidified to pH 1 with 10% HCl then extracted with EtOAc. The organic phase was dried and concentrated. Column chromatography on silica gel was performed using a gradient of methanol in DCM from 0 to 2% to obtain Compound 6 (77%).

A solution of Compound 6 (1 equiv.) in dry ether was added to a cooled suspension of lithium aluminum hydride (LiAlH$_4$) (2.5 equiv.) in ether for 30 min. The mixture was stirred for 1 h at 0° C., and quenched by 25% aqueous sodium hydroxide. The solution was filtrated on celite and the filtrate was evaporated. The crude was dissolved in water, and sodium bicarbonate (4 equiv.) was added. The mixture was cooled at 0° C. and Fmoc chloride (3 equiv.) was added slowly as a solution in dioxane. The mixture was stirred for 1 h at 0° C., then for 4 h at room temperature. Water was added and the aqueous phase was extracted with EtOAc. The organic layer was washed with saturated sodium bicarbonate. The aqueous phase was acidified until pH 1 with 10% HCl and then extracted with EtOAc. The organic phase was dried and the solvent was evaporated. A column chromatography on silica gel was performed using a gradient of methanol in DCM from 0 to 2% to obtain Compound 7 (49%).

Compound 7 (1 equiv.) was dissolved in a mixture of DCM:TFA (1:1, v/v) and triisopropylsilaneb (3.7 equiv.) was added. The mixture was stirred for 2 h at room temperature, and co-evaporated with DCM. DCM and sodium bicarbonate were added, and the aqueous phase was extracted with DCM. The organic phase was washed with water and brine, dried, and the solvent was evaporated. A column chromatography on silica gel was performed using a gradient of methanol in DCM from 0 to 10% to obtain Compound 8 (77%).

Compound 8 was dissolved in DCM. DMAP (0.5 equiv.), pyridine, and succinic anhydride (1.5 equiv.) were added. The mixture was stirred overnight at room temperature. Water was added to the mixture and the aqueous phase was extracted with DCM. The organic phase was washed with water and brine, dried, and the solvent was evaporated. Column chromatography on silica gel was performed using a gradient of methanol in DCM from 0 to 10% to obtain Compound 9 (72%).

The CPG 3 (1 equiv.) was deprotected with 20% piperidine in dry DMF and a mixture of Compound 9 (4 equiv.), BOP (4 equiv.), HOBt (4.0 equiv.) and 2,4,6-collidine (12.5 equiv.) in dry DMF was added to the CPG. The mixture was stirred 24 h under mechanical stirring. The CPG was washed with DCM, ACN and ether, and dried under pressure. The CPG was then capped with CAP A and CAP B (1:1, v/v) for 15 min and was washed with DCM, ACN, and ether, and dried under vacuum. CPG 10 is obtained with a loading of 55 µmol/g.

The CPG 10 (1.0 equiv.) was deprotected with 20% piperidine in dry DMF and a mixture of myristic acid or docohexaenoic acid or eicopentaenoic acid (10 equiv.), HATU (10 equiv.) and DIEA (8 equiv.) in dry DMF was added to the CPG. The mixture was stirred mechanically for 24 h. The CPG was washed with DCM, ACN, and ether, and dried under pressure. The CPG was then capped with CAP A and CAP B (1:1, v/v) for 15 min and was washed with DCM, ACN, and ether, and dried under vacuum. CPG 11 is obtained with a loading of 55 µmol/g.

Synthetic Scheme 3

Figure 10:
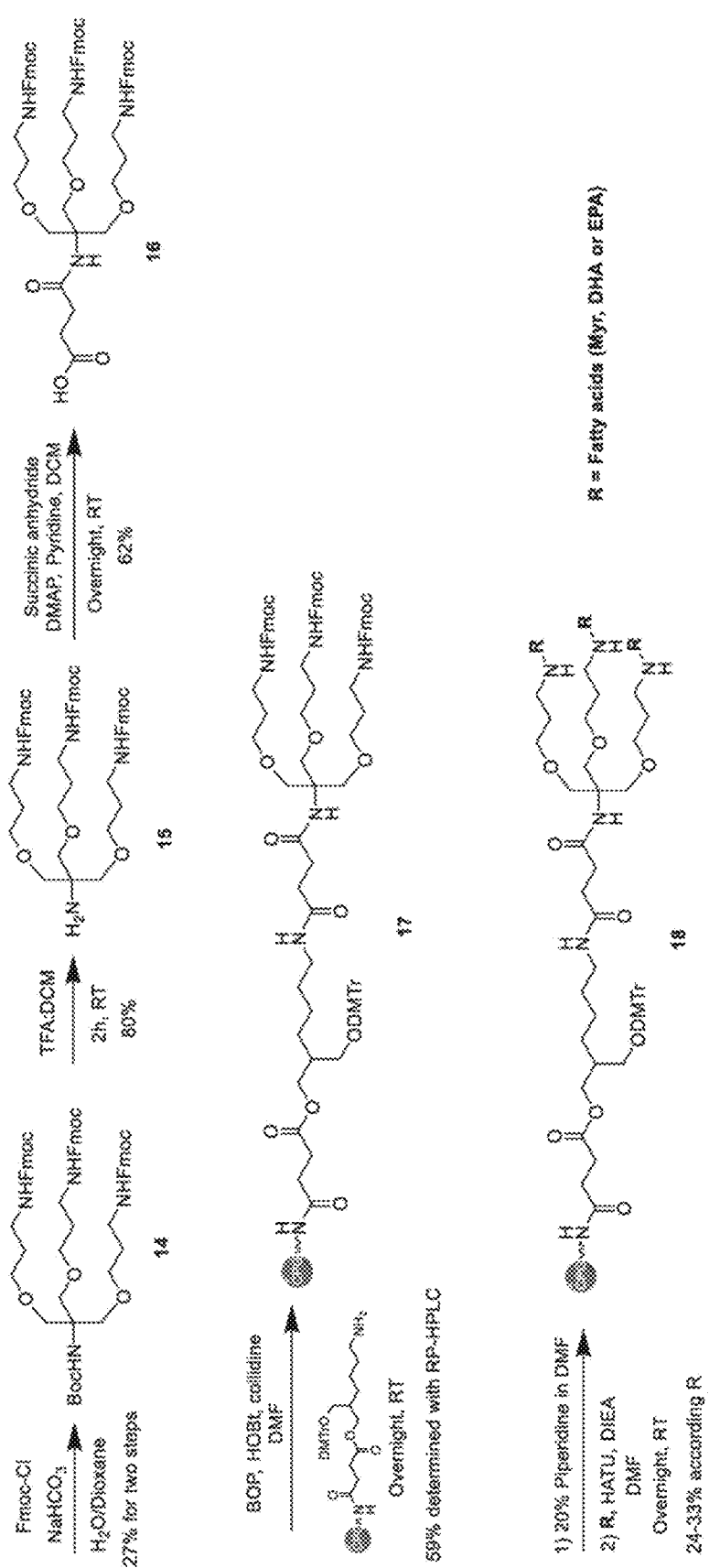
FIG. 10 is a synthetic scheme for the preparation of solid supports functionalized by three fatty acids (R=Myristic acid (Myr), Docohexaenoic acid (DHA) or Eicopentaenoic acid (EPA)).

Depicted in FIG. 10 is a synthetic scheme for the preparation of solid supports functionalized by three fatty acids (R=Myristic acid (Myr), Docohexaenoic acid (DHA) or Eicopentaenoic acid (EPA)).

Tris (1.0 equiv.) was dissolved in dioxane and 40% aqueous potassium hydroxide (0.1 equiv.) was added. The mixture was stirred for 10 min, then cooled at 0° C. before adding acrylonitrile (3.6 equiv.) slowly. The mixture was warmed to room temperature and stirred overnight. The solvent was evaporated and a column chromatography on silica gel was performed using a gradient of methanol in DCM from 0 to 10% to obtain Compound 12 (49%).

Compound 12 (1 equiv.) was dissolved in dioxane and sodium bicarbonate (2 equiv.) was added. The mixture was cooled at 0° C. and Boc anhydride (1.5 equiv.) was added as a solution in dioxane. The mixture was stirred for 1 h at 0° C., then overnight at room temperature. Water was added and the aqueous phase was extracted with ethyl acetate (EtOAc). The organic layer was washed with saturated sodium bicarbonate. The aqueous phase was acidified to pH 1 with 10% HCl then extracted with EtOAc. The organic phase was dried and concentrated. Column chromatography on silica gel was performed using a gradient of methanol in DCM from 0 to 10% to obtain Compound 13 (90%).

Compound 13 (1 equiv.) was dissolved in dry THF and borane-tetrahydrofuran (BH$_3$-THF) (1M in THF) (6 equiv.) was added dropwise. The mixture was heated at 55° C. for 5 h. 2 HCl was added to reach pH 1-2, and the mixture was neutralized with 1M sodium hydroxide. The solvent was evaporated under pressure. The crude was dissolved in water and sodium bicarbonate (6 equiv.) was added. The mixture was cooled at 0° C. and Fmoc chloride (4.5 equiv.) was added slowly as a solution in dioxane. The mixture was stirred for 1 h at 0° C., then overnight at room temperature. Water was added and the aqueous phase was extracted with EtOAc. The organic layer was washed with saturated sodium bicarbonate. The aqueous phase was acidified until pH 1 with 10% HCl and then extracted with EtOAc. The organic phase was dried and the solvent was evaporated. Column chromatography on silica gel was performed using a gradient of methanol in DCM from 0 to 10% to obtain Compound 14 (27%).

Compound 14 (1 equiv.) was dissolved in a mixture of DCM:TFA (1:1, v/v), and triisopropylsilane (3.7 equiv.) was added. The mixture was stirred for 2 h at room temperature, and co-evaporated with DCM. DCM and sodium bicarbonate were added. The aqueous phase was extracted with DCM. The organic phase was washed with water and brine, dried, and the solvent was evaporated. A column chromatography on silica gel was performed using a gradient of methanol in DCM from 0 to 8% to obtain Compound 15 (80%).

Compound 15 was dissolved in DCM. DMAP (0.5 equiv.), pyridine, and succinic anhydride (1.5 equiv.) were added. The mixture was stirred overnight at room temperature. Water was added to the mixture and the aqueous phase was extracted with DCM. The organic phase was washed with water and brine, dried, and the solvent was evaporated. Column chromatography on silica gel was performed using a gradient of methanol in DCM from 0 to 10% to obtain Compound 16 (62%).

The CPG 3 (1 equiv.) was deprotected with 20% piperidine in dry DMF and a mixture of Compound 16 (4 equiv.), BOP (4 equiv.), HOBt (4.0 equiv.) and 2,4,6-collidine (12.5 equiv.) in dry DMF was added to the CPG. The mixture was stirred mechanically for 24 h. The CPG was washed with DCM, ACN, and ether, and dried under pressure. The CPG was then capped with CAP A and CAP B (1:1, v/v) for 15 min and was washed with DCM, ACN, and ether, and dried under vacuum. CPG 17 is obtained with a loading of 55 µmol/g.

The CPG 17 (1.0 equiv.) was deprotected with 20% piperidine in dry DMF and a mixture of myristic acid or docohexaenoic acid or eicopentaenoic acid (15 equiv.), HATU (15 equiv.) and DIEA (8 equiv.) in dry DMF was added to the CPG. The mixture was stirred mechanically for 24 h. The CPG was washed with DCM, ACN, and ether, and dried under pressure. The CPG was then capped with CAP A and CAP B (1:1, v/v) for 15 min and was washed with DCM, ACN, and ether, and dried under vacuum. CPG 18 is obtained with a loading of 55 µmol/g.

Results
Synthesis of Branched Fatty Acids Conjugated to Fully Chemically Stabilized siRNAs To define the impact of the chemical structure and of the number of fatty acid chains conjugated to the siRNA on siRNA pharmacokinetics, distribution, and efficacy in vivo, we synthesized a library of siRNAs conjugated to one, two, or three fatty acids with different carbon chain lengths and degrees of unsaturation: myristic acid (Myr, C14:0), docosahexaenoic acid (DHA, C22:6), and eicosapentaenoic acid (EPA, C20:5) (FIG. 1).

A fully stabilized modified asymmetric siRNA was used as a scaffold (FIG. 1A) [30]. Asymmetric siRNAs consist of a short duplex region (15 base-pairs) and a single-stranded fully phosphorothioate-modified tail that assists membrane association [31, 32]. All riboses are modified using an alternating 2'-O-methyl and 2'-fluoro modification pattern, which confers stability and minimizes innate immune activation [5, 33, 34]. The antisense strand is modified with a 5'-(E)-vinylphosphonate (E-VP) group that mimics the 5'-phosphate of the antisense strand to promote recognition by RISC (RNA-induced silencing complex) [35, 36] and provides stability against phosphatases and exonucleases [15, 37, 38]. The sense strand is labeled with Cy3 at the 5'-end, allowing for visualization of siRNA spatial distribution in tissues.

Fatty acids were covalently attached to the 3' end of the siRNA sense strand (FIG. 1B), which tolerates a range of covalent modifications [7, 39, 40]. All fatty acid conjugated siRNAs were synthesized using a functionalized solid support (Synthetic Schemes 1, 2 and 3, below) [16]. For the incorporation of either two or three fatty acids, synthetic dividers (Synthetic Schemes 2 and 3, compounds 9 and 16, respectively) were introduced on the solid support to minimize steric hindrance, followed by fatty acid conjugation (Synthetic Schemes 2 and 3, solid supports 11 and 18). Oligonucleotides were purified by High Performance Liquid Chromatography (HPLC) and characterized by mass spectrometry.

The Valency of Fatty Acid Chains in the Conjugate Affects siRNA Hydrophobicity and Aggregation To evaluate the impact of conjugate chemical structure and valency on siRNA physicochemical properties, we measured the overall hydrophobicity and aggregation of each compound. The retention time in reversed-phase HPLC was used to determine overall hydrophobicity (increases with retention time) (FIG. 2A) [41]. Monosubstituted fatty acid-conjugated siRNAs had the lowest retention time (8.8 to 9.5 min), followed by divalent (12 to 13 min), and trivalent (15 to 16 min) fatty acids, respectively. The nature of the fatty acid carbon chain (Myr vs. DHA vs. EPA) had a relatively low impact on retention time. Our findings suggest that increasing the valency of the fatty acid conjugates increases overall compound hydrophobicity.

Figure 2B:
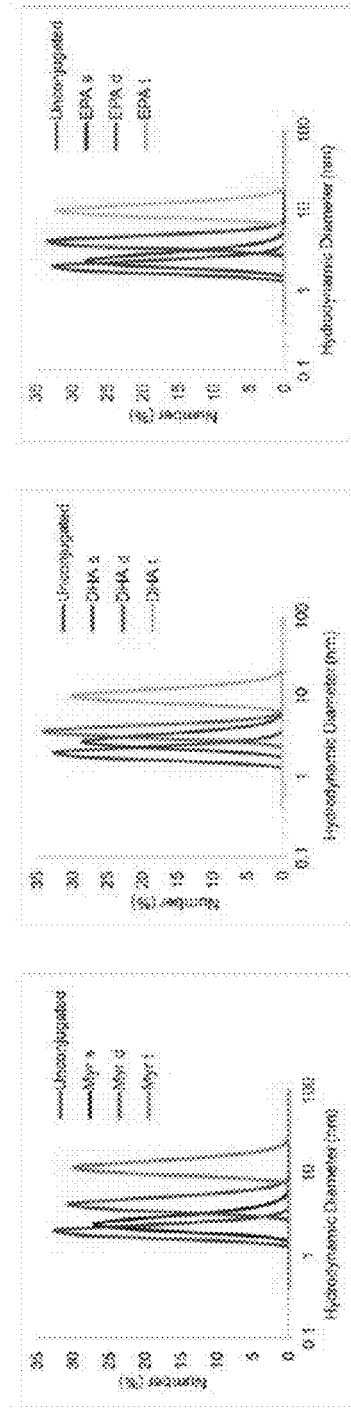

Lipid-conjugated siRNAs can self-assemble in aqueous media [42]. To determine the impact of the chemical structure and of the number of fatty acid chains on aggregate size, hydrodynamic diameters of fatty acid-conjugated siRNAs were measured by Dynamic Light Scattering (DLS) (FIG. 2B). The monovalent fatty acid-conjugated siRNAs did not aggregate, with a mean diameter of 2.5 nm, similar to unconjugated siRNA. By contrast divalent and trivalent fatty acid-conjugated siRNAs did self-assemble into small aggregates and micelles. The average particle size was much larger for trivalent compared to divalent compounds (11 versus 4 nm diameter, respectively). The nature of the fatty acid carbon chain (Myr vs DHA vs EPA) did not significantly affect the size of the aggregate formed. Our findings suggest that valency of the fatty acid conjugate impacts siRNA physicochemical properties.

Impact of Fatty Acid Conjugate Valency on siRNA Tissue Distribution Profile.

Figures 3A, 3B:
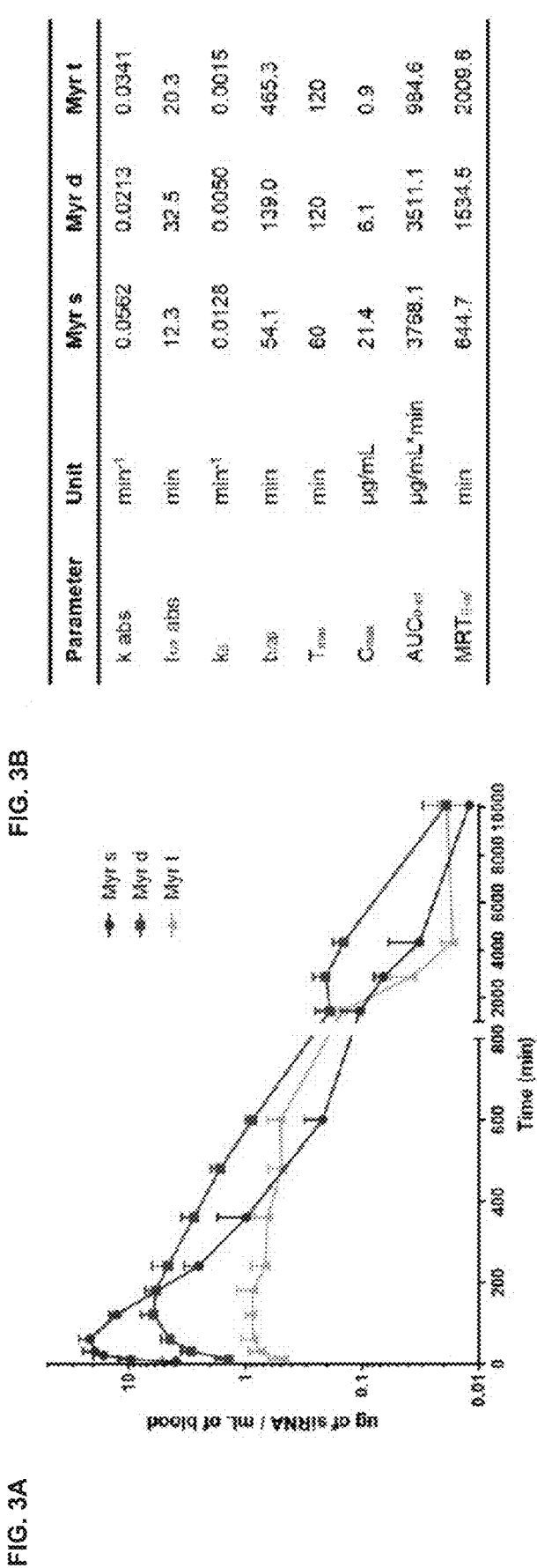
FIGS. 3A-3B show that Myr-s, Myr-d and Myr-t conjugated siRNAs exhibit distinct pharmacokinetic profiles.

Understanding clearance kinetics of engineered siRNAs is essential for further functional optimization [43]. Given that siRNA physicochemical properties were mainly affected by valency rather than the chemical nature of the conjugate carbon chain, we evaluated the impact of valency on clearance profile using one fatty acid—Myristic acid. The blood clearance profile for siRNAs conjugated with monovalent (Myr-s), divalent (Myr-d), and trivalent (Myr-t) myristic acid were evaluated (FIG. 3) by injecting siRNA into mice subcutaneously (n=6 per variant, 20 mg/kg dose), and collecting blood samples at different time points according to a previous method [27]. Pharmacokinetic profiles were determined by quantifying antisense strands in blood samples using a peptide nucleic acid (PNA) hybridization assay [28] (FIGS. 3A and 3B).

Myr-s, Myr-d, and Myr-t conjugated siRNAs showed distinct clearance profiles. Myr-s siRNAs were rapidly released into the blood from the site of injection ($t_{1/2}$ abs=12 min, $T_{max}$=60 min), whereas Myr-d exhibited slower release ($t_{1/2}$ abs=32 min, $T_{max}$=120 min). Although the areas under the curve (AUC) between Myr-s and Myr-d siRNAs were similar (3768 and 3511 μg/mL*min, respectively), the mean residence time (MRT) for Myr-d siRNAs was more than 2-fold higher than for Myr-s siRNAs (1543 and 644 min, respectively). These data suggest that Myr-d siRNAs stayed in the circulation longer than Myr-s siRNAs despite the two having comparable levels in the blood. By contrast, the majority of Myr-t siRNAs were not released from the site of injection (AUC of 984 μg/mL*min) even after one week. This is likely due to Myr-t siRNAs forming highly hydrophobic micelles (FIG. 2A). Our results suggest that altering fatty acid conjugate valency generates siRNA compounds with substantially different pharmacokinetic profiles.

Fatty Acid Conjugate Valency Fundamentally Defines siRNA Tissue Accumulation Profiles.

Figure 4A:
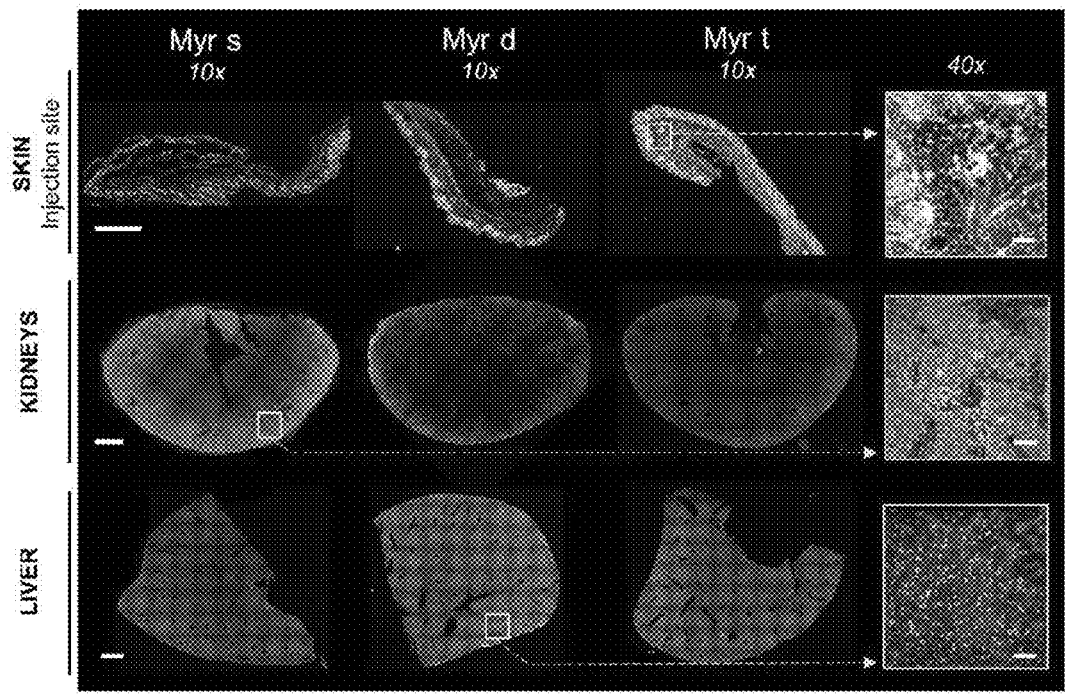
FIGS. 4A-4B demonstrate that lipid valency defines siRNA accumulation in skin (injection site), kidney, and liver.
Figure 4B:
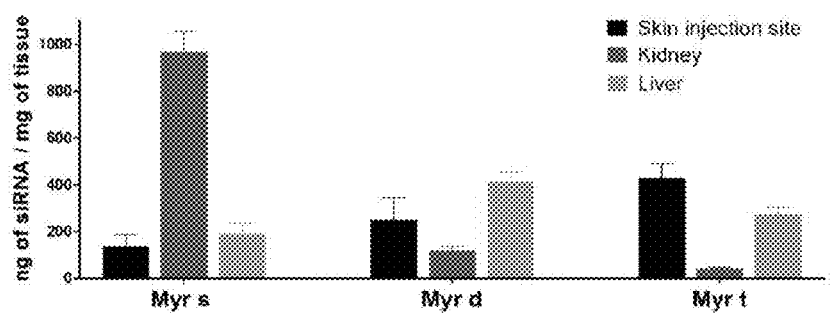
Figure 5:
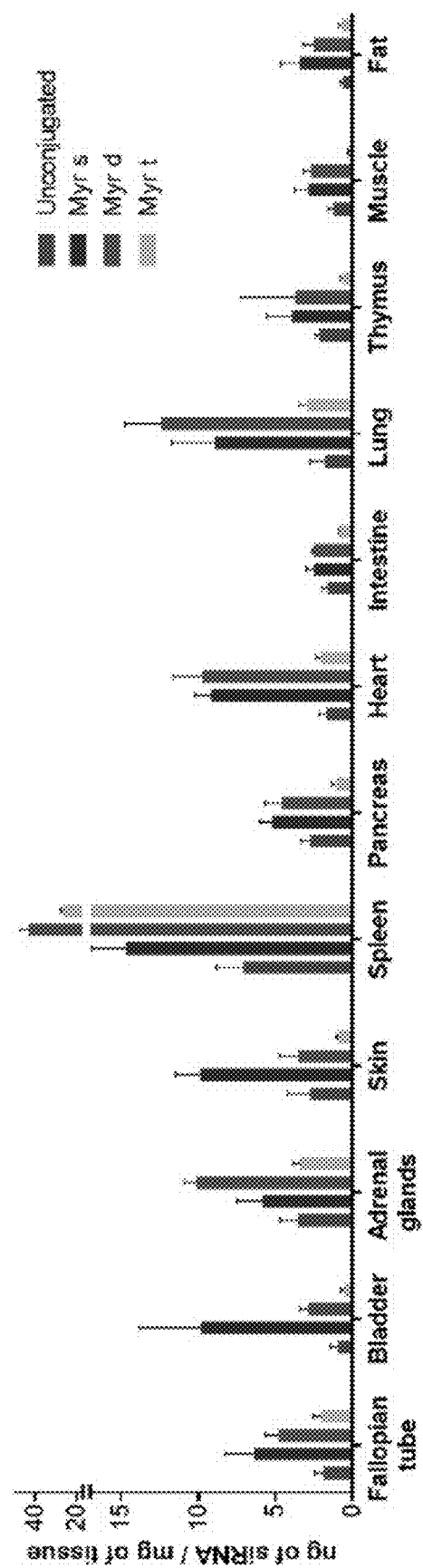
FIG. 5 is a bar graph demonstrating that siRNA accumulation is defined by the valency of lipid conjugates: mono- and di-substitution with fatty acids enhance siRNA retention into extra-hepatic tissues. The bar graph (mean±SD) shows the quantity of unconjugated, Myr-s, Myr-d, and Myr-t conjugated siRNAs in 12 tissues at 48 h after a single subcutaneous injection (20 mg/kg) in mice (n=3). siRNA quantification was determined by PNA hybridization assay.

To evaluate the impact of fatty acid conjugate valency on siRNA tissue distribution, we injected mice subcutaneously with Myr-s, -d, or -t siRNA variants (20 mg/kg, n=3 per variant). 48 hours post injection, we collected 15 tissues per mouse—liver, kidney, adrenal gland, lung, heart, thymus, spleen, pancreas, intestine, fallopian tube, bladder, fat (white fat from the belly), muscle, injection site, and skin—and evaluated spatial and quantitative siRNA tissue distribution in each sample. Spatial siRNA distribution was evaluated using fluorescence microscopy (Cy3 fluorophore attached to 5' end of sense strand). We have previously shown that the presence of Cy3 has minimal impact on overall tissue distribution in the context of lipophilic siRNAs [17]. We quantified antisense strand accumulation using a PNA hybridization assay [28], which is not dependent on the presence of Cy3. Both methodologies generated overall consistent data.

siRNA variants were mostly cleared from the blood ($AUC_{0-48h}$>85% of total AUC) at 48 hours post-injection, suggesting that tissue distribution profiles at this time point are representative of overall long-term delivery. FIG. 4 shows siRNA distribution in primary sites—liver, kidney and site of infection, where compounds accumulate to the largest extent. In general, levels of siRNA accumulation in primary sites were at least 20-fold higher than in extra-hepatic tissues (FIG. 4, FIG. 5). Fatty acid conjugate valency had a profound impact on the liver-to-kidney-to skin (site of injection) distribution ratio (FIG. 4). Representative fluorescent images (FIG. 4A) and antisense strand quantification (FIG. 4B) of liver, kidney, and skin (site of injection) show that Myr-s siRNAs preferentially accumulated in kidneys, Myr-d in liver, and Myr-t at the injection site. The difference in the liver-to-kidney distribution between Myr-s and Myr-d is consistent with our previous result that more hydrophobic compounds accumulate in liver and less hydrophobic compounds accumulate in kidney [17]. The preferential skin delivery and reduced liver accumulation of Myr-t is consistent with its limited release from the skin, and lower $C_{max}$ and AUC (FIG. 3B).

Figure 11A:
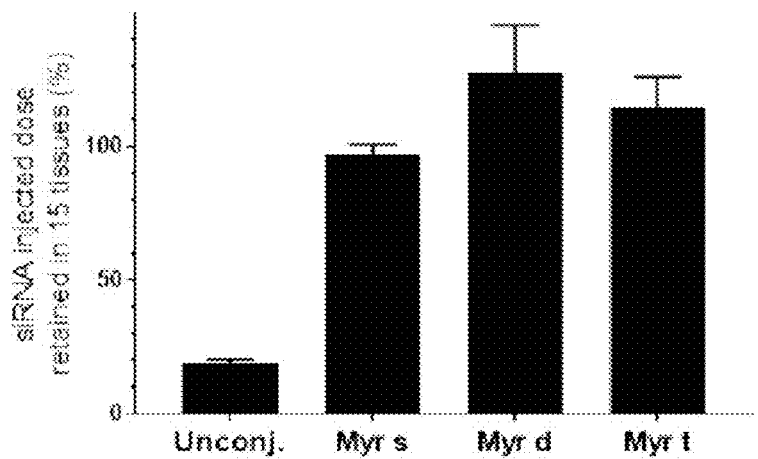
FIGS. 11A-11B illustrate overall siRNA retention and distribution of unconjugated and Myr variant conjugated siRNAs.

Measuring antisense strand accumulation in 15 tissues, which comprise most of the mouse body, allowed us to estimate the fraction of the injected siRNA dose that was retained after 48 hours (FIG. 11A, Table 1).

TABLE 1 siRNA tissue concentration and estimated tissue/organ weight values used to calculate total amount of compound accumulation in tissue, and levels of retention for (A.) Myr s-conjugated siRNA, (B.) Myr-d conjugated siRNA, and (C.) Myr-t conjugated siRNA. Total injected dose per mice = 0.5 mg of siRNA.

| Tissues | ng of siRNA/mg of tissue (average of n = 3) | Estimated organ weights (mg) | Total amount of siRNA per tissue (ng) | siRNA injected dose retained (%) |
|---|---|---|---|---|
| A. | | | | |
| Liver | 193.3 | 1000 | 193293.0 | 38.7 |
| Kidney | 966.5 | 304 | 146902.7 | 29.4 |
| Skin injection site | 138.3 | 650 | 89904.4 | 18.0 |
| Fallopian tube | 6.4 | 141 | 897.5 | 0.2 |
| Bladder | 9.8 | 12 | 117.7 | 0.0 |
| Adrenal | 5.8 | 4 | 23.4 | 0.0 |
| Skin | 9.9 | 2400 | 23750.7 | 4.6 |
| Spleen | 14.7 | 92 | 1352.4 | 0.3 |
| Pancreas | 5.2 | 134 | 697.9 | 0.1 |
| Heart | 9.1 | 94 | 859.5 | 0.2 |
| Intestin | 2.5 | 1400 | 3564.9 | 0.7 |
| Lung | 8.9 | 201 | 1791.4 | 0.4 |
| Thymus | 3.9 | 104 | 409.3 | 0.1 |
| Muscle | 2.8 | 2400 | 6805.8 | 1.4 |
| Fat | 3.4 | 4600 | 15706.5 | 3.1 |
| Total | 1380.7 | 13536 | 486077.1 | 97.2 |
| B. | | | | |
| Liver | 413.8 | 1000 | 413842.9 | 82.8 |
| Kidney | 122.4 | 304 | 18597.7 | 3.7 |
| Skin inj. site | 251.9 | 650 | 163737.8 | 32.7 |
| Fallopian tube | 4.8 | 141 | 672.3 | 0.1 |
| Bladder | 2.9 | 12 | 23.0 | 0.0 |
| Adrenal | 10.1 | 4 | 40.3 | 0.0 |
| Skin | 3.5 | 2400 | 8485.6 | 1.7 |
| Spleen | 43.4 | 92 | 3989.4 | 0.8 |
| Pancreas | 4.5 | 134 | 614.8 | 0.1 |
| Heart | 9.7 | 94 | 913.3 | 0.2 |
| Intestin | 2.5 | 1400 | 3539.3 | 0.7 |
| Lung | 12.4 | 201 | 2495.5 | 0.6 |
| Thymus | 3.7 | 104 | 384.6 | 0.1 |
| Muscle | 2.7 | 2400 | 6369.6 | 1.3 |
| Fat | 2.5 | 4600 | 11629.0 | 2.3 |
| Total | 890.8 | 13536 | 635335.1 | 127.1 |
| C. | | | | |
| Liver | 275.6 | 1000 | 275515.1 | 55.1 |
| Kidney | 44.9 | 304 | 6831.2 | 1.4 |
| Skin inj. site | 429.9 | 650 | 279423.1 | 55.9 |
| Fallopian tube | 2.0 | 141 | 285.2 | 0.1 |
| Bladder | 0.6 | 12 | 6.6 | 0.0 |
| Adrenal | 3.4 | 4 | 13.6 | 0.0 |
| Skin | 0.9 | 2400 | 2180.7 | 0.4 |
| Spleen | 26.8 | 92 | 2462.8 | 0.6 |
| Pancreas | 1.1 | 134 | 145.3 | 0.0 |
| Heart | 2.1 | 94 | 198.4 | 0.0 |
| Intestin | 0.9 | 1400 | 1217.3 | 0.2 |
| Lung | 2.9 | 201 | 589.1 | 0.1 |
| Thymus | 0.5 | 104 | 63.0 | 0.0 |
| Muscle | 0.3 | 2400 | 724.5 | 0.1 |
| Fat | 0.7 | 4600 | 3190.9 | 0.6 |
| Total | 792.6 | 13536 | 572846.8 | 114.5 |

Figure 11B:
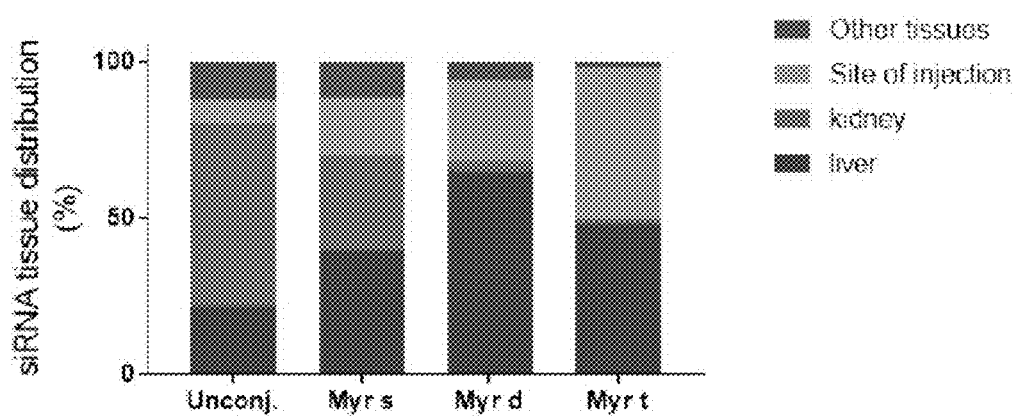

The mass of each tissue was experimentally defined, or approximated based on published mouse organ weights [44-46]. More than 85% of unconjugated siRNAs were cleared from the body, while the majority of the retained siRNA accumulated in kidneys (FIG. 11). The addition of fatty acid conjugates dramatically enhanced siRNA overall retention—approximately 100% of the injected dose for all three variants was accounted for. These findings indicate that fatty acid conjugates, regardless of valency status, reduce clearance into the urine compared to unconjugated siRNAs.

FIG. 5 shows quantification of antisense strand accumulation in twelve tissues, including bladder, spleen, heart, lung, muscle, and fat. Myr-s and Myr-d siRNAs distributed to extra-hepatic tissues significantly more than unconjugated siRNAs and Myr-t. Overall tissue distribution profiles for Myr-s and Myr-d conjugated siRNAs were similar, with a few exceptions (Table 1). Myr-s accumulated in bladder and skin (systemic, far from the site of injection) to a significantly higher degree than Myr-d. By contrast, Myr-d showed enhanced delivery to the lung. These findings indicate that modulating the valency of fatty acid conjugates can alter compound tissue distribution, and potentially enhance extra-hepatic delivery.

Fatty Acid Conjugated siRNAs Enable Functional Gene Silencing in Several Tissues.

Figure 6:
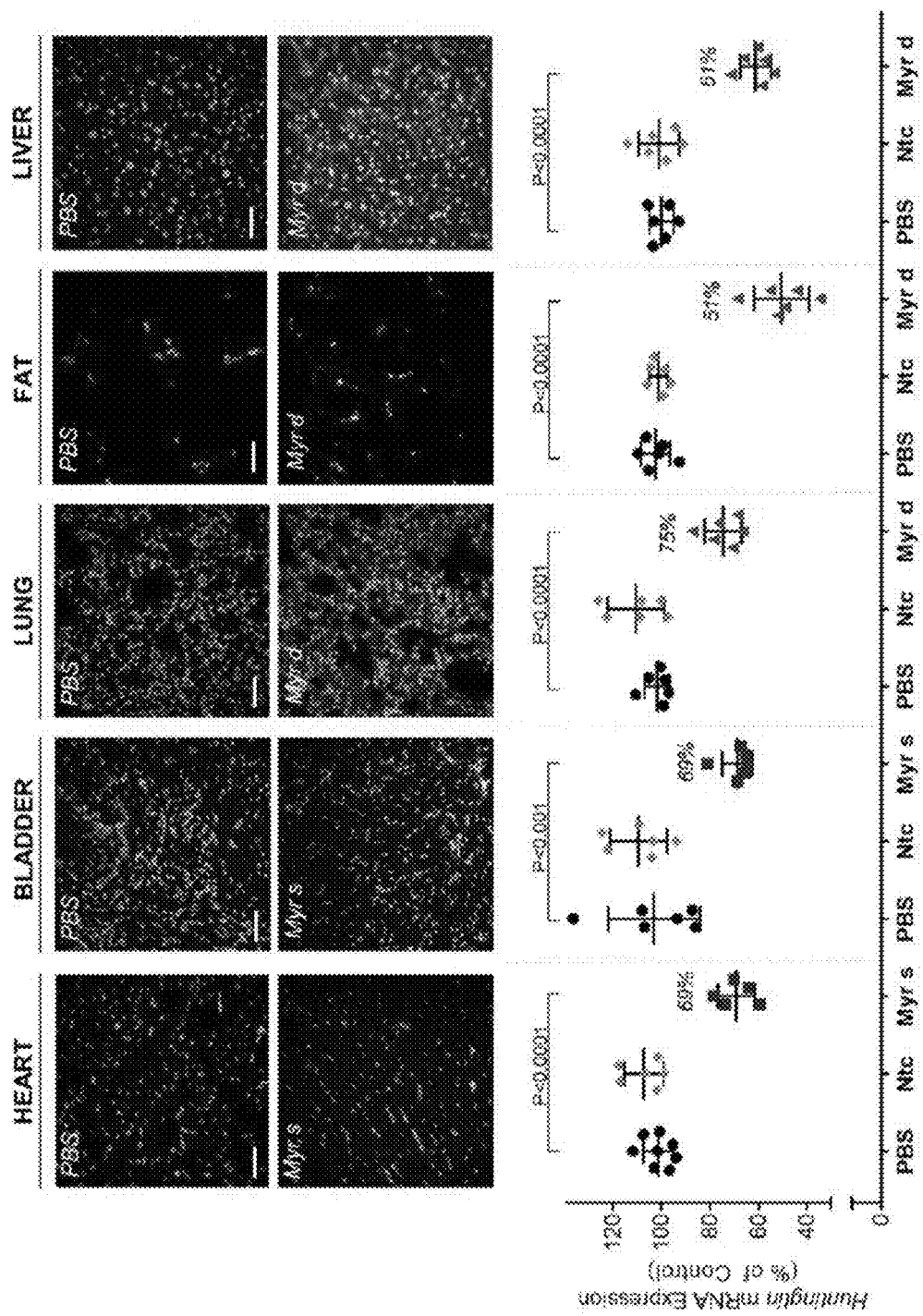
FIG. 6 shows that the amounts of conjugated siRNA in several tissues are sufficient to induce mRNA silencing. Representative fluorescence images of heart, bladder, lung, fat, and liver sections from mice (n=3 per conjugate) injected subcutaneously with 20 mg/kg Cy3-labeled Myr variant conjugated siRNAs (red) or PBS. Nuclei stained with DAPI (blue). Tissues were collected 48 h after injection. Images taken at 40× magnification and collected at the same laser intensity and acquisition time. Scale, 50 μm. For the measurement of mRNA, mice were injected subcutaneously with 20 mg/kg of conjugated siRNA (n=6 per group, Ntc=non-targeting controls). The tissues were collected after 1 week, and Huntingtin (Htt) mRNA levels were measured using QuantiGene®, normalized to a housekeeping gene, Hprt (Hypoxanthine-guanine phosphoribosyl transferase), and presented as percent of PBS control (mean±SD). Statistical analysis: One-way ANOVA with Bonferroni correction.
Figure 12:
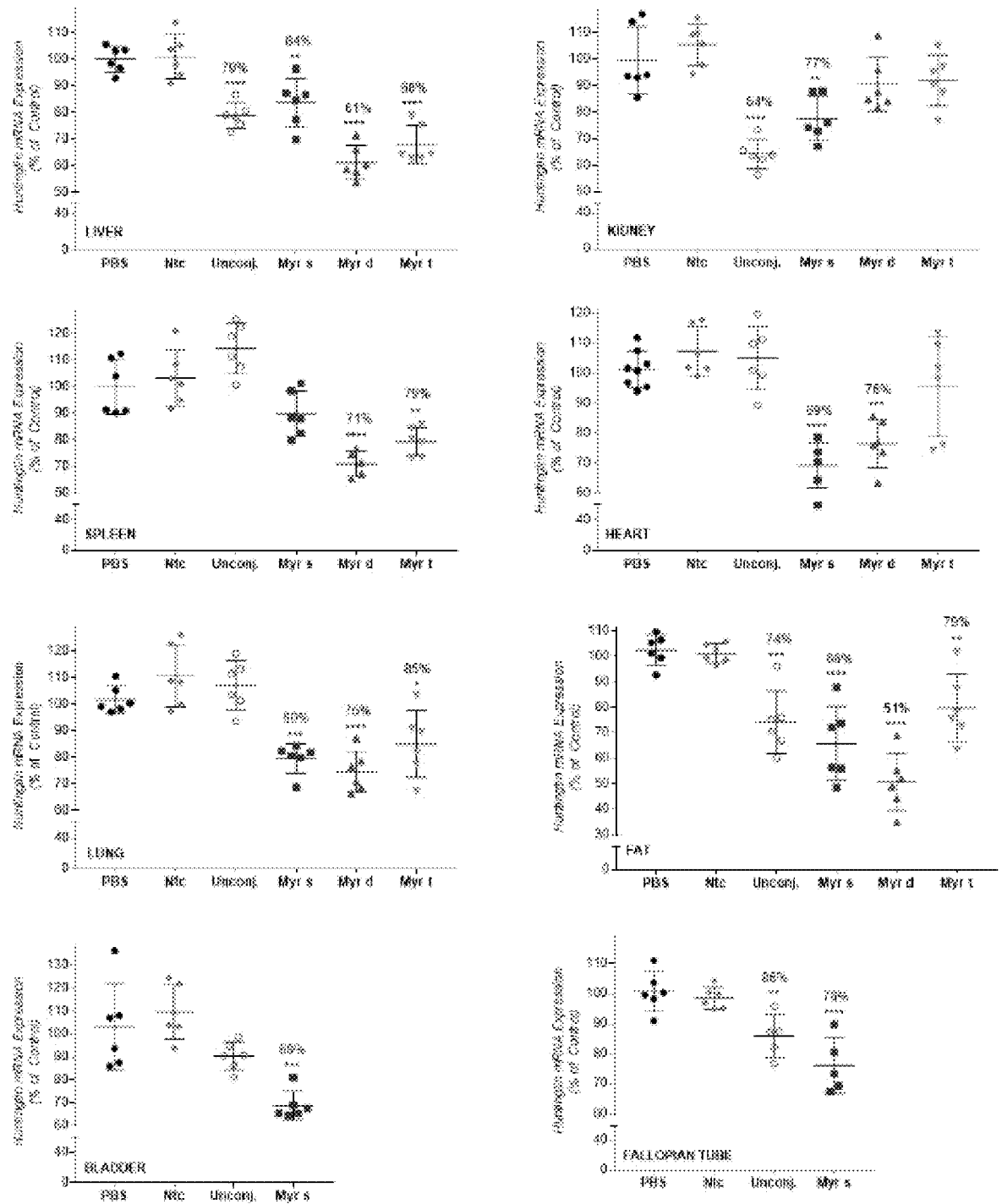
FIG. 12 illustrates how the presence of fatty acids enhances mRNA silencing into several extra-hepatic tissues. Mice were injected subcutaneously with 20 mg/kg of unconjugated or Myr variant conjugated siRNAs (n=6 per group, Ntc=non-targeting controls). The tissues were collected 1 week after injection and mRNA levels of Huntingtin were measured using QuantiGene (mean±SD). Data analysis: One-way ANOVA, Dunnett test, * P<0.1,  P<0.01, * P<0.001, **** P<0.0001.

To evaluate the effect of conjugate valency on gene silencing, mice were injected subcutaneously with Myr-siRNA variants targeting Huntingtin (Htt) mRNA or controls (n=6 per group, 20 mg/kg). We elected to target Htt mRNA because it is widely expressed in all tissues and has a validated siRNA sequence available [47]. Htt and Hprt (hypoxanthine-guanine phosphoribosyl transferase, a housekeeping gene) mRNA expression was measured one week post injection using the QuantiGene Assay. The efficacy of Htt targeting compounds with different Myr variants was evaluated in liver, kidneys, spleen, heart, lung, fat, bladder, and fallopian tube (FIG. 6, FIG. 12). PBS, unconjugated siRNAs, and a non-targeting siRNA (Ntc, compound of identical chemical configuration but not targeting Htt mRNA) were used as controls.

Ntc was indistinguishable from PBS in all tissues tested, suggesting that any observed modulation of gene expression is target-specific and not related to overall oligonucleotide chemical configuration. Unconjugated compounds induced statistically significant silencing in kidneys (FIG. 12). This finding is consistent with previously reported data, and is likely due to the phosphorothioate modifications in our siRNA scaffold driving renal epithelia retention [31, 48].

Conjugation of fatty acids had a profound impact on siRNA efficacy, and statistically improved silencing in several tissues (compared to unconjugated, PBS and Ntc compounds) (FIG. 6, FIG. 12). In general, there was a correlation between the degree of accumulation and the level of silencing within the same tissue. Myr-s conjugated siRNAs accumulated to a higher extent in bladder (~10 ng/mg, FIG. 5), resulting in productive silencing (31% silencing, FIG. 6), while Myr-d conjugated siRNA compounds show higher accumulation and more productive silencing in lung and spleen (8 ng/mg, 25% silencing; and 42 ng/mg, 29% silencing, respectively) (FIG. 5, FIG. 6, FIG. 12).

The levels of accumulation necessary for productive silencing differed significantly between tissues, likely due to differences in internalization pathways and intracellular trafficking. For example, Myr-d siRNAs accumulated to 3 ng/mg in fat (FIG. 5), translating to ~50% silencing ($P<0.0001$) (FIG. 6), whereas Myr-d kidney accumulation was >100 ng/mg (FIG. 4B) and did not support functional silencing (FIG. 12). FIG. 6 shows representative data for delivery and functional silencing in key tissues for the best-delivered siRNA per tissue—Myr-s siRNAs for heart, and bladder, and Myr-d siRNAs for lung, fat and liver. Myr-s conjugated siRNAs induced 31% silencing in both tissues, and Myr-d siRNA compounds induced 25%, 49% and 39% silencing in lung, fat, and liver respectively. All observed effects were statistically significant relative to PBS or Ntc ($P<0.0001$ or $P<0.001$, One-way ANOVA with Bonferroni correction). Our collective findings suggest that altering fatty acid conjugate valency affects tissue-specific siRNA accumulation for productive gene silencing.

siRNA Hydrophobicity does not Fully Explain Differences in siRNA Distribution and Efficacy We and others have previously demonstrated that differences in conjugate-mediated siRNA tissue distribution are partially explained by changes in serum lipoprotein binding that are driven by hydrophobicity [14, 18, 19]. To evaluate how conjugate chemical structure impacts siRNA tissue distribution profiles independent of hydrophobicity, we compared tissue accumulation and efficacy of three conjugated siRNA: Myr-d, cholesterol (Chol), and α-tocopheryl succinate (TS) siRNAs.

FIG. 7A shows reverse-phase HPLC traces for the three conjugated siRNAs. All three compounds have similar retention time (within 11.5-12.5 minutes), indicating they have similar hydrophobicities. siRNA variants were then injected subcutaneously (20 mg/kg dose) into mice (n=3 per variant) and tissue accumulation was evaluated at 48 hours post injection (PNA hybridization assay). FIG. 7B shows that accumulation in primary clearance tissues (liver/kidney/injection site) were similar between Myr-d and Chol but different for TS compounds. While Myr-d and Chol siRNAs mostly distributed to liver and site of injection, TS siRNAs accumulated equally between all three tissues. Next, we evaluated the impact of conjugate chemistry on extrahepatic/extrarenal delivery, and observed significant differences (FIG. 7C). For example, Myr-d siRNAs accumulated to higher levels in lung (~13 ng/mg), and heart (~10 ng/mg), whereas TS siRNA clearly accumulated to a higher degree in adrenal gland (FIG. 7C).

Finally, we evaluated the impact of conjugate chemical structure on gene silencing in tissues where differences in accumulation were observed (n=6-8, compared to PBS and Ntc, 1-week post-injection, QuantiGene Assay). Myr-d siRNAs show statistically significant silencing in lung and heart (25% and 24% silencing respectively, $P<0.01$), whereas Chol and TS siRNAs did not. Similarly, TS and Chol siRNAs induced silencing in adrenal gland (34% and 26% silencing, $P<0.001$ and $P<0.1$ respectively), but Myr-d siRNA compounds did not (FIG. 7D). In liver, significant silencing is observed for all three compounds, which can be explained by the significant accumulation of all three siRNAs in this tissue (FIG. 7B).

Without being bound to any particular theory, our findings suggest that although the physicochemical properties (e.g., the hydrophobicity) of a conjugate may affect siRNA clearance and distribution, the chemical nature/structure and self-association properties of conjugated-siRNA drive cellular internalization and functional silencing.

Discussion

The recent clinical success of GalNAc-conjugated siRNAs for liver-associated disorders demonstrates that the conjugation of chemically-stabilized siRNA is primordial for developing therapeutic oligonucleotides [8, 9, 11, 49]. Lipid conjugation of siRNAs supports broad tissue distribution beyond the liver [6, 17]. Advancements in lipid engineering may further refine siRNA delivery, but the relationship between conjugate structure/configuration and siRNA pharmacodynamic behavior must be more clearly defined. Herein reported are the first effects of lipid conjugate valency on siRNA delivery. We demonstrate that modulating conjugate valency alters siRNA physicochemical properties, which directly affect clearance, distribution, and silencing. This study demonstrates that rational engineering of lipid conjugates may be used to enhance extrahepatic siRNA delivery and efficacy.

Unconjugated siRNAs are quickly cleared from the bloodstream [27, 50, 51] with less than ~15% body retention [17]. Primary retention is in the kidney epithelia due to the high phosphorothioate (PS) content of our siRNA scaffold (13 PS bonds within a 35-nucleotide scaffold). This retention mechanism is similar to that of short single-stranded PS-antisense oligonucleotides [31, 48, 52]. In general, lipid conjugates significantly improve siRNA overall body retention (almost 100%) and extra-hepatic/extra-renal tissue exposure. We and others have shown that the higher overall retention and tissue distribution of lipophilic siRNAs is primarily explained by changes in hydrophobicity that drive serum lipoprotein binding [14, 18, 19]. Less hydrophobic compounds preferentially bind HDL and accumulate in kidney; more lipophilic siRNAs preferentially bind LDL and accumulate in liver.

By manipulating lipid conjugate valency, we were able to modulate hydrophobicity such that siRNA pharmacokinetic behaviors and distribution to primary clearance tissues were altered. Trivalent fatty acid-conjugated siRNAs are highly hydrophobic, resulting in ineffective release from the injection site, low siRNA blood level and systemic exposure, and limited tissue accumulation. Without being bound to any particular theory, these relatively poor pharmacokinetic properties may be due to micelle formation and non-productive entrapment in neighboring subcutaneous fat. The hydrophobicity of the trivalent conjugate appears to be well above the optimal range for siRNA distribution in vivo beyond the injection site.

Monovalent fatty acid-conjugated siRNAs were rapidly released into the bloodstream and predominantly accumulated in kidney (FIG. 3). Their overall behavior is similar to relatively less lipophilic conjugates like DHA, which preferentially bind HDL [18, 27]. Divalent fatty acid-conjugated siRNAs are released from the injection site, but stayed in the blood longer than monovalent compounds, and accumulated predominantly in liver. Thus, in this aspect, divalent lipid-conjugated siRNAs act similar to LDL-binding compounds.

Although hydrophobicity primarily explains the effect of conjugate valency on the liver-to-kidney accumulation profile, the exact chemical nature/structure of the conjugate impacted the degree of siRNA accumulation in extrahepatic/extrarenal tissues. Myr-d siRNA showed lung accumulation levels ~3 times higher than other conjugated siRNAs of similar hydrophobicities, which resulted in productive silencing. The mechanism underlying enhanced lung delivery is unknown, but may be due to the impact of lipid branching on membrane fluidity, receptor interactions, and trafficking/endosomal escape.

Consistent with previous reports on siRNA accumulation/efficacy ratios for different tissues [17, 53], we found that the level of tissue accumulation sufficient to induce mRNA silencing is tissue-dependent. Liver and kidney require relatively high (>100 ng/mg, FIG. 4B) siRNA accumulation, whereas lung, fat, and heart require relatively low siRNA accumulation (2-13 ng/mg, FIG. 5) for productive silencing. This is likely related to tissue-specific internalization mechanisms. Liver and kidneys are responsible for eliminating metabolic bi-products from the bloodstream. Thus, oligonucleotides largely accumulate in those tissues as a byproduct of filtering and are trapped non-productively. By contrast, cellular internalization in non-filtering tissues results from active endocytosis.

This study reports that the valency of fatty acid conjugates is a strong determinant of the siRNA pharmacokinetic and distribution profiles in vivo. Thus, chemically engineering lipid-conjugated siRNA is a viable strategy for improving extrahepatic delivery and efficacy of therapeutic siRNAs.

CITED REFERENCES

1. Zhou, J.; Shum, K.-T.; Burnett, J. C.; Rossi, J. J. Nanoparticle-based delivery of RNAi therapeutics: Progress and challenges. Pharmaceuticals 2013. 6, 85-107.
2. Scherman, D.; Rousseau, A.; Bigey, P.; Escriou, V. Genetic pharmacology: Progresses in siRNA delivery and therapeutic applications. Gene Ther. 2017. 24, 151-156.
3. Nair, J. K.; Willoughby, J. L. S.; Chan, A.; Charisse, K.; Alam, M. R.; Wang, Q.; Hoekstra, M.; Kandasamy, P.; Kel'in, A. V.; Milstein, S.; Taneja, N.; O'Shea, J.; Shaikh, S.; Zhang, L.; van der Sluis, R. J.; Jung, M. E.; Akinc, A.; Hutabarat, R.; Kuchimanchi, S.; Fitzgerald, K.; Zimmermann, T.; van Berkel, T. J. C.; Maier, M. A.; Rajeev, K. G.; Manoharan, M. Multivalent N-acetylgalactosamine conjugated siRNA localizes in hepatocytes and elicits robust RNAi-mediated gene silencing. JACS2014. 136, 16958-16961.
4. Zimmermann, T. S.; Karsten, V.; Chan, A.; Chiesa, J.; Boyce, M.; Bettencourt, B. B.; Hutabarat, R.; Nochur, S.; Vaishnaw, A.; Gollob, J. Clinical proof of concept for a novel hepatocyte-targeting galnac-siRNA conjugate. Mol. Ther. 2017. 25, 71-78.
5. Jackson, A. L.; Burchard, J.; Leake, D.; Reynolds, A.; Schelter, J.; Guo, J.; Johnson, J. M.; Lim, L.; Karpilow, J.; Nichols, K.; Marshall, W.; Khvorova, A.; Linsley, P. S. Position-specific chemical modification of siRNAs reduces "off-target" transcript silencing. RNA 2006. 12, 1197-1205.
6. Osborn, M. F.; Khvorova, A. Improving siRNA delivery in vivo through lipid conjugation. Nucleic Acid Ther. 2018. 28, 128-136.
7. Soutschek, J.; Akinc, A.; Bramlage, B.; Charisse, K.; Constien, R.; Donoghue, M.; Elbashir, S.; Geick, A.; Hadwiger, P.; Harborth, J.; John, M.; Kesavan, V.; Lavine, G.; Pandey, R. K.; Racie, T.; Rajeev, K. G.; Rohl, I.; Toudjarska, I.; Wang, G.; Wuschko, S.; Bumcrot, D.; Koteliansky, V.; Limmer, S.; Manoharan, M.; Vornlocher, H.-P. Therapeutic silencing of an endogenous gene by systemic administration of modified siRNAs. Nature 2004. 432, 173-178.
8. Huang, H. Preclinical and clinical advances of GalNAc-decorated nucleic acid therapeutics. Mol. Ther. Nucleic Acids 2017. 6, 116-132.
9. Rajeev, K. G.; Nair, J. K.; Jayaraman, M.; Charisse, K.; Taneja, N.; O'Shea, J.; Willoughby, J. L. S.; Yucius, K.; Nguyen, T.; Shulga-Morskaya, s.; Milstein, S.; Liebow, A.; Querbes, W.; Borodovsky, A.; Fitzgerald, K.; Maier, M. A.; Manoharan, M. Hepatocyte-specific delivery of siRNAs conjugated to novel non-nucleosidic trivalent N-acetylgalactosamine elicits robust gene silencing in vivo. ChemBioChem 2015. 16, 903-908.
10. Matsuda, S.; Keiser, K.; Nair, J. K.; Charisse, K.; Manoharan, R. M.; Kretschmer, P.; Peng, C. G.; Kel'in, A. V.; Kandasamy, P.; Willoughby, J. L. S.; Liebow, A.; Querbes, W.; Yucius, K.; Nguyen, T.; Milstein, S.; Maier, M. A.; Rajeev, K. G.; Manoharan, M. siRNA conjugates carrying sequentially assembled trivalent N-acetylgalactosamine linked through nucleosides elicit robust gene silencing in vivo in hepatocytes. ACS Chem. Biol. 2015. 10, 1181-1187.

11. Prakash, T. P.; Graham, M. J.; Yu, J.; Carty, R.; Low, A.; Chappell, A.; Schmidt, K.; Zhao, C.; Aghajan, M.; Murray, H. F.; Riney, S.; Booten, S. L.; Murray, S. F.; Gaus, H.; Crosby, J.; Lima, W. F.; Guo, S.; Monia, B. P.; Swayze, E. E.; Seth, P. P. Targeted delivery of antisense oligonucleotides to hepatocytes using triantennary N-acetyl galactosamine improves potency 10-fold in mice. NAR 2014. 42, 8796-8807.

12. Tanowitz, M.; Hettrick, L.; Revenko, A.; Kinberger, G. A.; Prakash, T. P.; Seth, P. P. Asialoglycoprotein receptor 1 mediates productive uptake of N-acetylgalactosamine-conjugated and unconjugated phosphorothioate antisense oligonucleotides into liver hepatocytes. Nucleic Acids Res. 2017. 45, 12388-12400.

13. Nishina, K.; Unno, T.; Uno, Y.; Kubodera, T.; Kanouchi, T.; Mizusawa, H.; Yokota, T. Efficient in vivo delivery of siRNA to the liver by conjugation of α-tocopherol. Mol. Ther. 2008. 16, 734-740.

14. Wolfrum, C.; Shi, S.; Jayaprakash, K. N.; Jayaraman, M.; Wang, G.; Pandey, R. K.; Rajeev, K. G.; Nakayama, T.; Charrise, K.; Ndungo, E. M.; Zimmermann, T.; Koteliansky, V.; Manoharan, M.; Stoffel, M. Mechanisms and optimization of in vivo delivery of lipophilic siRNAs. Nat. Biotechnol. 2007. 25, 1149-1157.

15. Nikan, M.; Osborn, M. F.; Coles, A. H.; Biscans, A.; Godinho, B. M.; Haraszti, R. A.; Sapp, E.; Echeverria, D.; DiFiglia, M.; Aronin, N.; Khvorova, A. Synthesis and evaluation of parenchymal retention and efficacy of a metabolically stable O-phosphocholine-N-docosahexaenoyl-L-serine siRNA conjugate in mouse brain. Bioconjugate Chem. 2017. 28, 758-1766.

16. Nikan, M.; Osborn, M. F.; Coles, A. H.; Godinho, B. M.; Hall, L. M.; Haraszti, R. A.; Hassler, M. R.; Echeverria, D.; Aronin, N.; Khvorova, A. Docosahexaenoic acid conjugation enhances distribution and safety of siRNA upon local administration in mouse brain. Mol. Ther. Nucleic Acids 2016. 5, e344.

17. Biscans, A.; Coles, A.; Haraszti, R.; Echeverria, D.; Hassler, M.; Osborn, M.; Khvorova, A. Diverse lipid conjugates for functional extra-hepatic siRNA delivery in vivo NAR 2018. https://doi.org/10.1093/nar/gky 1239.

18. Osborn, M. F.; Coles, A. H.; Biscans, A.; Haraszti, R. A.; Roux, L.; Davis, S.; Ly, s.; Echeverria, D.; Hassler, M. R.; Godinho, B. M. D. C.; Nikan, M.; Khvorova, A. Hydrophobicity drives the systemic distribution of lipid-conjugated siRNAs via lipid transport pathways NAR 2018.https: //doi. org/10.1093/nar/gky 1232.

19. Sarett, S. M.; Werfel, T. A.; Lee, L.; Jackson, M. A.; Kilchrist, K. V.; Brantley-Sieders, D.; Duvall, C. L. Lipophilic siRNA targets albumin in situ and promotes bioavailability, tumor penetration, and carrier-free gene silencing. PNAS 2017. 114, E6490-E6497.

20. Karaki, S.; Benizri, S.; Mejias, R.; Baylot, V.; Branger, N.; Nguyen, T.; Vialet, B.; Oumzil, K.; Barthelemy, P.; Rocchi, P. Lipid-oligonucleotide conjugates improve cellular uptake and efficiency of TCTP-antisense in castration-resistant prostate cancer. J. Control. Release 2017. 258, 1-9.

21. Akinc, A.; Zumbuehl, A.; Goldberg, M.; Leshchiner, E. S.; Busini, V.; Hossain, N.; Bacallado, S. A.; N., N. D.; Fuller, J.; Alvarez, R.; Borodovsky, A.; Borland, T.; Constien, R.; de Fougerolles, A.; Dorkin, J. R.; Jayaprakash, K. N.; Jayaraman, M.; John, M.; Koteliansky, V.; Manoharan, M.; Nechev, L.; Racie, T.; Raitcheva, D.; Rajeev, K. G.; Sah, D. W. Y.; Soutschek, J.; Toudjarska, I.; Vornlocher, H.-P.; Zimmermann, T. S.; Langer, R.; Anderson, D. G. A combinatorial library of lipid-like materials for delivery of RNAi therapeutics. Nat. Biotechnol. 2008. 26, 561-569.

22. Chen, S.; Tam, Y. Y. C.; Lin, P. J. C.; Sung, M. M. H.; Tam, Y. K.; Cullis, P. R. Influence of particle size on the in vivo potency of lipid nanoparticle formulations of siRNA. J. Control. Release 2016. 235, 236-244.

23. Suhr, O. B.; Coelho, T.; Buades; Pouget, J.; Conceicao, I.; Berk, J.; Schmidt, H.; Waddington-Cruz; Campistol, J. M.; Bettencourt, B. R.; Vaishnaw, A.; Gollob, J.; Adams, D. Efficacy and safety of patisiran for familial amyloidotic polyneuropathy: A phase ii multi-dose study. Orphanet J. Rare Dis. 2015. 10, 1-9.

24. Dahlman, J. E.; Barnes, C.; Khan, O.; Thiriot, A.; Jhunjunwala, S.; Shaw, T. E.; Xing, Y.; Sager, H. B.; Sahay, G.; Speciner, L.; Bader, A.; Bogorad, R. L.; Yin, H.; Racie, T.; Dong, Y.; Jiang, S.; Seedorf, D.; Dave, A.; Sandu, K. S.; Webber, M. J.; Novobrantseva, T.; Ruda, V. M.; Lytton-Jean, A. K. R.; Levins, C. G.; Kalish, B.; Mudge, D. K.; Perez, M.; Abezgauz, L.; Dutta, P.; Smith, L.; Charisse, K.; Kieran, M. W.; Fitzgerald, K.; Nahrendorf, M.; Danino, D.; Tuder, R. M.; von Andrian, U. H.; Akinc, A.; Schroeder, A.; Panigrahy, D.; Kotelianski, V.; Langer, R.; Anderson, D. G. In vivo endothelial siRNA delivery using polymeric nanoparticles with low molecular weight. Nat. Nanotechnol. 2014. 9, 648-655.

25. Whitehead, K. A.; Dorkin, J. R.; Vegas, A. J.; Chang, P. H.; Veiseh, O.; Matthews, J.; Fenton, O. S.; Zhang, Y.; Olejnik, K. T.; Yesilyurt, V.; Chen, D.; Barros, S.; Klebanov, B.; Novobrantseva, T.; Langer, R.; Anderson, D. G. Degradable lipid nanoparticles with predictable in vivo siRNA delivery activity. Nat. Commun. 2014. 5, 1-10.

26. Haraszti, R. A.; Roux, L.; Coles, A. H.; Turanov, A. A.; Alterman, J. F.; Echeverria, D.; Godinho, B. M.; Aronin, N.; Khvorova, A. 5'-vinylphosphonate improves tissue accumulation and efficacy of conjugated siRNAs in vivo. Nucleic Acids Res. 2017. 45, 7581-7592.

27. Godinho, B. M. D. C.; Gilbert, J. W.; Haraszti, R. A.; Coles, A. H.; Biscans, A.; Roux, L.; Nikan, M.; Echeverria, D.; Hassler, M.; Khvorova, A. Pharmacokinetic profiling of conjugated therapeutic oligonucleotides: A high-throughput method based upon serial blood microsampling coupled to peptide nucleic acid hybridization assay. Ncleic Acid Ther. 2017. 27, 323-334.

28. Roehl, I.; Schuster, M.; Seiffert, S. Oligonucleotide detection method. US Patent US20110201006A1 2011, 1-9.

29. Coles, A. H.; Osborn, M. F.; Alterman, J. F.; Turanov, A. A.; Godinho, B. M.; Kennington, L.; Chase, K.; Aronin, N.; Khvorova, A. A high-throughput method for direct detection of therapeutic oligonucleotide-induced gene silencing in vivo. Nucleic Acid Ther. 2016. 26, 86-92.

30. Hassler, M. R.; Turanov, A. A.; Alterman, J. F.; Haraszti, R. A.; Coles, A. H.; Osborn, M. F.; Echeverria, D.; Nikan, M.; Salomon, W. E.; Roux, L.; Godinho, B. M. D. C.; Davis, S. M.; Morrissey, D. V.; Zamore, P. D.; Karumanchi, S. A.; Moore, M. J.; Aronin, N.; Khvorova, A. Comparison of partially and fully chemically-modified siRNA in conjugate-mediated delivery in vivo. Nucleic Acids Res. 2018. 46, 2185-2196.

31. Geary, R. S.; Norris, D.; Yu, R.; Bennett, C. F. Pharmacokinetics, biodistribution and cell uptake of antisense oligonucleotides. Adv. Drug. Deliv. Rev. 2015. 87, 46-51.

32. Ly, S.; Navaroli, D. M.; Didiot, M. C.; Cardia, J.; Pandarinathan, L.; Alterman, J. F.; Fogarty, K.; Standley, C.; Lifshitz, L. M.; Bellve, K. D.; Prot, M.; Echeverria, D.; Corvera, S.; Khvorova, A. Visualization of self-delivering hydrophobically modified siRNA cellular internalization. Nucleic Acids Res. 2017. 45, 15-25.
33. Allerson, C. R.; Sioufi, N.; Jarres, R.; Prakash, T. P.; Naik, N.; Berdeja, A.; Wanders, L.; Griffey, R. H.; Swayze, E. E.; Bhat, B. Fully 2'-modified oligonucleotide duplexes with improved in vitro potency and stability compared to unmodified small interfering RNA. J. Med. Chem. 2005. 48, 901-904.
34. Nallagatla, S. R.; Bevilacqua, P. C. Nucleoside modifications modulate activation of the protein kinase pkr in an RNA structure-specific manner. RNA 2008. 14, 1201-1213.
35. Ma, J. B.; Yuan, Y. R.; Meister, G.; Pei, Y.; Tuschl, T.; Patel, D. J. Structural basis for 5'-end-specific recognition of guide RNA by the A. Fulgidus piwi protein. Nature 2005. 434, 666-670.
36. Frank, F.; Sonenberg, N.; Nagar, B. Structural basis for 5'-nucleotide base-specific recognition of guide RNA by human ago2. Nature 2010. 465, 818-822.
37. Parmar, R.; Willoughby, J. L. S.; Liu, J.; Foster, D. J.; Brigham, B.; Theile, C. S.; Charisse, K.; Akinc, A.; Guidry, E.; Pei, Y.; Strapps, W.; Camilla, M.; Stanton, M. G.; Rajeev, K. G.; Sepp-Lorenzino, L.; Manoharan, M.; Meyers, R.; Maier, M. A.; Jadhav, V. 5'-(e)-vinylphosphonate: A stable phosphate mimic can improve the RNAi activity of siRNA-GalNAc conjugates. ChemBioChem 2016. 17, 987-989.
38. Lima, W. F.; Prakash, T. P.; Murray, H. M.; Kinberger, G. A.; Li, W.; Chappell, A. E.; Li, C. S.; Murray, S. F.; Gaus, H.; Seth, P. P.; Swayze, E. E.; Crooke, S. T. Single-stranded siRNAs activate RNAi in animals. Cell 2012. 150, 883-894.
39. Morrissey, D. V.; Blanchard, K.; Shaw, L.; Jensen, K.; Lockridge, J. A.; Dickinson, B.; McSwiggen, J. A.; Vargeese, C.; Bowman, K.; Shaffer, C. S.; Polisky, B. A.; Zinnen, S. Activity of stabilized short interfering RNA in a mouse model of hepatitis B virus replication. Hepatology 2005. 41, 1349-1356.
40. Harbort, J.; Elbashir, S. M.; Vandenburgh, K.; H., M.; Scaringe, S. A.; Weber, K.; Tuschl, T. Sequence, chemical, and structural variation of small interfering RNAs and short hairpin RNAs and the effect on mammalian gene silencing. Antisense Nucl. Acid Drug Dev. 2003. 13, 83-105.
41. Smith, M.; Jungalwala, F. B. Reversed-phase high performance iiquid chromatography of phosphatidylcholine: A simple method for determining relative hydrophobic interaction of various molecular species. J. Lipid Res. 1981. 22, 697-704.
42. Pokholenko, O.; Gissot, A.; Vialet, B.; Bathany, K.; Thiéry, A.; Barthelemy, P. Lipid oligonucleotide conjugates as responsive nanomaterials for drug delivery. J. Mater. Chem. B 2013. 1, 5329-5334.
43. Liu, B.; Chang, J.; Gordon, W. P.; Isbell, J.; Yingyao, Z.; Tuntland, T. Snapshot pk: A rapid rodent in vivo preclinical screening approach. Drug Discovery Today 2008. 13, 360-367.
44. Reed, D. R.; Bachmanov, A. A.; Tordoff, M. G. Forty mouse strain survey of body composition. Physiol. Behav. 2007. 91, 593-600.
45. Wanke, R.; Milz, S.; Rieger, N.; Ogiolda, L.; Renner-Müller, I.; Brem, G.; Hermanns, W.; Wolf, E. Overgrowth of skin in growth hormone transgenic mice depends on the presence of male gonads. J. Investig. Dermatol. 1999. 113, 967-971.
46. Taniguchi, T.; Miyauchi, E.; Nakamura, S.; Hirai, M.; Suzue, K.; Imai, T.; Nomura, T.; Handa, T.; Okada, H.; Shimokawa, C.; Onishi, R.; Olia, A.; Hirata, J.; Tomita, H.; Ohno, H.; Horii, T.; Hisaedaa, H. *Plasmodium berghei* anka causes intestinal malaria associated with dysbiosis. Sci. Rep. 2015. 5, 1-12.
47. Alterman, J. F.; Hall, L. M.; Coles, A. H.; Hassler, M. R.; Didiot, M.-C.; Chase, K.; Abraham; Sottosanti, E.; Johnson, E.; Sapp, E.; Osborn, M. F.; DiFiglia, M.; Aronin, N.; Khvorova, A. Hydrophobically modified siRNAs silence huntingtin mRNA in primary neurons and mouse brain. Mol. Ther. Nucleic Acids 2015. 4, e266.
48. Oberbauer, R.; Schreiner, G. F.; Meyer, T. W. Renal uptake of an 18-mer phosphorothioate oligonucleotide. Kidney Int. 1995. 48, 1226-1232.
49. Khvorova, A. Oligonucleotide therapeutics—a new class of cholesterol-lowering drugs. N. Engl. J. Med. 2017. 376, 4-7.
50. Solano, E. C.; Kornbrust, D. J.; Beaudry, A.; Foy, J. W.; Schneider, D. J.; Thompson, J. D. Toxicological and pharmacokinetic properties of qpi-1007, a chemically modified synthetic siRNA targeting caspase 2 mRNA, following intravitreal injection. Nucleic Acid Ther. 2014. 24, 258-266.
51. Thompson, J. D.; Kornbrust, D. J.; Foy, J. W.; Solano, E. C.; Schneider, D. J.; Feinstein, E.; Molitoris, B. A.; Erlich, S. Toxicological and pharmacokinetic properties of chemically modified siRNAs targeting p53 RNA following intravenous administration. Nucleic Acid Ther. 2012. 22, 255-264.
52. Geary, R. S. Antisense oligonucleotide pharmacokinetics and metabolism. Expert Opin. Drug Metab. Toxicol. 2009. 5, 381-391.
53. Khan, T.; Weber, H.; DiMuzio, J.; Matter, A.; Dogdas, B.; Shah, T.; Thankappan, A.; Disa, J.; Jadhav, V.; Lubbers, L.; Sepp-Lorenzino, L.; Strapps, W. R.; Tadin-Strapps, M. Silencing myostatinusing cholesterol-conjugated siRNAs induces muscle growth. Mol. Ther. Nucleic Acids 2016. 5, e342.

INCORPORATION BY REFERENCE

The contents of all cited references (including literature references, patents, patent applications, and websites) that maybe cited throughout this application are hereby expressly incorporated by reference in their entirety for any purpose, as are the references cited therein. The disclosure will employ, unless otherwise indicated, conventional techniques of immunology, molecular biology and cell biology, which are well known in the art.

The present disclosure also incorporates by reference in their entirety techniques well known in the field of molecular biology and drug delivery. These techniques include, but are not limited to, techniques described in the following publications:

Atwell et al. J. Mol. Biol. 1997, 270: 26-35;

Ausubel et al. (eds.), CURRENT PROTOCOLS IN MOLECULAR BIOLOGY, John Wiley & Sons, N Y (1993);

Ausubel, F. M. et al. eds., SHORT PROTOCOLS IN MOLECULAR BIOLOGY (4th Ed. 1999) John Wiley & Sons, NY. (ISBN 0-471-32938-X);

Controlled Drug Bioavailability, Drug Product Design and Performance, Smolen and Ball (eds.), Wiley, New York (1984);

Giege, R. and Ducruix, A. Barrett, CRYSTALLIZATION OF NUCLEIC ACIDS AND PROTEINS, a Practical Approach, 2nd ea., pp. 20 1-16, Oxford University Press, New York, N.Y., (1999);

Goodson, in Medical Applications of Controlled Release, vol. 2, pp. 115-138 (1984);

Hammerling, et al., in: MONOCLONAL ANTIBODIES AND T-CELL HYBRIDOMAS 563-681 (Elsevier, N.Y., 1981;

Harlow et al., ANTIBODIES: A LABORATORY MANUAL, (Cold Spring Harbor Laboratory Press, 2nd ed. 1988);

Kabat et al., SEQUENCES OF PROTEINS OF IMMUNOLOGICAL INTEREST (National Institutes of Health, Bethesda, Md. (1987) and (1991);

Kabat, E. A., et al. (1991) SEQUENCES OF PROTEINS OF IMMUNOLOGICAL INTEREST, Fifth Edition, U.S. Department of Health and Human Services, NIH Publication No. 91-3242;

Kontermann and Dubel eds., ANTIBODY ENGINEERING (2001) Springer-Verlag. New York. 790 pp. (ISBN 3-540-41354-5).

Kriegler, Gene Transfer and Expression, A Laboratory Manual, Stockton Press, N Y (1990);

Lu and Weiner eds., CLONING AND EXPRESSION VECTORS FOR GENE FUNCTION ANALYSIS (2001) BioTechniques Press. Westborough, Mass. 298 pp. (ISBN 1-881299-21-X).

MEDICAL APPLICATIONS OF CONTROLLED RELEASE, Langer and Wise (eds.), CRC Pres., Boca Raton, Fla. (1974);

Old, R. W. & S. B. Primrose, PRINCIPLES OF GENE MANIPULATION: AN INTRODUCTION TO GENETIC ENGINEERING (3d Ed. 1985) Blackwell Scientific Publications, Boston. Studies in Microbiology; V. 2:409 pp. (ISBN 0-632-01318-4).

Sambrook, J. et al. eds., MOLECULAR CLONING: A LABORATORY MANUAL (2d Ed. 1989) Cold Spring Harbor Laboratory Press, NY. Vols. 1-3. (ISBN 0-87969-309-6).

SUSTAINED AND CONTROLLED RELEASE DRUG DELIVERY SYSTEMS, J. R. Robinson, ed., Marcel Dekker, Inc., New York, 1978

Winnacker, E. L. FROM GENES TO CLONES: INTRODUCTION TO GENE TECHNOLOGY (1987) VCH Publishers, NY (translated by Horst Ibelgaufts). 634 pp. (ISBN 0-89573-614-4).

EQUIVALENTS

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

What is claimed:

1. An siRNA-lipid conjugate represented by the following formula:

Y-L-(H)

wherein:
Y is an siRNA molecule comprising a sense strand and an antisense strand,
L is a linker, and Y-L comprise the structure:

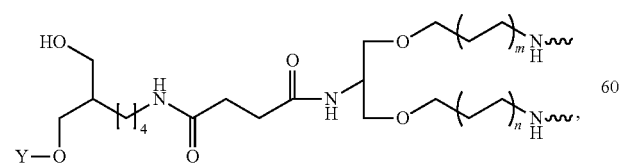

wherein each m and n comprises 1, 2, 3, 4, or 5,
each H is independently a hydrophobic chain comprising 5 to 50 carbon atoms, and linker L is bonded to the 3' end of the sense strand of the siRNA.

2. The siRNA-lipid conjugate according to claim 1, wherein the hydrophobic chain of at least one H is a linear or branched aliphatic chain comprising 10 to 30 carbon atoms.

3. The siRNA-lipid conjugate according to claim 1, wherein the hydrophobic chain of at least one H is derived from a linear or branched fatty acid and the carbonyl group of the fatty acid is attached to the linker by an amide bond.

4. The siRNA-lipid conjugate according to claim 3, wherein the fatty acid is selected from the group consisting of myristic, docosahexaenoic, and eicosapentaenoic.

5. The siRNA-lipid conjugate according to claim 1, wherein each H is independently an aliphatic chain comprising 12 to 26 carbon atoms.

6. The siRNA-lipid conjugate according to claim 1, wherein each H is a branched chain comprising 24 to 48 carbon atoms.

7. The siRNA-lipid conjugate according to claim 1, wherein the linker is attached to an H by a bond selected from the group consisting of an ester bond, an amide bond, an ether bond, a thioether bond, a nitrogen-carbon covalent bond, and combinations thereof.

8. The siRNA-lipid conjugate according to claim 1, wherein the linker L is covalently bonded to Y and each H.

9. The siRNA-lipid conjugate according to claim 1, wherein said siRNA comprises at least one modified nucleotide.

10. The siRNA-lipid conjugate according to claim 9, wherein said modified nucleotide comprises a 2'-O-methyl modified nucleotide, a 2'-deoxy-2'-fluoro modified nucleotide, a nucleotide comprising a 5'-phosphorothioate group, or a terminal nucleotide linked to an E-vinylphosphate group.

11. The siRNA-lipid conjugate according to claim 9, wherein said modified nucleotide comprises a 2'-deoxy-modified nucleotide, a locked nucleotide, an abasic nucleotide, 2'-amino-modified nucleotide, 2'-alkyl-modified nucleotide, morpholino nucleotide, a phosphoramidate, or a non-natural base comprising nucleotide.

12. The siRNA-lipid conjugate according to claim 1, wherein the siRNA comprises at least one 2'-O-methyl modified nucleotide, at least one 2'-deoxy-2'-fluoro modified nucleotide, and at least one nucleotide comprising a 5'-phosphorothioate group.

13. The siRNA-lipid conjugate according to claim 1, wherein at least 80% of the nucleotides of the siRNA are chemically modified.

14. The siRNA-lipid conjugate according to claim 1, wherein all the nucleotides of the siRNA are chemically modified.

15. The siRNA-lipid conjugate according to claim 1, wherein:
(1) the sense strand of the siRNA molecule comprises alternating 2'-methoxy-ribonucleotides and 2'-fluoro-ribonucleotides;
(2) the antisense strand of the siRNA molecule comprises alternating 2'-methoxy-ribonucleotides and 2'-fluoro-ribonucleotides;
(3) the nucleotides of the sense strand are connected via phosphodiester or phosphorothioate linkages; and
(4) the nucleotides of the antisense strand are connected via phosphodiester or phosphorothioate linkages.

16. A pharmaceutical composition for inhibiting the expression of a gene in an organism, comprising the siRNA-lipid conjugate according to claim 1 and a pharmaceutically acceptable carrier.

17. The siRNA-lipid conjugate according to claim 1, wherein n and m are 1.

* * * * *